(12) United States Patent
Ohashi et al.

(10) Patent No.: US 10,173,975 B2
(45) Date of Patent: Jan. 8, 2019

(54) SULFONIUM COMPOUND, RESIST COMPOSITION, AND PATTERN FORMING PROCESS

(71) Applicant: Shin-Etsu Chemical Co., Ltd., Tokyo (JP)

(72) Inventors: Masaki Ohashi, Joetsu (JP); Takayuki Fujiwara, Joetsu (JP); Ryosuke Taniguchi, Joetsu (JP); Kazuya Honda, Joetsu (JP); Takahiro Suzuki, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/730,066

(22) Filed: Oct. 11, 2017

(65) Prior Publication Data

US 2018/0099928 A1 Apr. 12, 2018

(30) Foreign Application Priority Data

Oct. 12, 2016 (JP) .................................. 2016-200813

(51) Int. Cl.
*G03F 7/004* (2006.01)
*C07C 381/12* (2006.01)
(Continued)

(52) U.S. Cl.
CPC .......... *C07C 381/12* (2013.01); *C07C 317/04* (2013.01); *C07C 317/28* (2013.01);
(Continued)

(58) Field of Classification Search
CPC ... G03F 7/004; G03F 7/32; G03F 7/26; G03F 7/0045; G03F 7/0397; G03F 7/2041;
(Continued)

(56) References Cited

U.S. PATENT DOCUMENTS 6,492,091 B2 12/2002 Kodama et al.

FOREIGN PATENT DOCUMENTS

JP 4226803 B2 2/2009

OTHER PUBLICATIONS

Hou et al, "Synthesis of Stable 2-sulfoniophenolate", Chinese Science Bulletin, vol. 45, issue 16, pp. 1480-1484(2000).*

* cited by examiner

*Primary Examiner* — Amanda C. Walke
(74) *Attorney, Agent, or Firm* — Westerman, Hattori, Daniels & Adrian, LLP

(57) ABSTRACT

A sulfonium compound having formula (1) is provided wherein $R^1$, $R^2$ and $R^3$ are a $C_1$-$C_{20}$ monovalent hydrocarbon group which may contain a heteroatom, p=0-5, q=0-5, and r=0-4. A resist composition comprising the sulfonium compound is processed by lithography to form a resist pattern with improved LWR and pattern collapse.

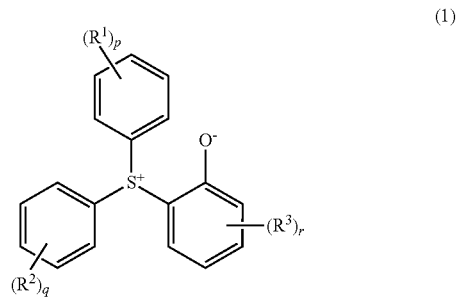

11 Claims, 4 Drawing Sheets

(51) Int. Cl.
*H01L 21/027* (2006.01)
*C08F 220/18* (2006.01)
*C08F 220/38* (2006.01)
*G03F 7/20* (2006.01)
*C08F 220/24* (2006.01)
*G03F 7/26* (2006.01)
*C07C 317/04* (2006.01)
*C07C 317/28* (2006.01)
*C08K 5/36* (2006.01)
*G03F 7/033* (2006.01)
*G03F 7/32* (2006.01)
*C08L 33/08* (2006.01)
*C08L 33/10* (2006.01)
*C08L 33/16* (2006.01)
*G01R 33/46* (2006.01)

(52) U.S. Cl.
CPC .......... *C08F 220/18* (2013.01); *C08F 220/24* (2013.01); *C08F 220/38* (2013.01); *C08K 5/36* (2013.01); *G03F 7/0045* (2013.01); *G03F 7/033* (2013.01); *G03F 7/2004* (2013.01); *G03F 7/2041* (2013.01); *G03F 7/26* (2013.01); *G03F 7/322* (2013.01); *H01L 21/0274* (2013.01); *C07C 2602/42* (2017.05); *C07C 2603/74* (2017.05); *C08L 33/08* (2013.01); *C08L 33/10* (2013.01); *C08L 33/16* (2013.01); *G01R 33/46* (2013.01)

(58) Field of Classification Search
CPC .... G03F 7/2004; C07C 381/12; C08F 220/18; C08F 220/24; C08F 220/38; H01L 21/0274
USPC ..... 430/913, 270.1, 322, 325, 329, 331, 942
See application file for complete search history.

SULFONIUM COMPOUND, RESIST COMPOSITION, AND PATTERN FORMING PROCESS

CROSS-REFERENCE TO RELATED APPLICATION

This non-provisional application claims priority under 35 U.S.C. § 119(a) on Patent Application No. 2016-200813 filed in Japan on Oct. 12, 2016, the entire contents of which are hereby incorporated by reference.

TECHNICAL FIELD

This invention relates to a novel sulfonium compound of specific structure, a resist composition comprising the same, and a pattern forming process using the resist composition.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser is requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. While the ArF immersion lithography has entered the commercial stage, the technology still needs a resist material which is substantially non-leachable in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in enhancing the transparency of a resin alone.

With the rapid progress toward miniaturization, it becomes difficult to form a pattern of desired size from such a resist material. In particular, the influence of acid diffusion is detrimental to lithography performance. As the pattern size is approaching the diffusion length of acid, the degradation of contrast becomes more serious. As the mask error factor (MEF), indicative of a dimensional shift on wafer relative to a dimensional shift on mask, increases, a noticeable drop of mask fidelity ensues. In addition, since the fluctuation of pattern line width, known as line width roughness (LWR), and the critical dimension uniformity (CDU) of patterns are largely affected by acid diffusion, degradation of these parameters becomes a problem.

To solve the problems, studies have been made on acid diffusion inhibitors as well as base resins and photoacid generators. Amines are typically used as the acid diffusion inhibitor. Many problems associated with LWR as an index of pattern roughness are left unsolved. Also the use of weak acid onium salts as the diffusion inhibitor is under study. For example, Patent Document 1 describes a positive photosensitive composition for ArF excimer laser lithography comprising a carboxylic acid onium salt. This system is based on the mechanism that a salt exchange occurs between the weak acid onium salt and a strong acid (sulfonic acid) generated by a PAG upon exposure. That is, the strong acid (α,α-difluorosulfonic acid) having high acidity is replaced by a weak acid (alkanesulfonic acid or carboxylic acid), thereby suppressing acidolysis reaction of acid labile group and reducing or controlling the distance of acid diffusion. The onium salt apparently functions as a quencher, that is, acid diffusion inhibitor. In particular, acid diffusion inhibitors of sulfonium salt type are effective for improving LWR, but poor in contrast and MEF as compared with amine compounds. Because of a low contrast, parameters such as resolution and collapse limit are poor.

CITATION LIST

Patent Document 1: JP 4226803 (U.S. Pat. No. 6,492,091)

DISCLOSURE OF INVENTION

An object of the invention is to provide a resist composition capable of forming a resist film which has improved LWR and MEF and is resistant to pattern collapse when processed by DUV, EUV and EB lithography, a sulfonium compound for use therein, and a pattern forming process using the resist composition.

The inventors have found that a resist composition comprising a sulfonium compound of specific structure can be processed by lithography to form a resist pattern which is improved in LWR, MEF and collapse resistance, and is suited for high accuracy micropatterning.

In one aspect, the invention provides a sulfonium compound having the formula (1).

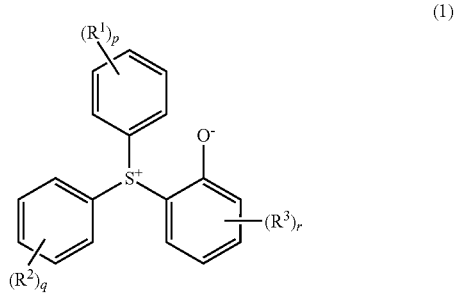

Herein $R^1$, $R^2$ and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, and in case of r=2 to 4, two adjoining groups $R^3$ may bond together to form a ring with the carbon atoms to which they are attached.

In another aspect, the invention provides a resist composition comprising (A) the sulfonium compound of formula (1) and (B) an organic solvent.

The resist composition may further comprise (C) a polymer comprising recurring units having an acid labile group.

Preferably the recurring units having an acid labile group have the formula (a).

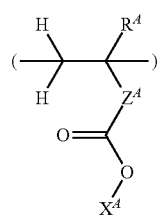

(a)

Herein $R^A$ is hydrogen, fluorine, methyl or trifluoromethyl, $Z^A$ is a single bond, phenylene, naphthylene or (backbone)-C(=O)—O—Z'—, Z' is a $C_1$-$C_{10}$ straight, branched or cyclic alkylene group which may contain a hydroxyl moiety, ether bond, ester bond, or lactone ring, or a phenylene or naphthylene group, and $X^A$ is an acid labile group.

The polymer may further comprise recurring units having the formula (b).

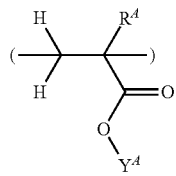

(b)

Herein $R^A$ is hydrogen, fluorine, methyl or trifluoromethyl, and $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

The resist composition may further comprise (D) a photoacid generator. The preferred photoacid generator has the formula (2) or (3).

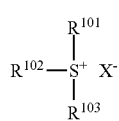

(2)

Herein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, and $X^-$ is an anion selected from the formulae (2A) to (2D):

(2A)

(2B)

(2C)

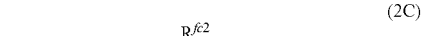

(2D)

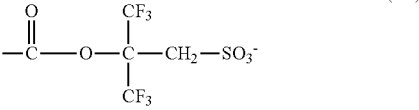

wherein $R^{fa}$, $R^{fb1}$, $R^{fb2}$, $R^{fc1}$, $R^{fc2}$, and $R^{fc3}$ are each independently fluorine or a $C_1$-$C_{40}$ straight, branched or cyclic monovalent hydrocarbon group which may contain a heteroatom, $R^{fb1}$ and $R^{fb2}$, or $R^{fc1}$ and $R^{fc2}$ may bond together to form a ring with the carbon atoms to which they are attached and the atoms therebetween, $R^{fd}$ is a $C_1$-$C_{40}$ straight, branched or cyclic monovalent hydrocarbon group which may contain a heteroatom.

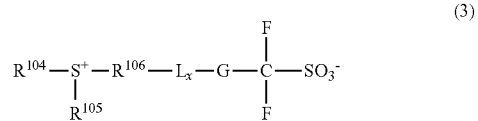

(3)

Herein $R^{104}$ and $R^{105}$ are each independently a $C_1$-$C_{20}$ straight, branched or cyclic monovalent hydrocarbon group which may contain a heteroatom, $R^{104}$ and $R^{105}$ may bond together to form a ring with the sulfur atom to which they are attached, $R^{106}$ is a $C_1$-$C_{20}$ straight, branched or cyclic divalent hydrocarbon group which may contain a heteroatom, G is a single bond or a $C_1$-$C_{20}$ straight, branched or cyclic divalent hydrocarbon group which may contain a heteroatom, and $L_x$ is a divalent linking group.

The resist composition may further comprise (E) a nitrogen-containing compound and (F) a surfactant which is insoluble or substantially insoluble in water and soluble in alkaline developer and/or a surfactant which is insoluble or substantially insoluble in water and alkaline developer.

In a further aspect, the invention provides a pattern forming process comprising the steps of applying the resist composition defined above onto a substrate, prebaking to form a resist film, exposing the resist film to KrF excimer laser, ArF excimer laser, EB or EUV through a photomask, baking, and developing the exposed resist film in a developer.

In a preferred embodiment, the exposing step is by immersion lithography wherein a liquid having a refractive index of at least 1.0 is interposed between the resist film and a projection lens.

The pattern forming process may further comprise the step of forming a protective film on the resist film, and in the immersion lithography, the liquid is interposed between the protective film and the projection lens.

ADVANTAGEOUS EFFECTS OF INVENTION

The sulfonium compound exerts a satisfactory acid diffusion control (or quencher) function in a resist composition. The resist composition comprising the same forms a pattern of good profile with improved LWR, MEF and collapse resistance.

BRIEF DESCRIPTION OF ACCOMPANYING DRAWINGS

DESCRIPTION OF EMBODIMENTS

Figure 1:
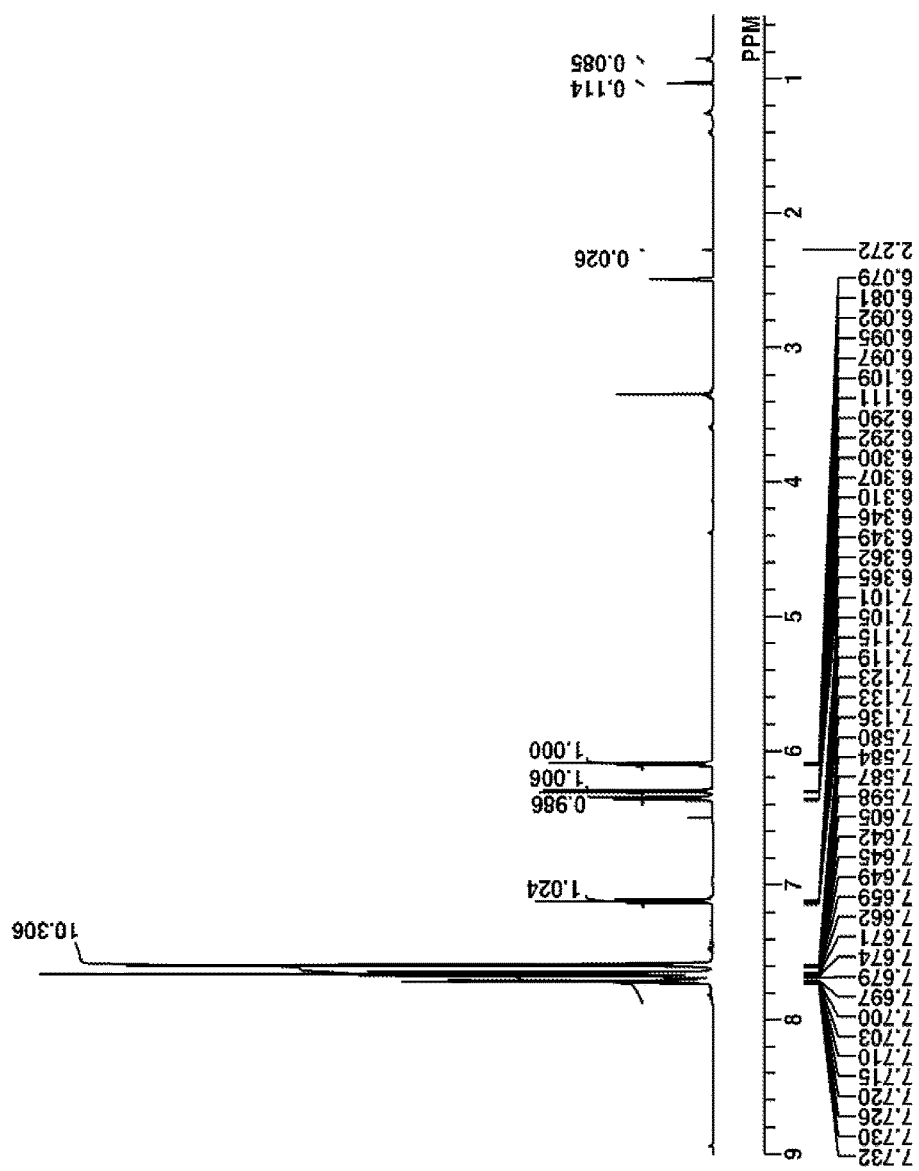
FIG. 1 is a diagram of $^1$H-NMR spectrum of compound Q-A obtained in Example 1-1.

As used herein, the singular forms "a," "an" and "the" include plural referents unless the context clearly dictates otherwise. The notation (Cn-Cm) means a group containing from n to m carbon atoms per group. In chemical formulae, the broken line denotes a valence bond; Me stands for methyl, Ph for phenyl, and Ac for acetyl.

The abbreviations and acronyms have the following meaning.
EB: electron beam
EUV: extreme ultraviolet
Mw: weight average molecular weight
Mw/Mn: molecular weight distribution or dispersity
GPC: gel permeation chromatography
PEB: post-exposure bake
PAG: photoacid generator
LWR: line width roughness
MEF: mask error factor Sulfonium Compound One embodiment of the invention is a sulfonium compound having the formula (1).

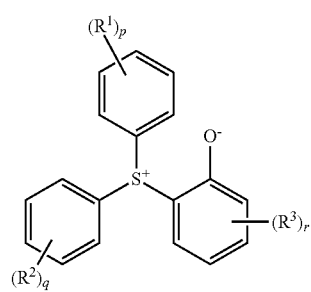

(1)

In formula (1), $R^1$, $R^2$ and $R^3$ are each independently a $C_1$-$C_{20}$ straight, branched or cyclic monovalent hydrocarbon group which may contain a heteroatom. Suitable monovalent hydrocarbon groups include alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and aryl groups such as phenyl, naphthyl, and anthracenyl. In these groups, one or more hydrogen atom may be replaced by a radical containing a heteroatom such as oxygen, sulfur, nitrogen or halogen, or a radical containing a heteroatom such as oxygen, sulfur or nitrogen may intervene between carbon atoms, or the carbon atom in the group bonded to the benzene ring may be replaced by a radical containing a heteroatom such as oxygen, sulfur or nitrogen, so that the group may contain a hydroxyl, cyano, carbonyl, ether bond, thioether bond, ester bond, sulfonate (sulfonic acid ester) bond, carbonate bond, carbamate bond, lactone ring, sultone ring, carboxylic anhydride or haloalkyl radical.

In formula (1), p and q are each independently an integer of 0 to 5, and r is an integer of 0 to 4. Each of p, q and r is preferably equal to 0, 1 or 2 for ease of synthesis and availability of reactants.

In case of p=2 to 5, two adjoining groups $R^1$ may bond together to form a ring with the carbon atoms to which they are attached. In case of q=2 to 5, two adjoining groups $R^2$ may bond together to form a ring with the carbon atoms to which they are attached. In case of r=2 to 4, two adjoining groups $R^3$ may bond together to form a ring with the carbon atoms to which they are attached.

Examples of the sulfonium compound having formula (1) are shown below, but not limited thereto.

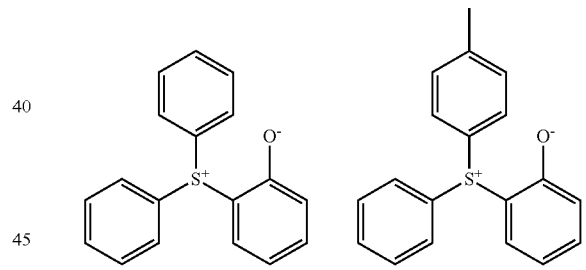

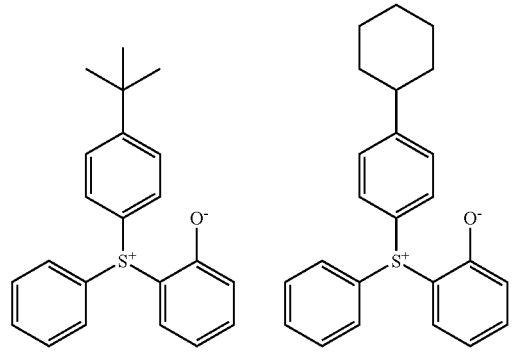

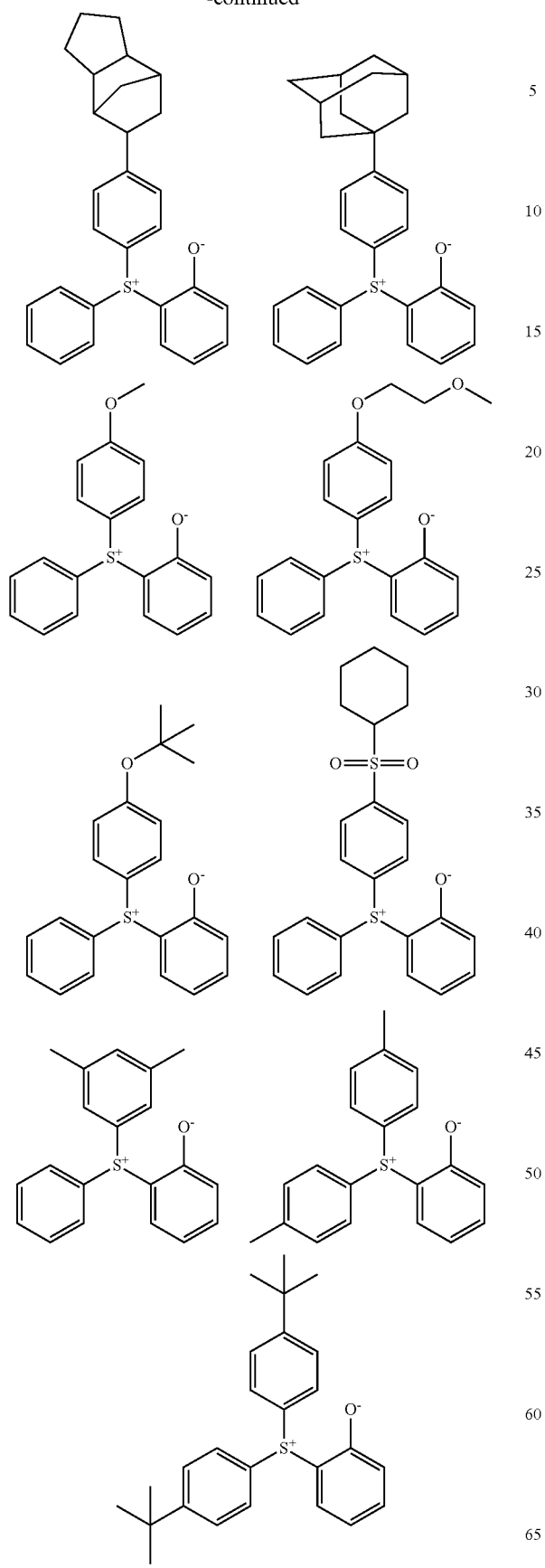
The sulfonium compound may be synthesized by a combination of well-known organic chemistry techniques, for example, according to the following scheme.

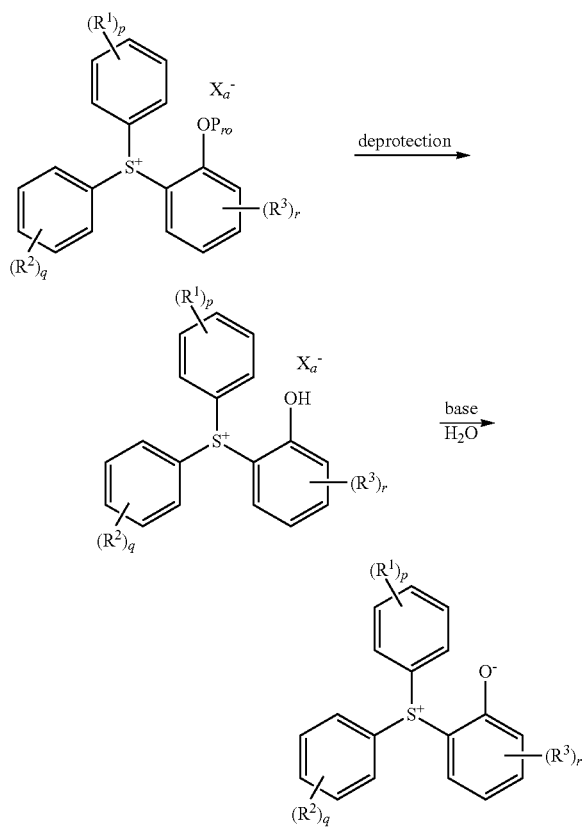

Herein $R^1$, $R^2$, $R^3$, p, q and r are as defined above, $X_a^-$ is an anion, and $P_{ro}$ is a protective group.

There is first furnished a sulfonium salt having a sulfonium cation wherein the carbon atom at α-position relative to the sulfur atom is substituted with a protected hydroxyl group. The protective group for hydroxyl is not particularly limited and may be any of protective groups used in general organic synthesis, such as tert-butyl and methoxymethyl. On the sulfonium salt, deprotection reaction of hydroxyl group is performed, followed by treatment with a base and separatory extraction with organic solvent-water combination. The inventive sulfonium salt is extracted in the organic layer. Examples of the base used herein include sodium hydroxide and tetramethylammonium hydroxide, but are not limited thereto.

The sulfonium compound defined herein functions quite effectively as an acid diffusion inhibitor when applied to a resist composition. As used herein, the term "acid diffusion inhibitor" is a compound which traps the acid generated by the PAG in the resist composition in the exposed region to prevent the acid from diffusing into the unexposed region for thereby forming the desired pattern.

The inventive sulfonium compound follows an acid diffusion controlling mechanism which is described below. The acid generated by the PAG in the resist composition in the exposed region should have a strong acidity enough to deprotect the acid labile group on the base resin. For example, sulfonic acid which is fluorinated at α-position relative to sulfo group, imidic acid and methidic acid are used in the ArF lithography. In a resist composition system where the PAG and the inventive sulfonium compound co-exist, the acid generated by the PAG is trapped by the sulfonium compound, which is converted from betaine to a sulfonium salt. Another mechanism that the inventive sulfonium compound itself is photo-decomposed is contemplated. The compound resulting from photo-decomposition is a weakly acidic phenolic compound having an insufficient acidity to deprotect the acid labile group on the base resin. Accordingly the inventive sulfonium compound intensely functions as an acid diffusion inhibitor.

The acid diffusion inhibitor, which is also referred to as onium salt type quencher, tends to form a resist pattern with a reduced LWR as compared with the conventional quenchers in the form of amine compounds. This is presumably because salt exchange between strong acid and the inventive sulfonium compound is infinitely repeated. The site where strong acid is generated at the end of exposure shifts from the site where the onium salt of strong acid generation type is initially present. It is believed that since the cycle of photo-acid generation and salt exchange is repeated many times, acid generation points are averaged, and this smoothing effect leads to a resist pattern with reduced LWR after development.

Regarding the compound that exerts a quencher effect via the same mechanism, Patent Document 1 and JP-A 2003-005376 report carboxylic acid onium salts, alkanesulfonic acid onium salts, and arylsulfonic acid onium salts as the acid diffusion inhibitor. On use of an alkanesulfonic acid onium salt or arylsulfonic acid onium salt, the generated acid has such an acid strength that part thereof in the overexposed region may induce deprotection reaction of the acid labile group on the base resin, leading to an increase of acid diffusion, which invite degradation of resist performance parameters like resolution and MEF. Also in the case of carboxylic acid onium salt, the generated carboxylic acid has a weak acidity and is not reactive with the acid labile group on the resin. Thus the carboxylic acid onium salt achieves some improvement as acid diffusion inhibitor, but less satisfactory in a more miniaturized region. There is left room for improvements in an overall balance of resolution, MEF, and LWR. It is believed that the so-called salt type quencher as mentioned above undergoes equilibration reaction rather than quick reaction with the generated acid. This suggests that its acid diffusion controlling ability is inferior to the amine compound type quencher. When an amine compound is used as quencher, its acid diffusion controlling function is satisfactory, but LWR is inferior because of the lack of repeating salt exchange reactions as found in the salt type quencher.

In contrast, the inventive sulfonium compound achieves substantial improvements in resist performance, which are not achievable with the above-mentioned acid diffusion inhibitors. Although the reason is not clearly understood, the following reason is presumed.

The inventive sulfonium compound is characterized by a betaine structure possessing a sulfonium cation and a phenoxide anion within a common molecule, and the phenoxide moiety at the ortho position relative to $S^+$. Since the phenoxide anion is in proximity to $S^+$, it is presumed that the sulfonium compound takes a hypervalent structure, and $S^+$ and phenoxide moiety are nearly in the three-center four-electron bond having a shorter bond distance than ordinary ionic bond, that is, covalent bond. Owing to this structural specificity, the sulfonium phenoxide which is normally unstable exists in a stable manner. Further, since the ionic bond is weakened as discussed above, organic solvent solubility is improved, and as a result, uniform dispersion in the resist composition is improved and LWR is reduced or improved. While the conventional salt type quencher undergoes equilibration reaction on trapping the acid generated from the PAG and is thus inferior in acid diffusion controlling ability as alluded to previously, the inventive sulfonium compound follows irreversible reaction. This is driven by the mechanism that on trapping acid, the sulfonium compound converts from the betaine structure to a stabler salt type structure. In addition, the counter anion of the inventive sulfonium compound is a strongly basic phenoxide. For the above reasons, the inventive sulfonium compound has an excellent acid diffusion controlling ability. Thus MEF and contrast are improved. There is available a resist composition having improved resolution and collapse resistance.

JP-A 2013-006827 describes a sulfonium carboxylate compound as the betaine type sulfonium compound and a resist composition comprising the same. In some exemplary compounds, carboxylate is incorporated at the ortho position relative to $S^+$. However, the exemplary compounds described therein are limited to alkylsulfonium carboxylate compounds because of the preparation method. No reference is made to the triarylsulfonium compounds having carboxylate incorporated at the ortho position relative to $S^+$, as in the present invention. See JP-A 2013-006827, paragraphs [0037]-[0039]. In general, triarylsulfonium salts have higher stability than alkylsulfonium salts. For example, the alkylsulfonium salt behaves such that under the action of heat or nucleophilic reagent, the sulfonium cation is readily decomposed into a sulfide compound. That is, the sulfonium carboxylate compound of JP-A 2013-006827 is uncertain in storage stability, and the resist composition with which it can be combined is undesirably limited. Furthermore, the inventive sulfonium compound has a strongly basic phenoxide anion whereas the compound having carboxylate as the counter anion as described in JP-A 2013-006827 is inferior in basicity and lacks acid diffusion controlling ability. As used herein, the alkylsulfonium salt means that at least one of three valence bonds to $S^+$ is alkyl.

Also, JP-A 2016-006495 (US 20150346599) describes a non-betaine type sulfonium compound having phenoxide as the counter anion. However, since the non-betaine type sulfonium phenoxide is extremely water soluble, it is difficult to introduce a water washing step. While it is well known to the artisan that one of requirements imposed to KrF and ArF resist compositions is to reduce the metal content as low as possible, the water washing step is essential for metal reduction. In fact, JP-A 2016-006495 refers to a non-aqueous formulation using a silver salt in Example, indicating that silver is left in the formulation. In contrast, the inventive sulfonium compound can be extracted in organic layer by virtue of its structural specificity, even when the water washing step is introduced. Furthermore, the sulfonium compound of JP-A 2016-006495 is low in shelf stability because the phenoxide anion is not stabilized unlike the inventive sulfonium compound, and fails to exert the desired performance because excessive decomposition reaction can take place upon exposure so that it may not fully function as the acid diffusion inhibitor.

Resist Composition

Another embodiment of the invention is directed to a resist composition comprising (A) an acid diffusion inhibitor in the form of a sulfonium compound having formula (1) as an essential component, (B) an organic solvent, (C) a base resin, and (D) a photoacid generator. If necessary, the resist composition may further comprise (E) a nitrogen-containing compound, and (F) a surfactant which is insoluble or substantially insoluble in water and soluble in alkaline developer and/or a surfactant which is insoluble or substantially insoluble in water and alkaline developer (hydrophobic resin).

An appropriate amount of the acid diffusion inhibitor (A) is 0.1 to 40 parts, more preferably 1 to 20 parts by weight per 100 parts by weight of the base resin (C). As long as its amount is in the range, the sulfonium compound fully functions as an acid diffusion inhibitor, eliminating any performance problems such as sensitivity drop, solubility shortage, and foreign particles. The sulfonium compound may be used alone or in admixture of two or more.

(B) Organic Solvent

Component (B) is an organic solvent, which is not particularly limited as long as the components are soluble therein. Examples of the organic solvent are described in JP-A 2008-111103, paragraphs [0144]-[0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof.

An appropriate amount of the organic solvent (B) used is 200 to 5,000 parts, more preferably 400 to 3,000 parts by weight per 100 parts by weight of the base resin (C).

(C) Base Resin

The base resin used in the resist composition preferably contains a polymer comprising recurring units having an acid labile group. The recurring units having an acid labile group include units having the formula (a).

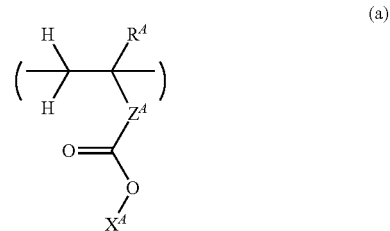

Herein $R^A$ is hydrogen, fluorine, methyl or trifluoromethyl. $Z^A$ is a single bond, phenylene, naphthylene or (backbone)-C(=O)—O—Z'—, wherein Z' is a $C_1$-$C_{10}$ straight, branched or cyclic alkylene group which may contain a hydroxyl moiety, ether bond, ester bond, or lactone ring, or a phenylene or naphthylene group. $X^A$ is an acid labile group.

Examples of the structure of formula (a) wherein $Z^A$ is a variant are illustrated below, but not limited thereto. $R^A$ and $X^A$ are as defined above.

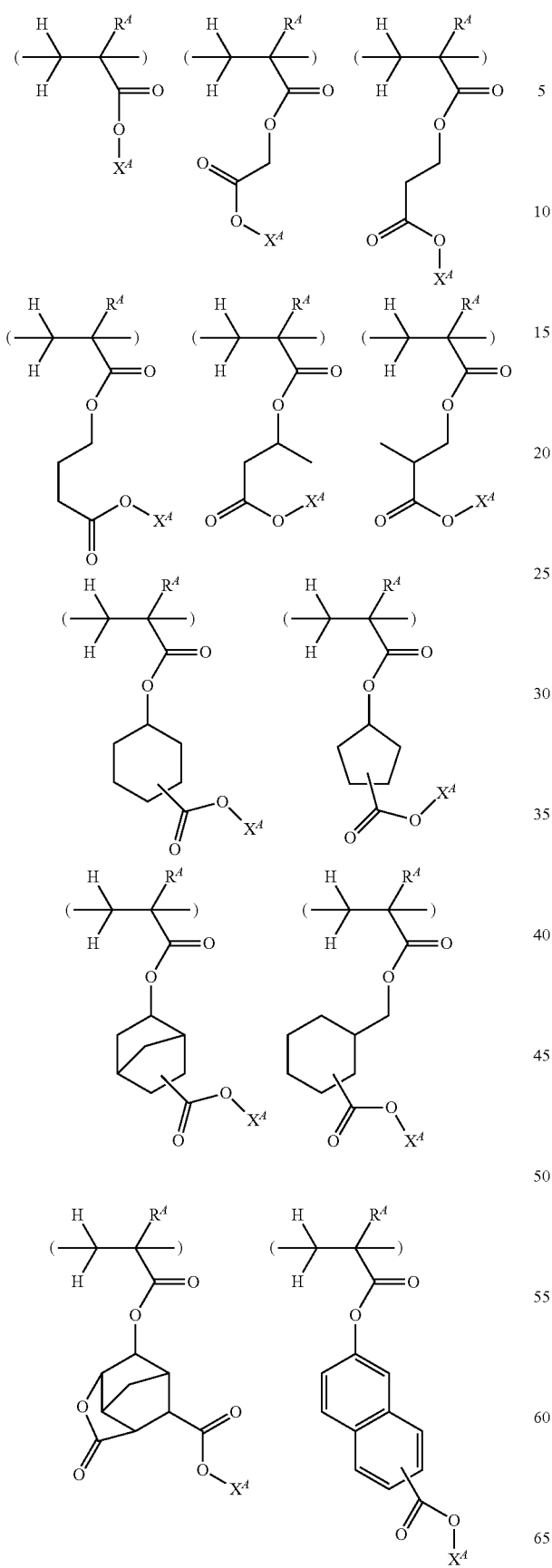
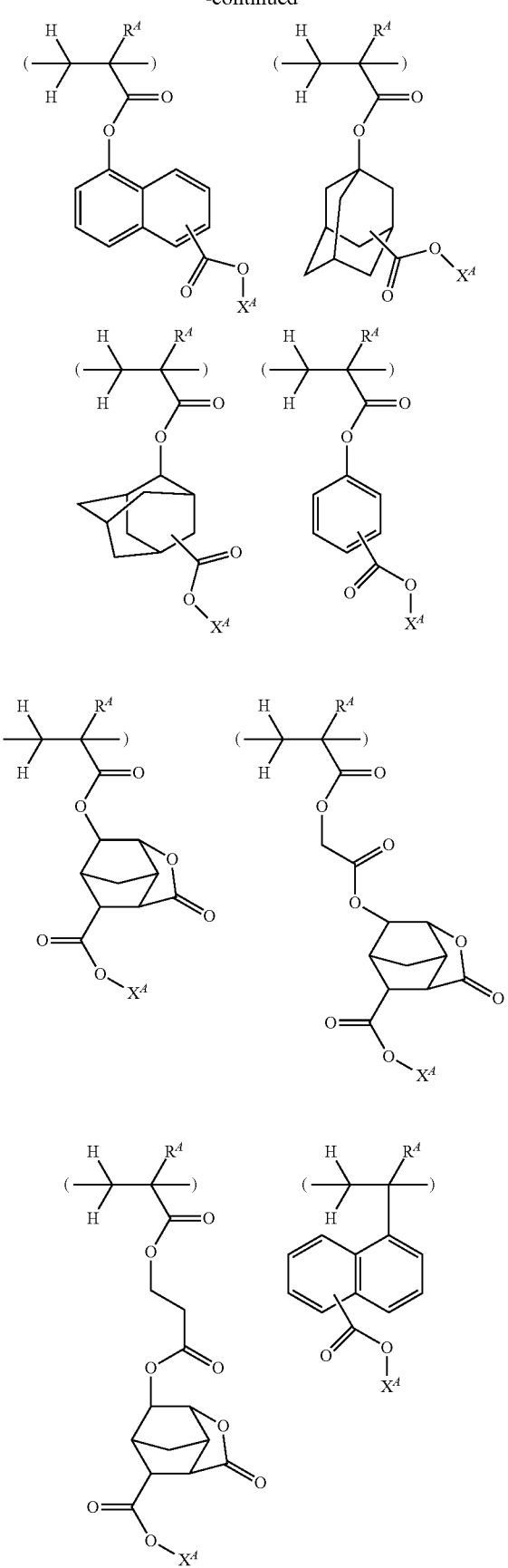

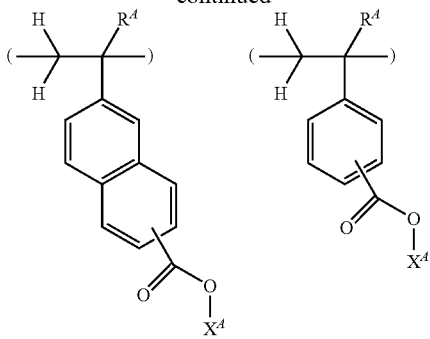

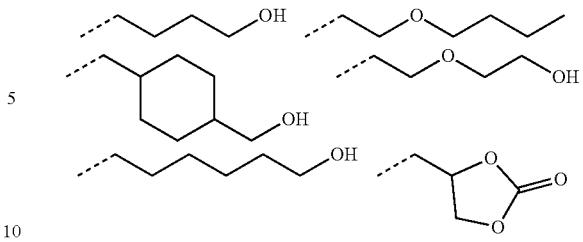

The polymer comprising recurring units having formula (a) functions such that it may be decomposed to generate carboxylic acid under the action of an acid and turn alkali soluble.

The acid labile group represented by $X^A$ may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

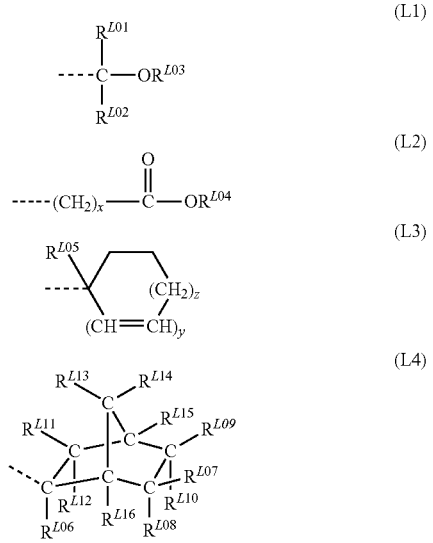

In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like, or in which a heteroatom such as oxygen intervenes between carbon atoms. Exemplary alkyl groups are as exemplified above for $R^{L01}$ and $R^{L02}$. Illustrative examples of the substituted alkyl groups are shown below.

A pair of $R^{L01}$ and $R^{L02}$, $R^{L01}$ and $R^{L03}$, or $R^{L02}$ and $R^{L03}$ may bond together to form a ring with the carbon and oxygen atom to which they are attached. A ring-forming pair of $R^{L01}$, $R^{L02}$ and $R^{L03}$ is a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (L3), $R^{L05}$ is an optionally substituted, straight, branched or cyclic $C_1$-$C_8$ alkyl group or an optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-pentyl, n-pentyl, n-hexyl, cyclopentyl and cyclohexyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Letter y is equal to 0 or 1, z is an integer of 0 to 3, and 2y+z is equal to 2 or 3.

In formula (L4), $R^{L06}$ is an optionally substituted, straight, branched or cyclic $C_1$-$C_8$ alkyl group or an optionally substituted $C_6$-$C_{20}$ aryl group. Examples of these groups are the same as exemplified for $R^{L05}$. $R^{L07}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or the like. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). A ring-forming pair of $R^{L07}$ to $R^{L16}$ is a $C_1$-$C_{15}$ divalent hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following groups.

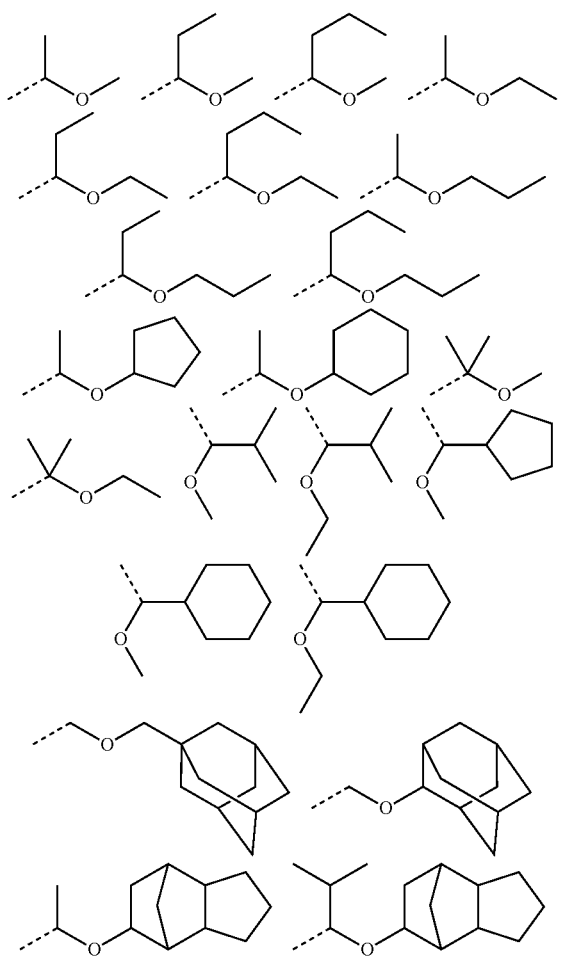

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

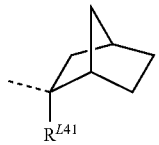
(L4-1)

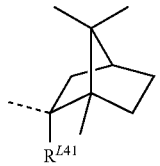
(L4-2)

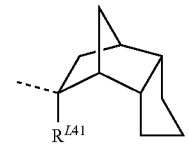
(L4-3)

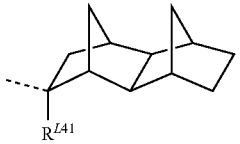
(L4-4)

In formulas (L4-1) to (L4-4), the broken line denotes a bonding site and direction. $R^{L41}$ is each independently a monovalent hydrocarbon group, typically a $C_1$-$C_{10}$ straight, branched or cyclic alkyl group, such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When the acid labile group $X^A$ is of formula (L4), a plurality of stereoisomers may be included.

For example, the formula (L4-3) represents one or a mixture of two selected from groups having the following formulas (L4-3-1) and (L4-3-2).

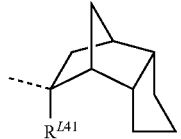
(L4-3-1)

-continued (L4-3-2)
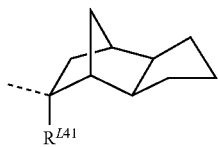

$R^{L41}$ is as defined above.

Similarly, the formula (L4-4) represents one or a mixture of two or more selected from groups having the following formulas (L4-4-1) to (L4-4-4).

(L4-4-1)
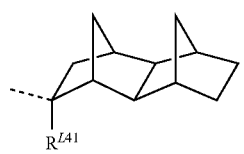

(L4-4-2)
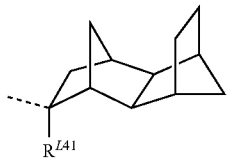

(L4-4-3)
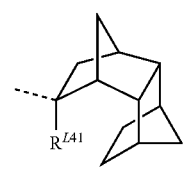

(L4-4-4)
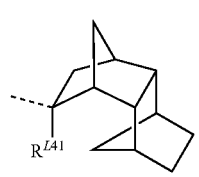

$R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)
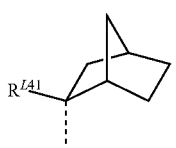

(L4-2-endo)
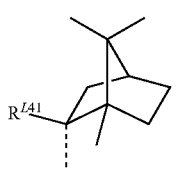

(L4-3-endo)

(L4-4-endo)

$R^{L41}$ is as defined above.

Illustrative examples of the acid labile group of formula (L4) are given below.

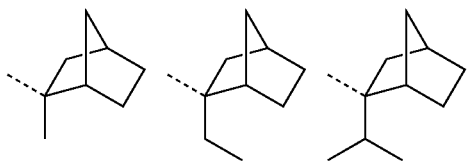
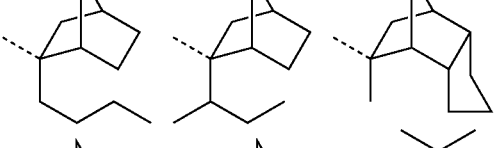
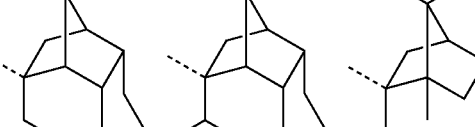
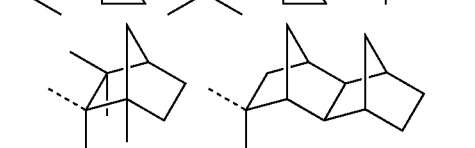
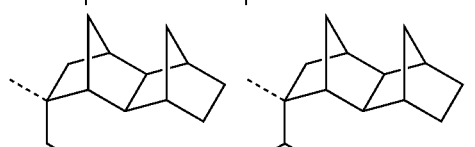
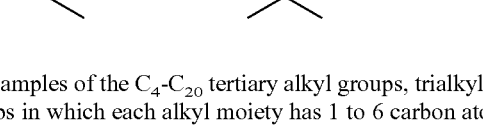

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups, $X^A$, are as exemplified for $R^{L04}$.

Illustrative examples of the recurring units of formula (a) are given below, but not limited thereto. $R^A$ is as defined above.

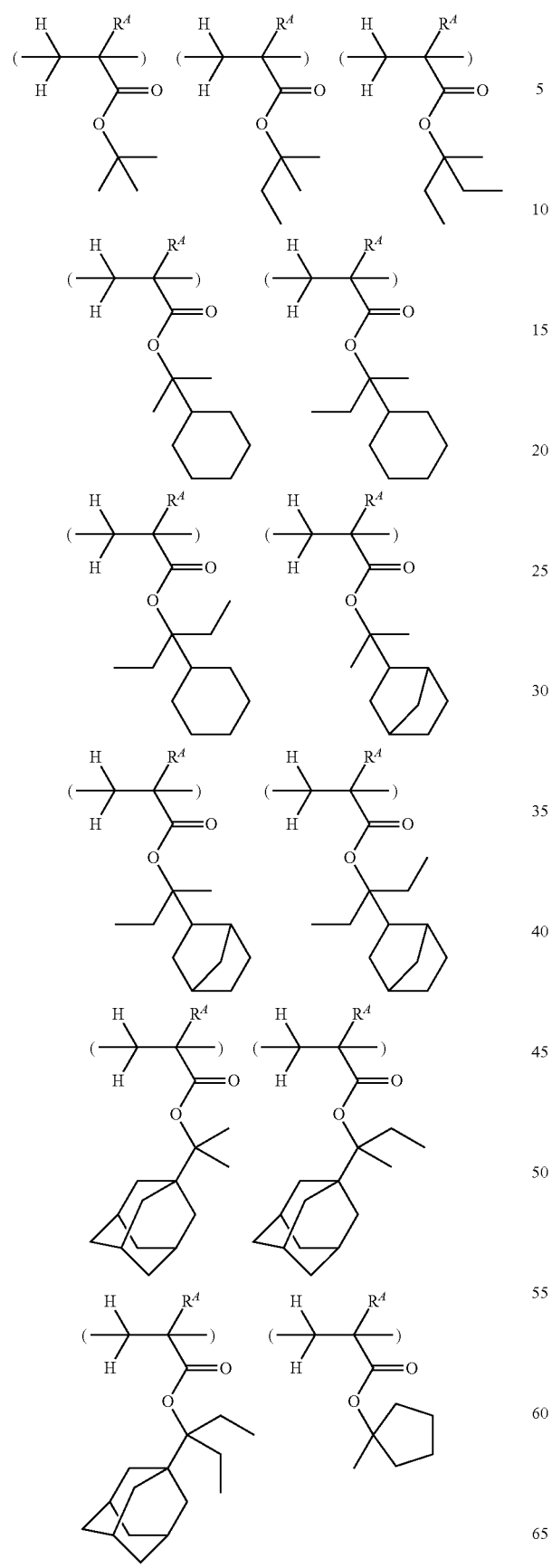
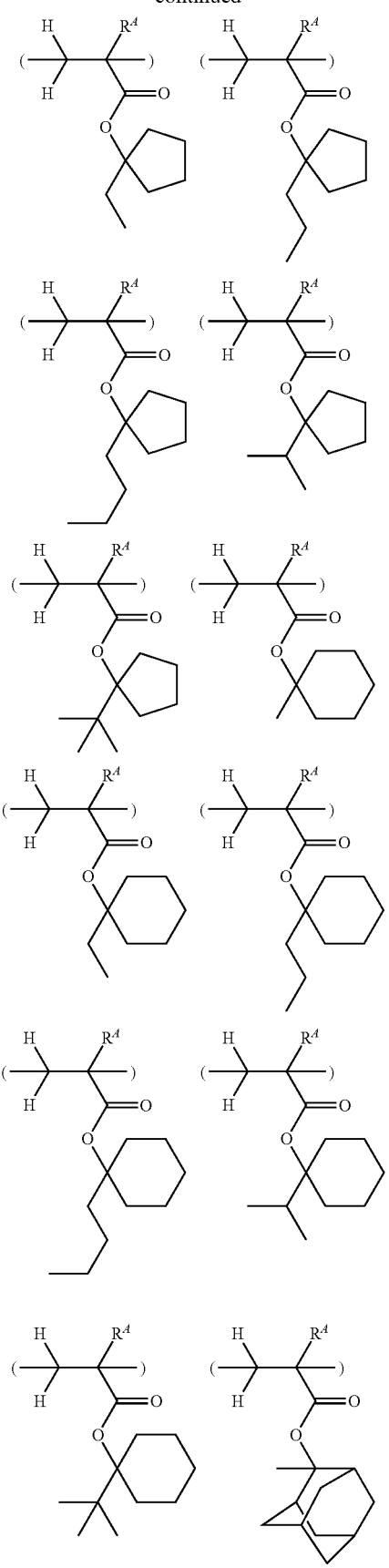

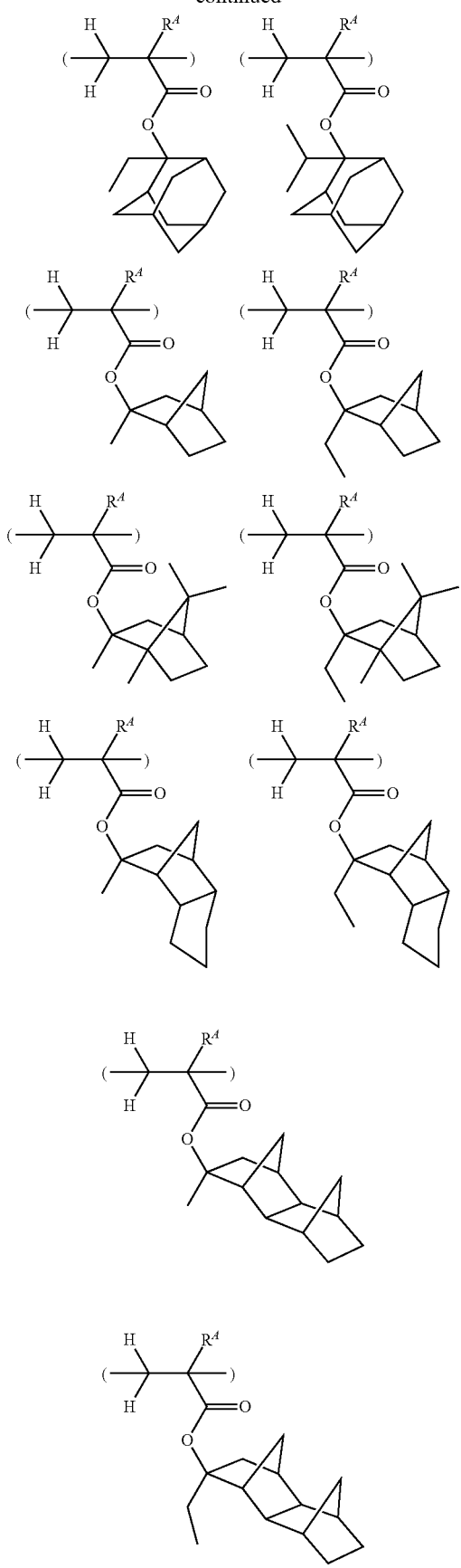
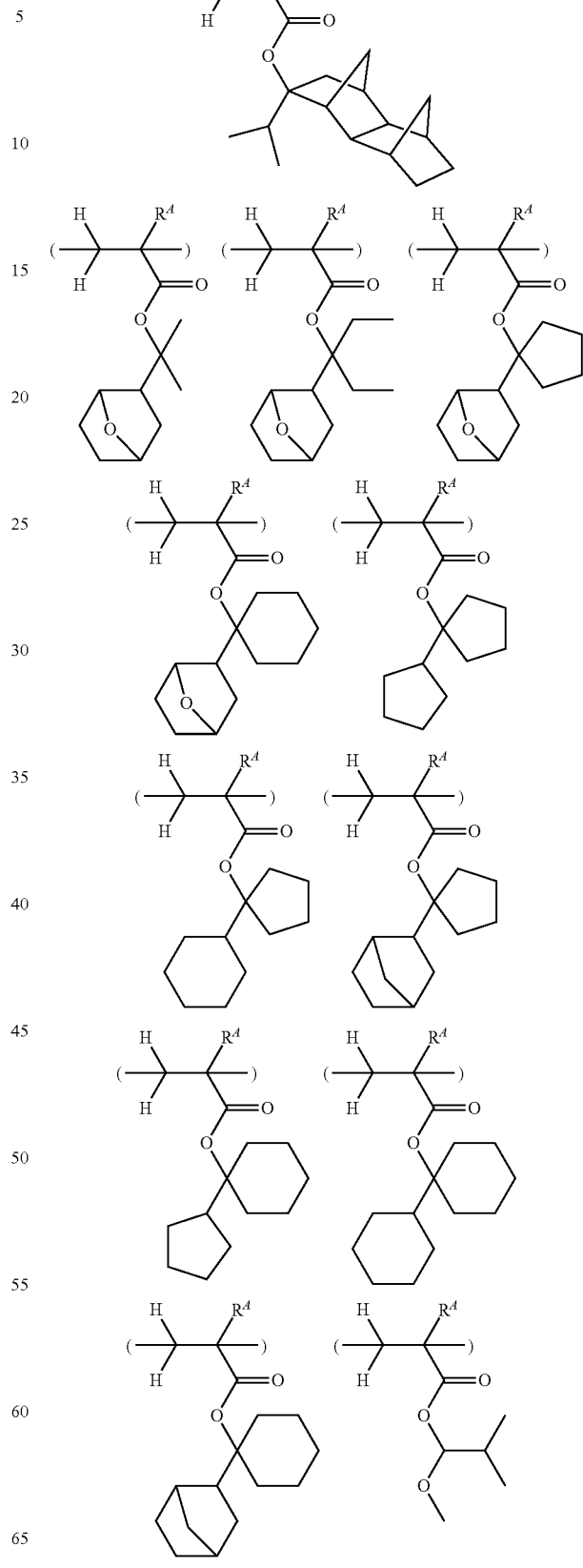

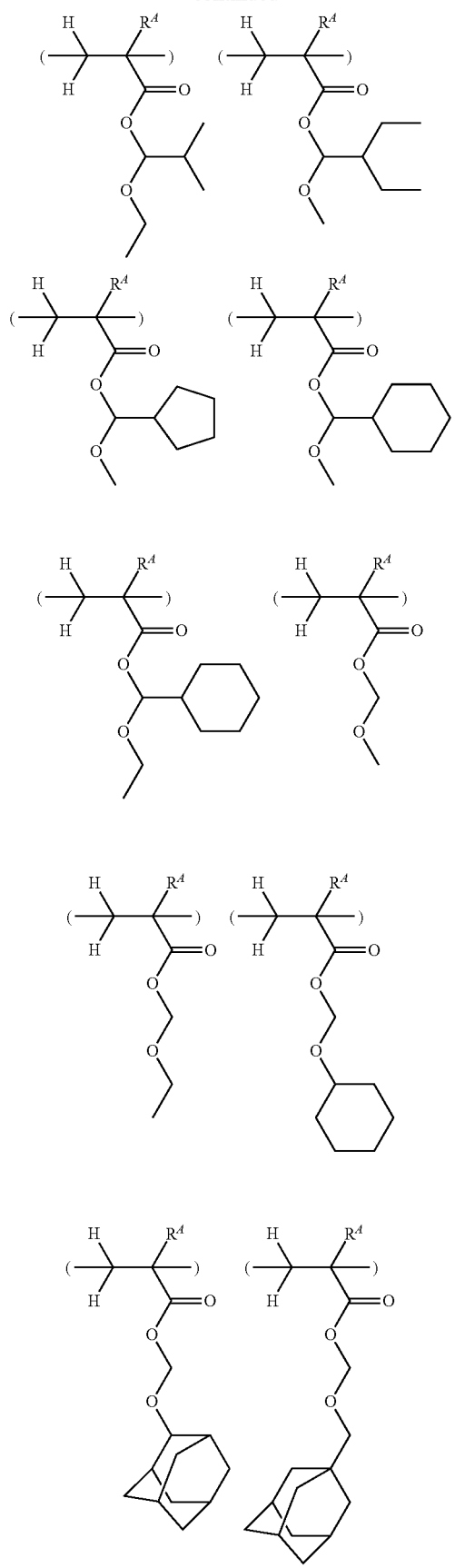
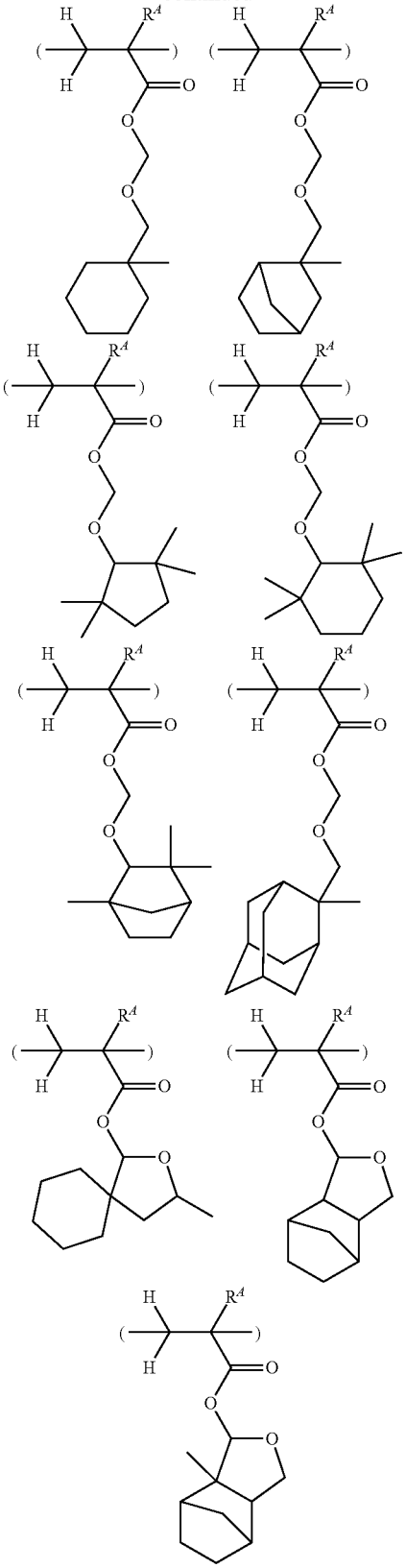
The above examples correspond to those units of formula (a) wherein $Z^A$ is a single bond. Where $Z^A$ is other than a single bond, a combination with a similar acid labile group is possible. Thus examples of the recurring units of formula (a) wherein $Z^A$ is other than a single bond are as illustrated above.

Preferably, the polymer further comprises recurring units having the formula (b):

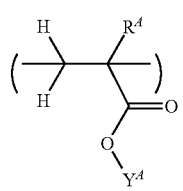

wherein $R^A$ is as defined above, and $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

Illustrative examples of the recurring units of formula (b) are given below, but not limited thereto. $R^A$ is as defined above.

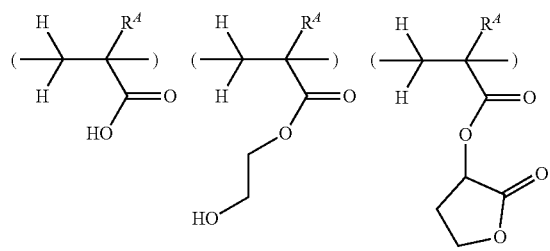

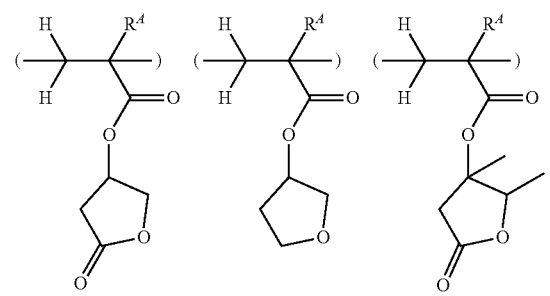

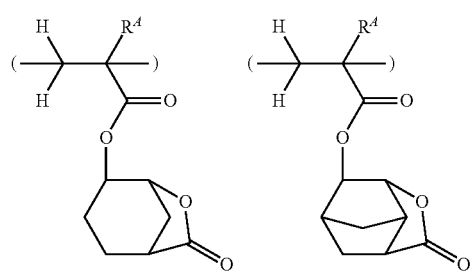

-continued

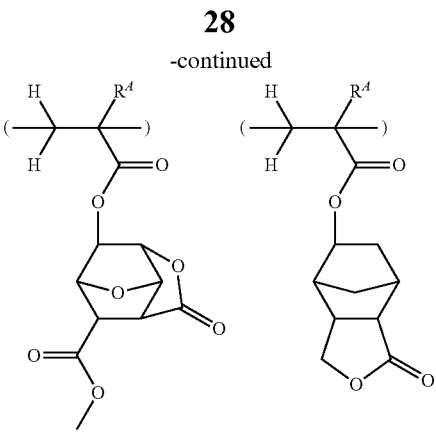

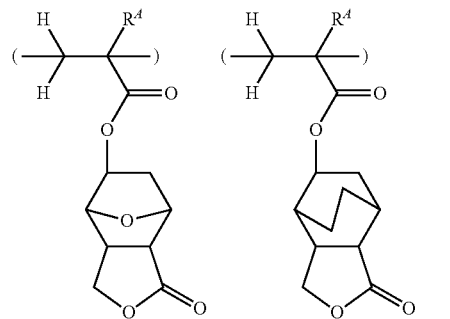

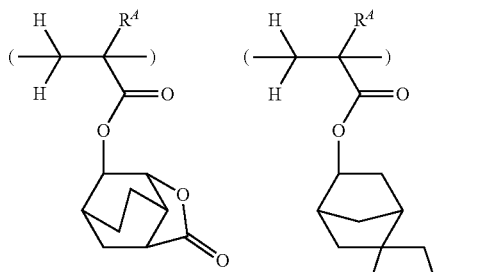

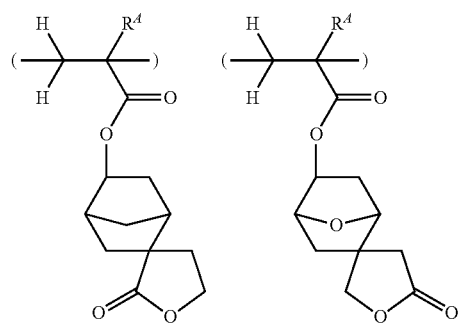

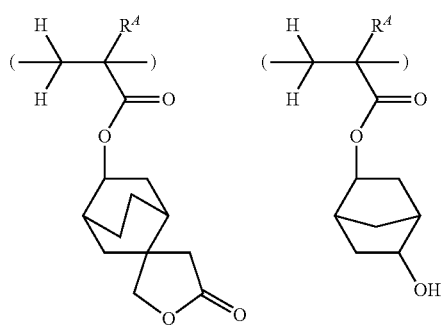

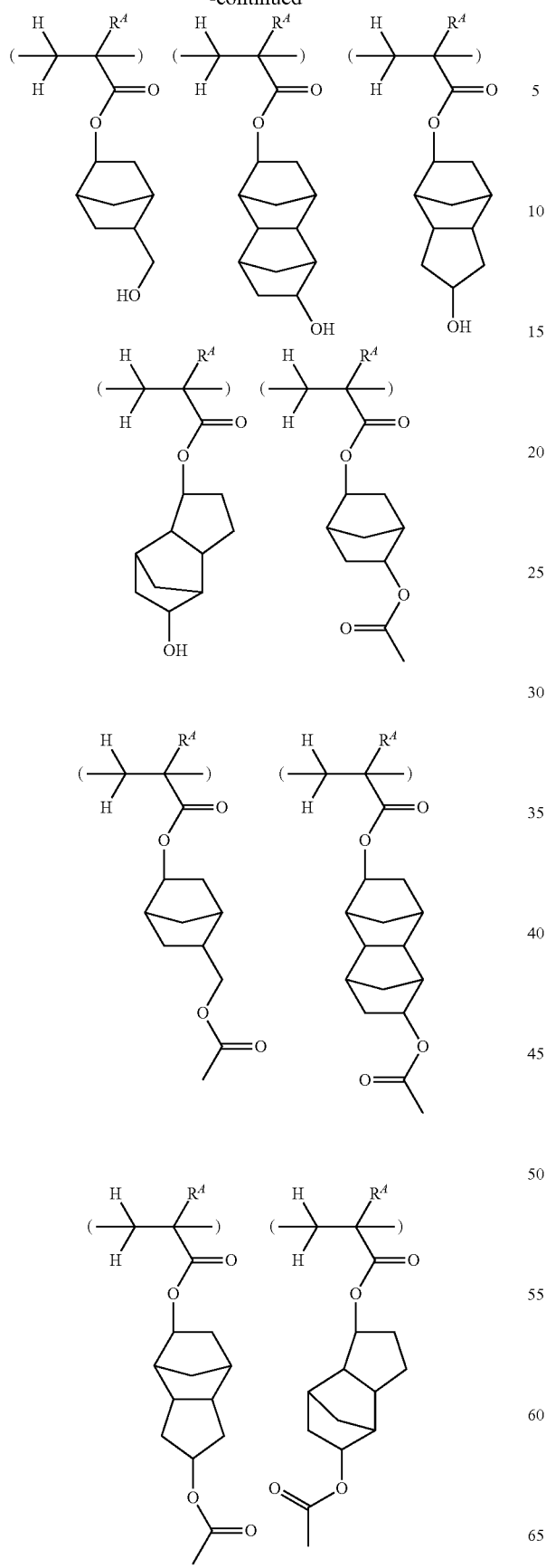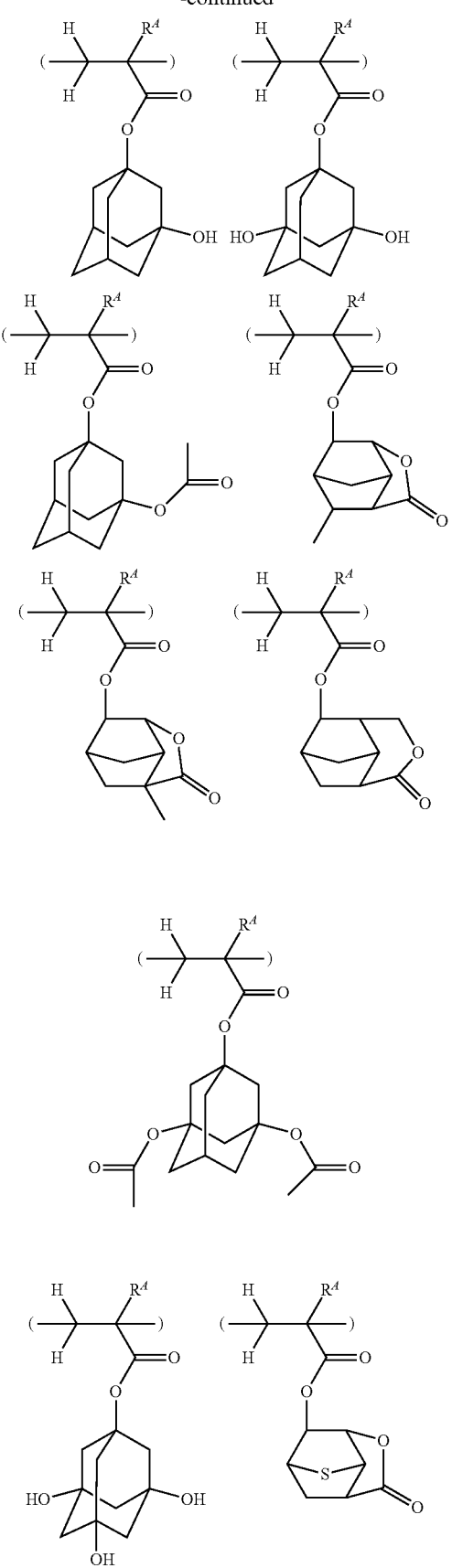

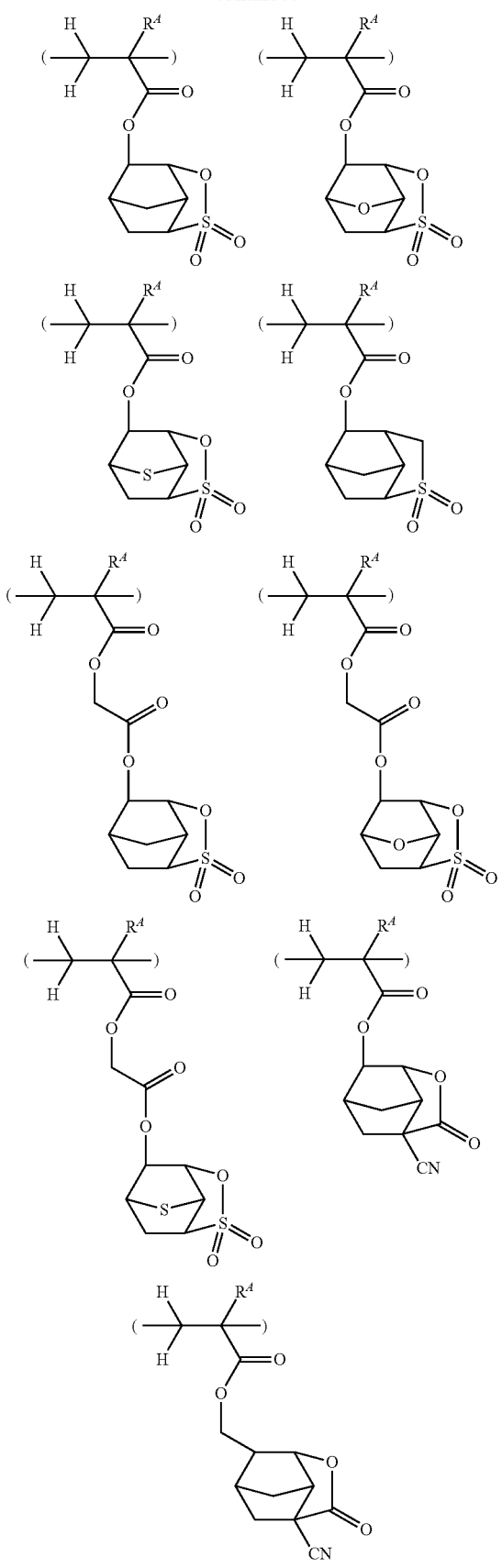
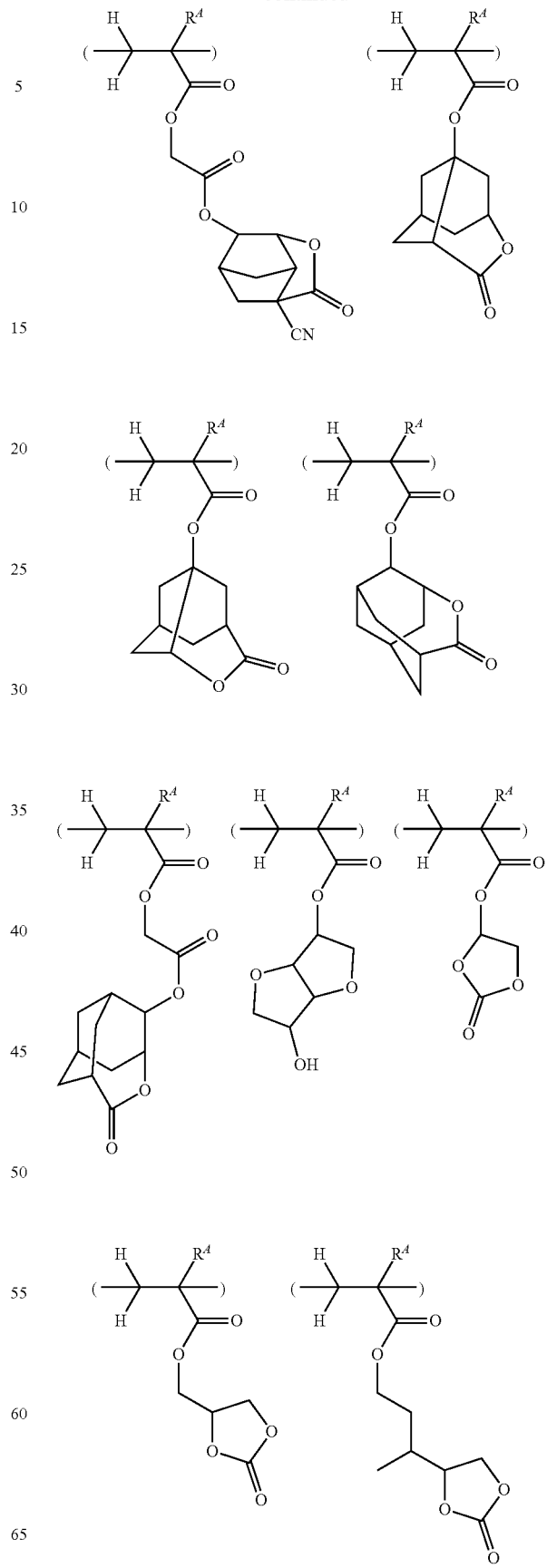

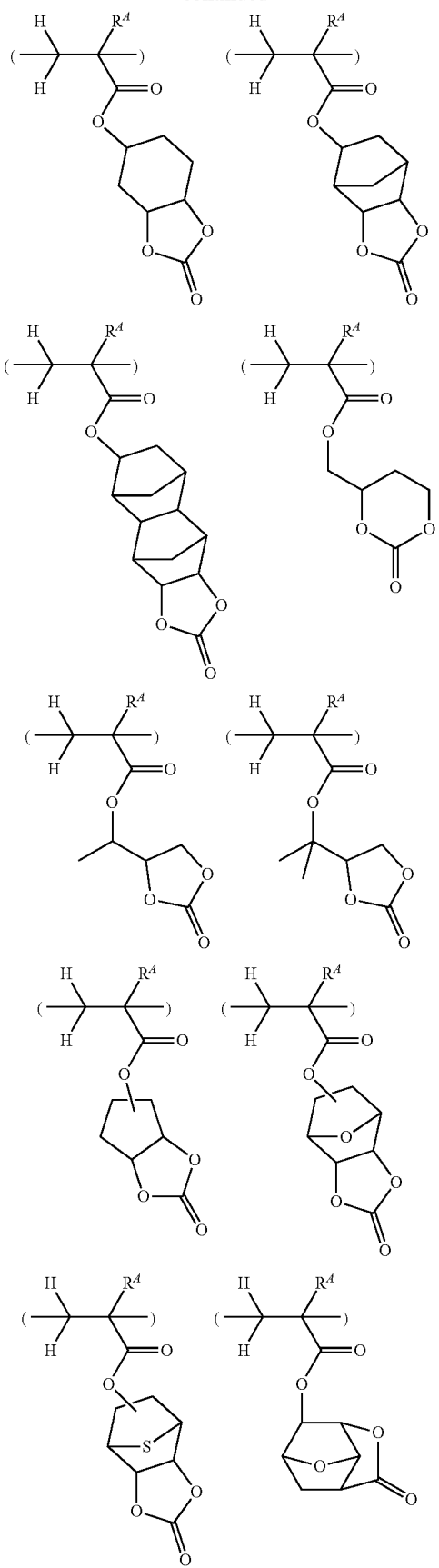
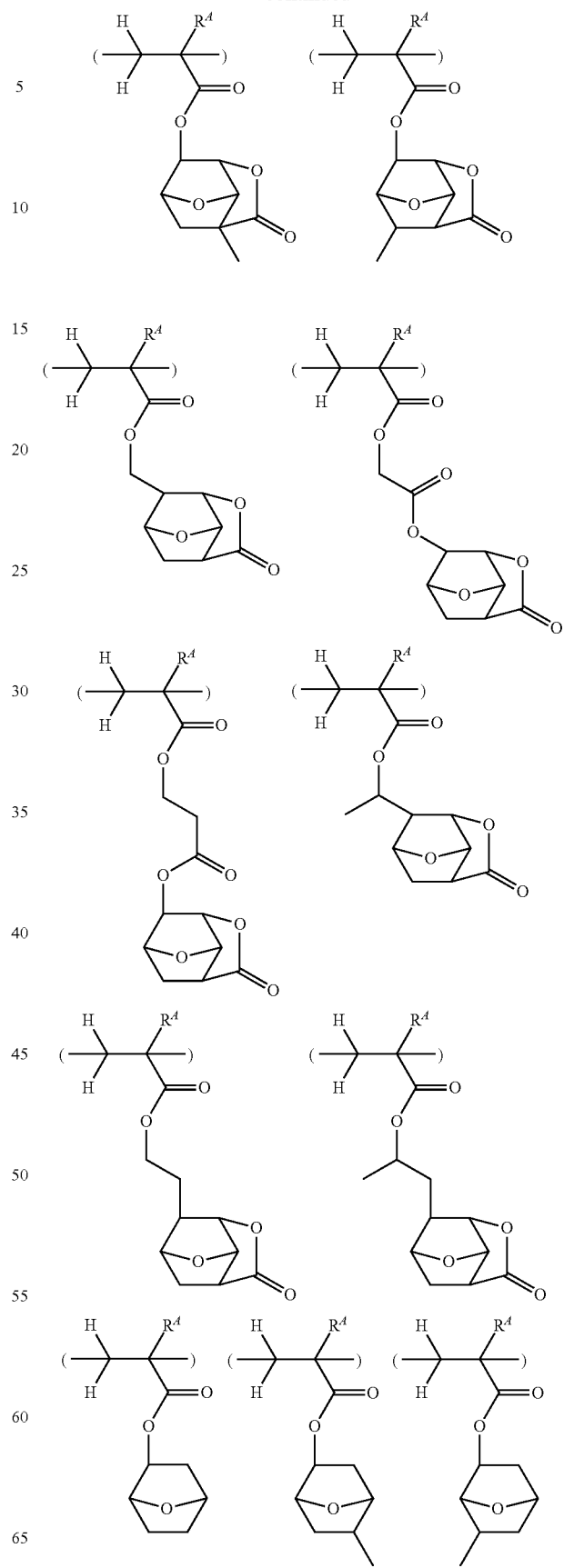

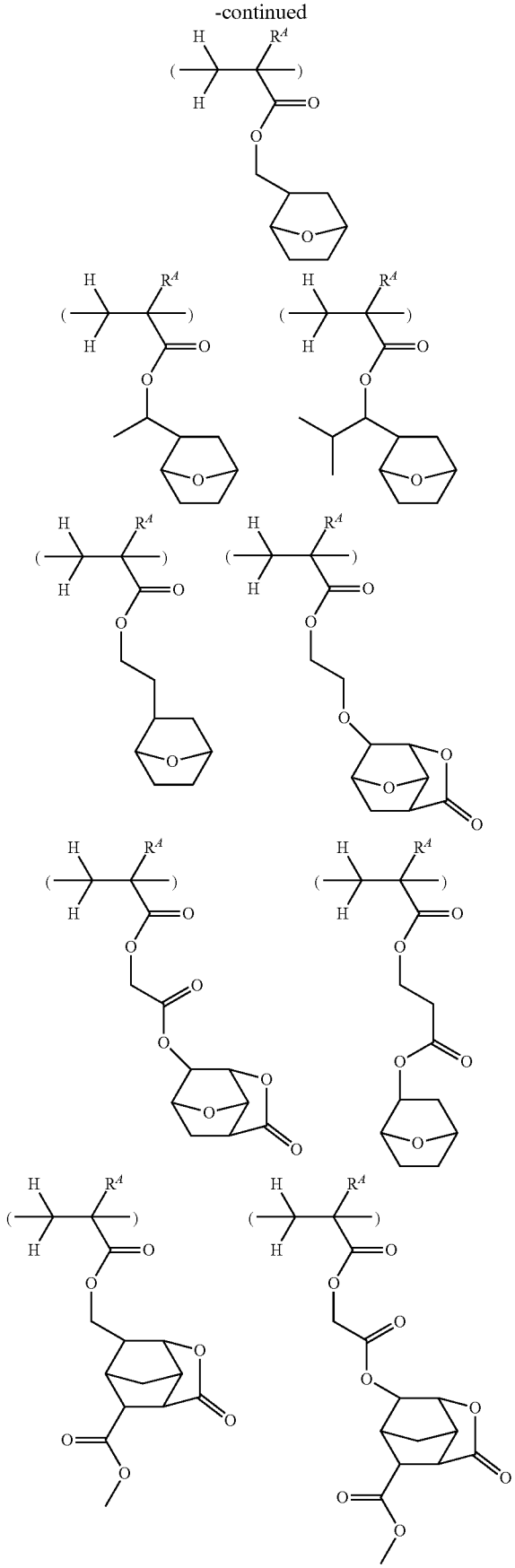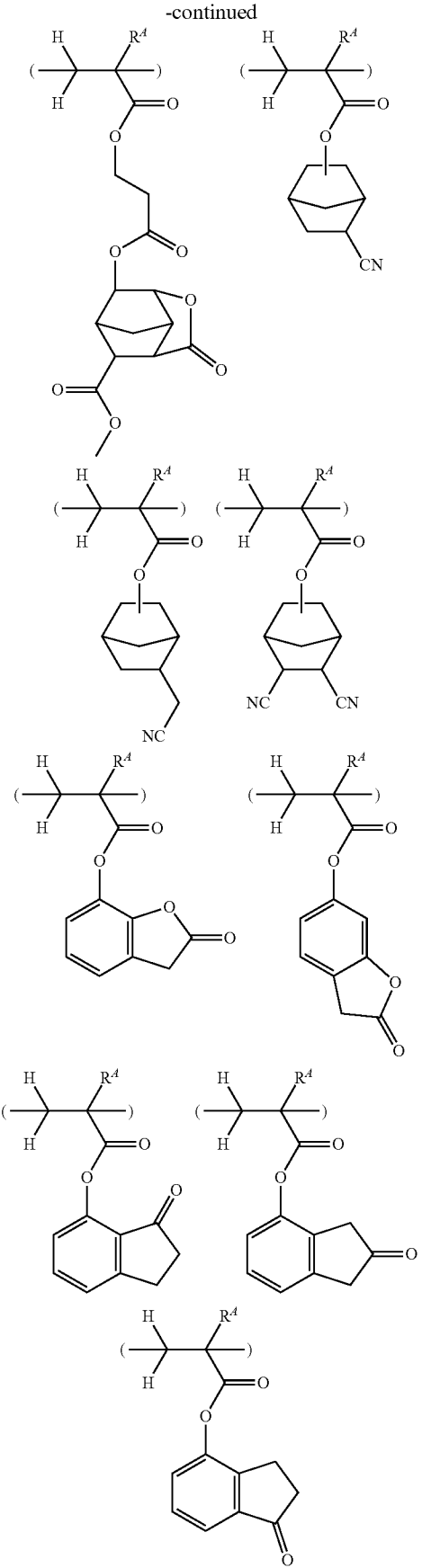

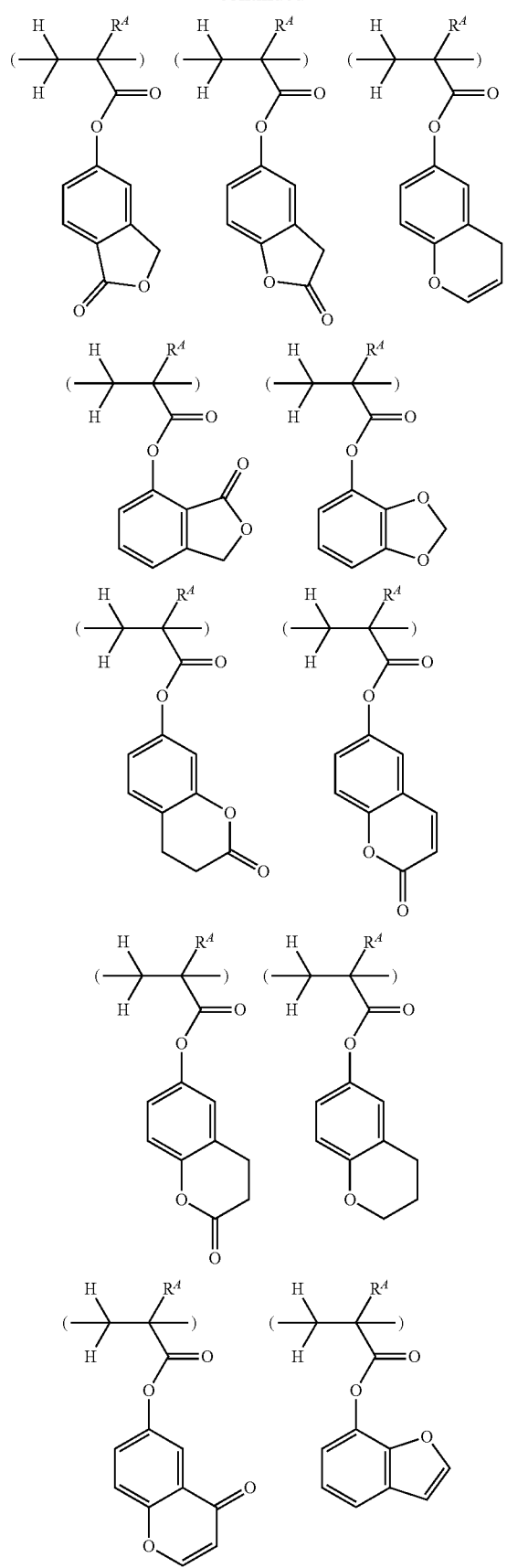
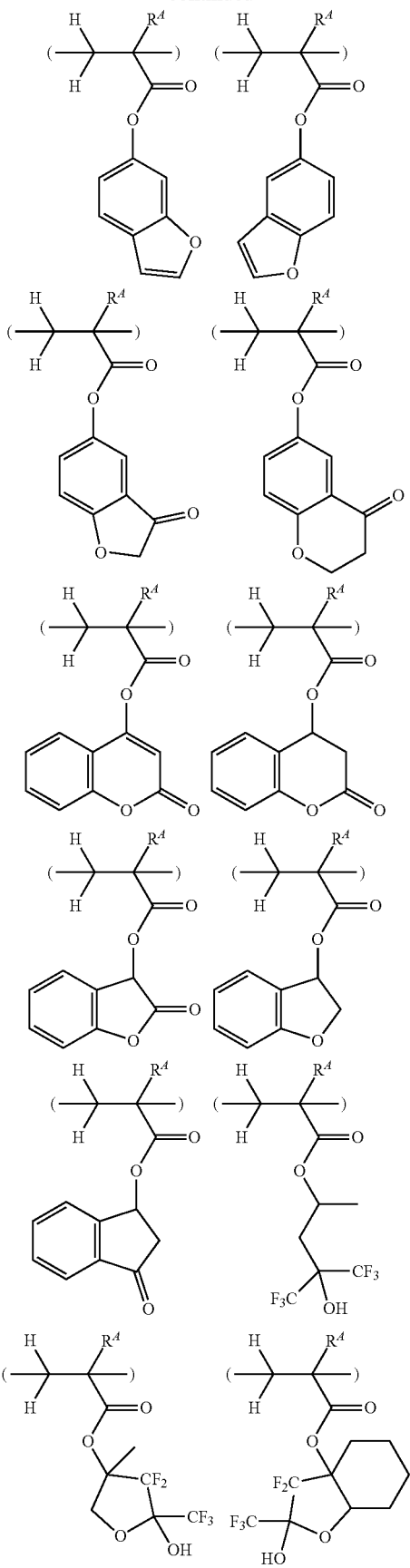

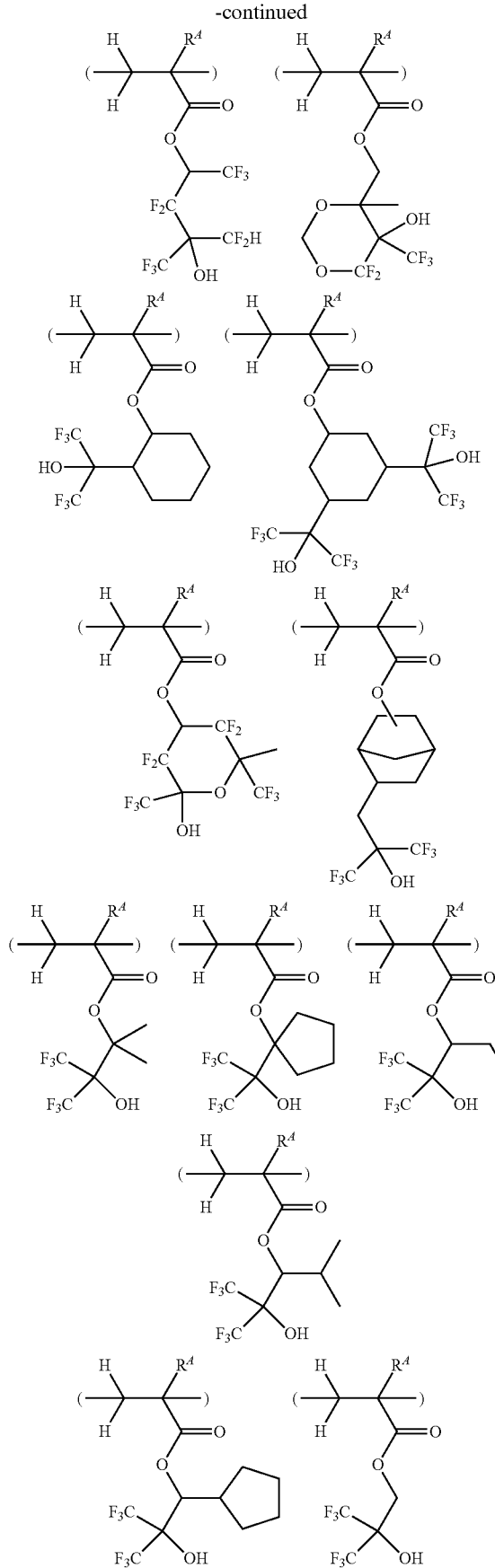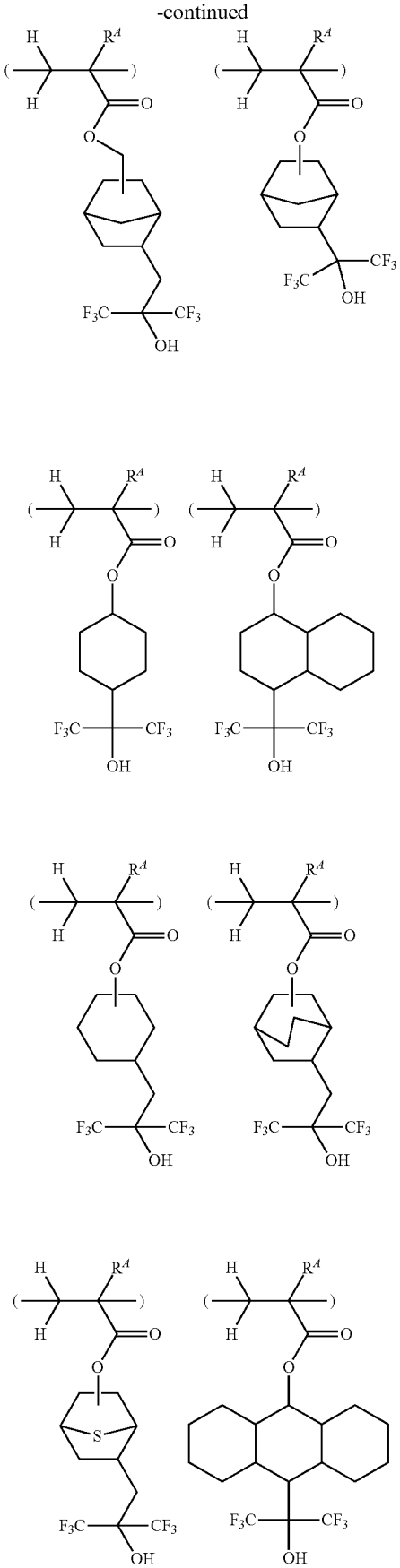

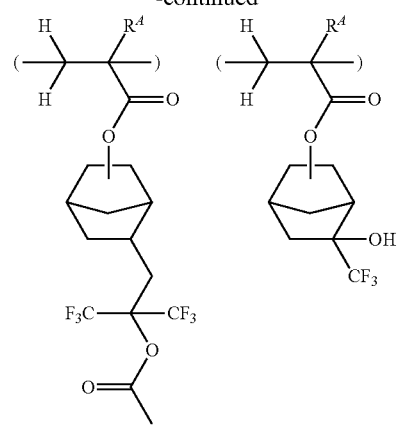
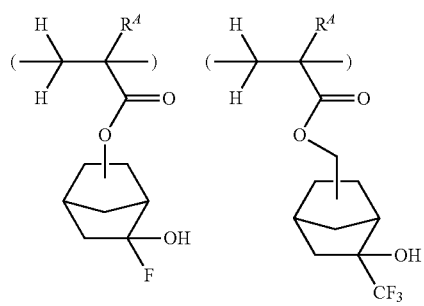
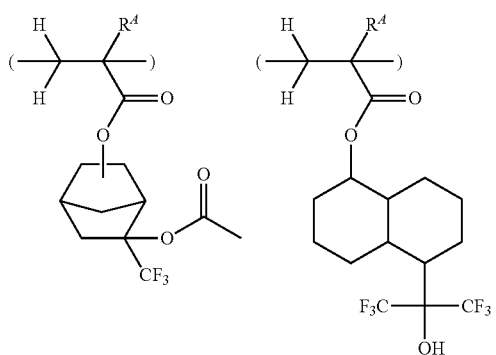
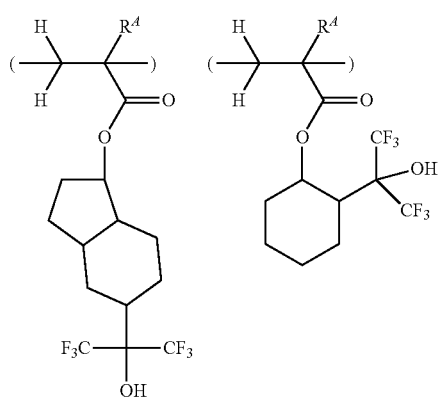
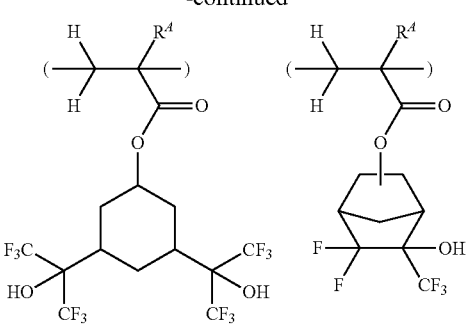
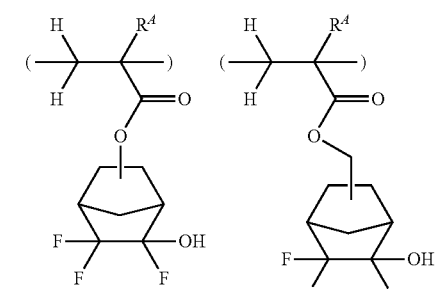
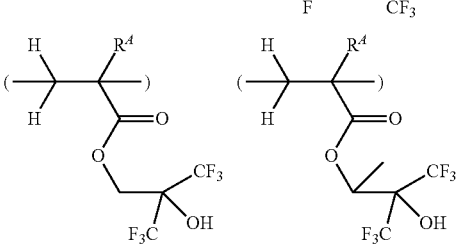
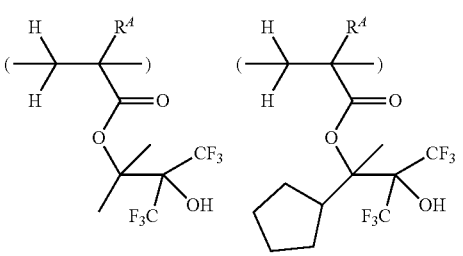
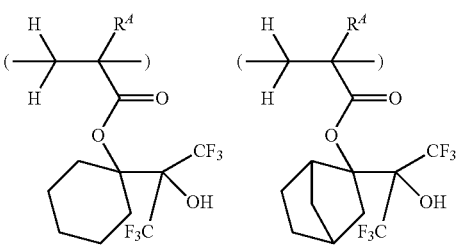
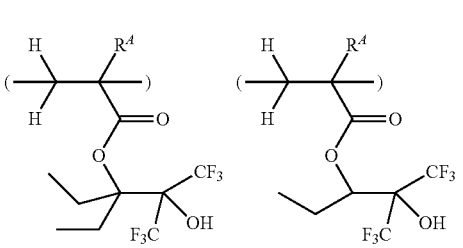

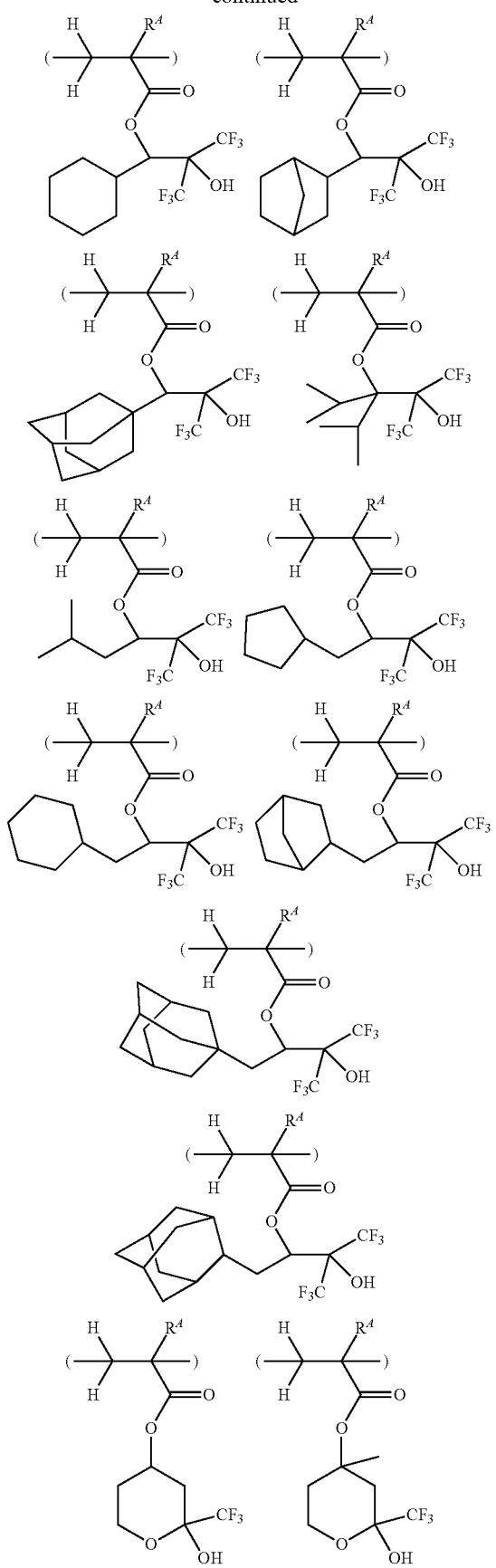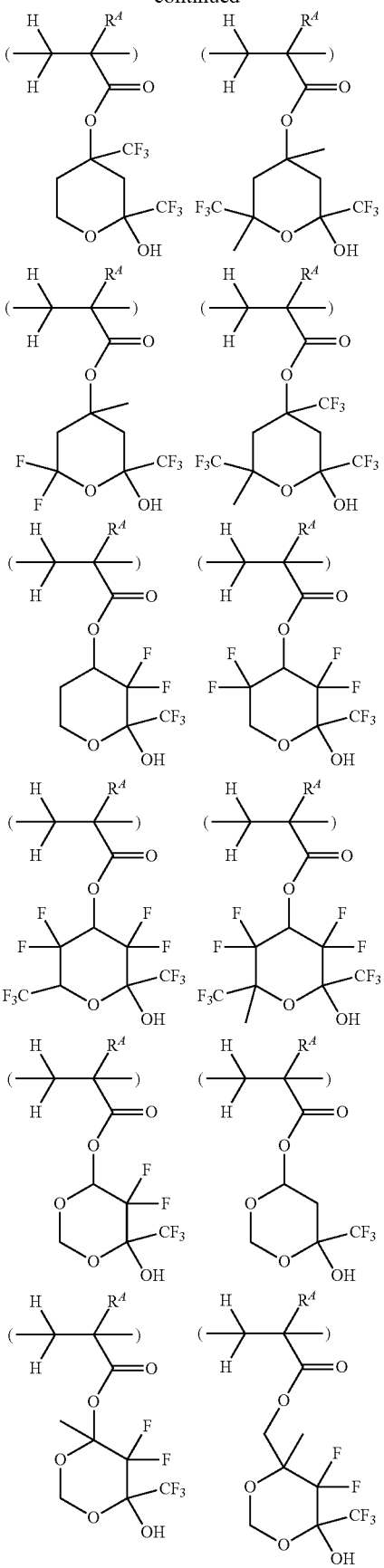

-continued
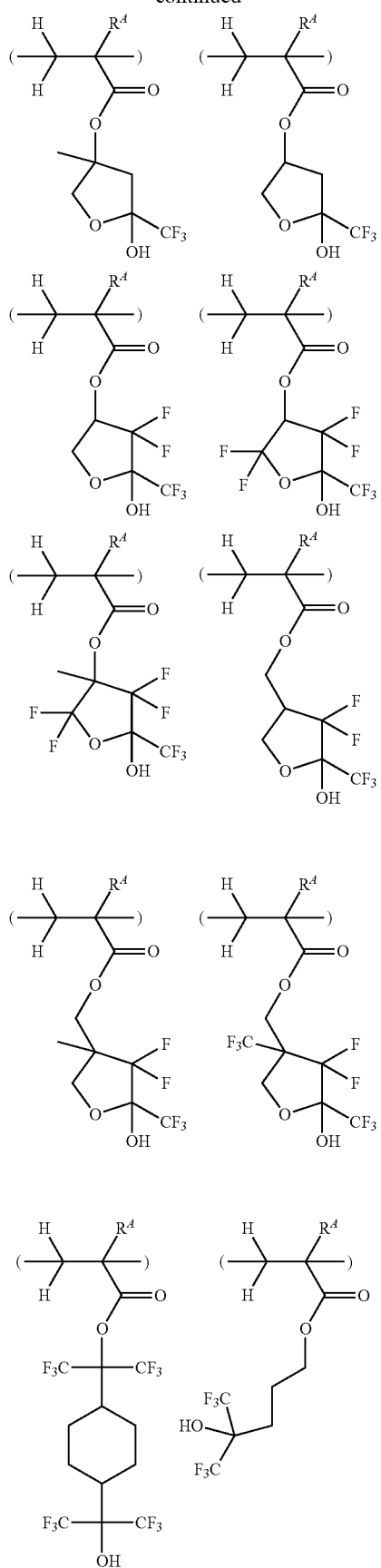
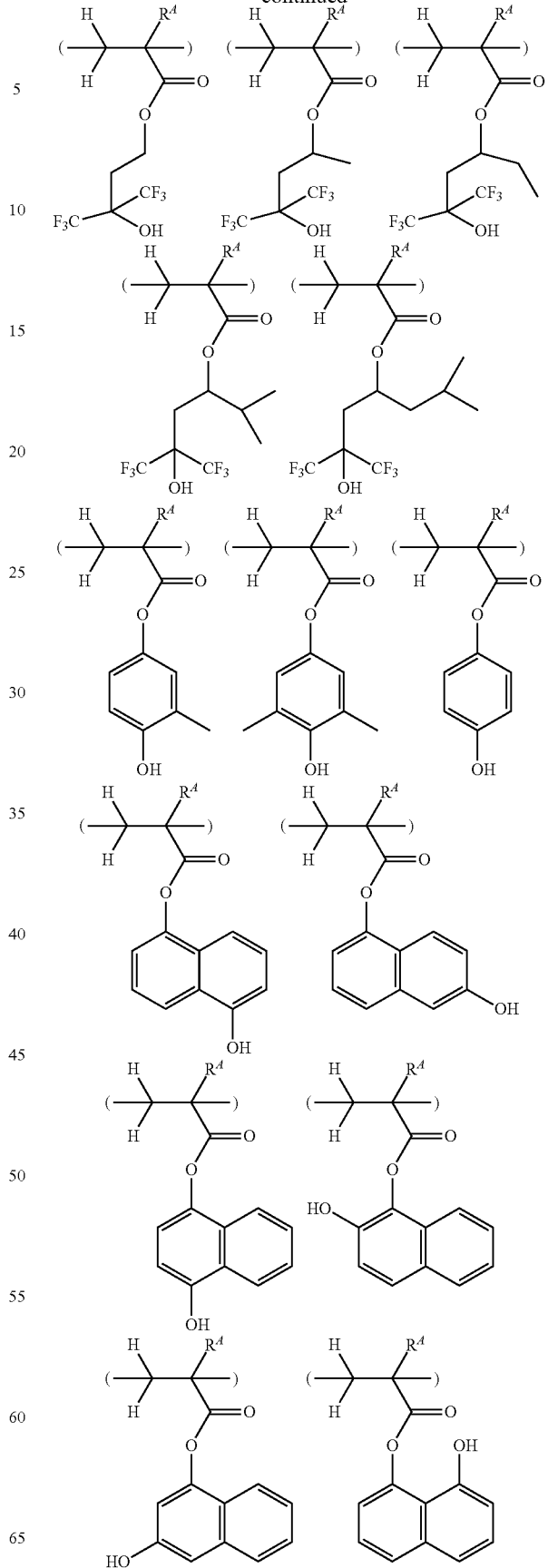

-continued

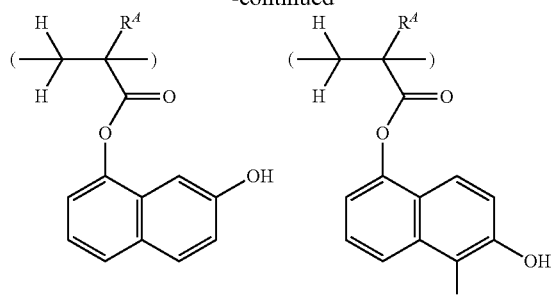
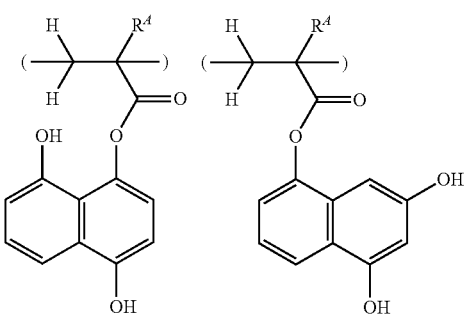
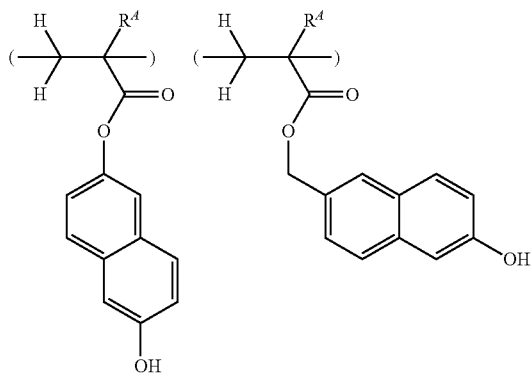
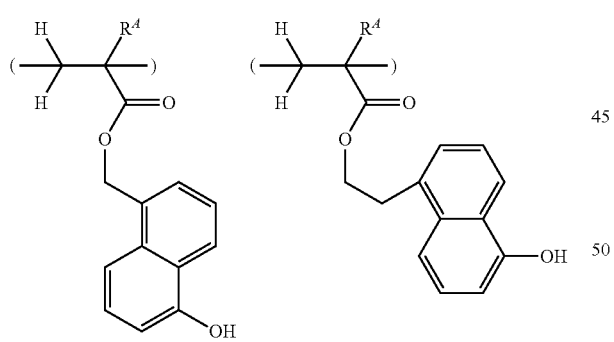
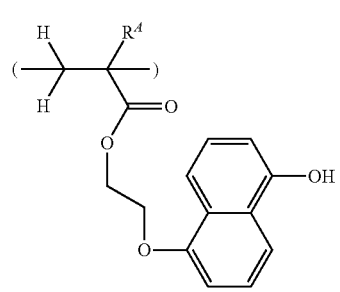

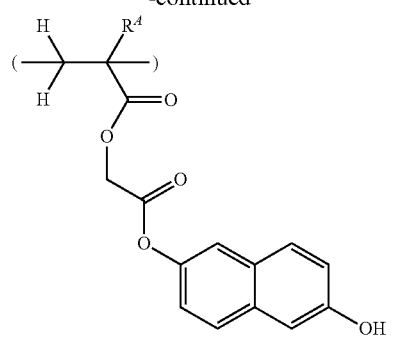
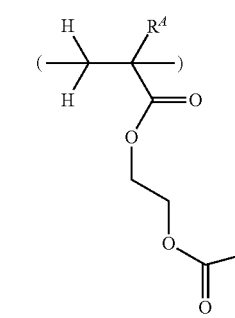
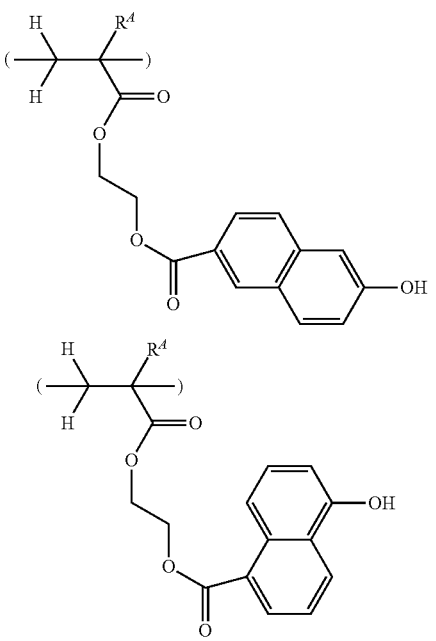

Among the recurring units of formula (b), units having lactone ring as the polar group are most preferred.

While the polymer is characterized by comprising recurring units having formula (a) and preferably recurring units having formula (b), it may further comprise recurring units of at least one type selected from recurring units having the formulae (c1) and (c2).

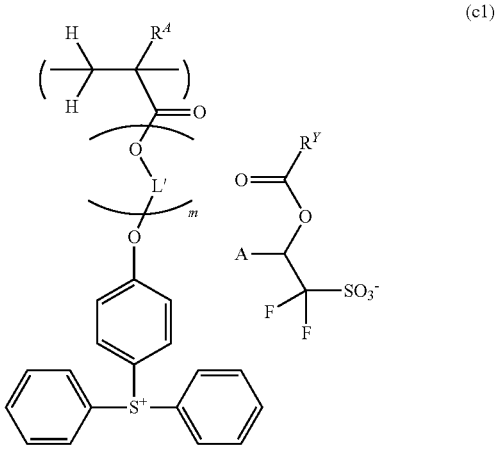

(c1)

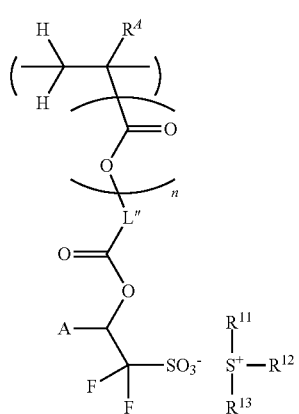

(c2)

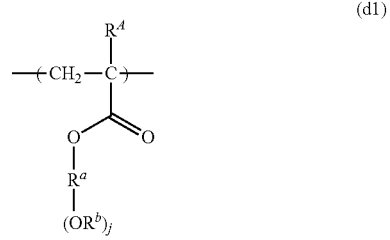

(d1)

Herein $R^A$ is as defined above. $R^{11}$, $R^{12}$ and $R^{13}$ are each independently a $C_1$-$C_{20}$ straight, branched or cyclic monovalent hydrocarbon group which may contain a heteroatom. L' is a $C_2$-$C_5$ alkylene group. $R^Y$ is a $C_1$-$C_{20}$ straight, branched or cyclic monovalent hydrocarbon group which may contain a heteroatom. A is hydrogen or trifluoromethyl. L" is a single bond, or a $C_1$-$C_{20}$ straight, branched or cyclic divalent hydrocarbon group which may contain a heteroatom, m is 0 or 1, and n is 0 or 1, with the proviso that n=0 when L" is a single bond.

Suitable groups L' include ethylene, propylene and butylene. A is preferably trifluoromethyl. Examples of the monovalent hydrocarbon groups $R^Y$, $R^{11}$, $R^{12}$ and $R^{13}$ are as exemplified above for $R^1$ to $R^3$ in formula (1). Examples of the divalent hydrocarbon group L" include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether bond, thioether bond, ester bond, sulfonic acid ester bond, carbonate bond, carbamate bond, lactone ring, sultone ring, carboxylic acid anhydride or haloalkyl radical.

Exemplary structures of the anion moiety in formula (c1) include those described in JP-A 2010-113209 and JP-A 2007-145797. Exemplary structures of the anion moiety in formula (c2) wherein A is hydrogen include those described in JP-A 2010-116550, and exemplary structures of the anion moiety in formula (c2) wherein A is trifluoromethyl include those described in JP-A 2010-077404.

The polymer may further comprise recurring units of a structure having a hydroxyl group protected with an acid labile group. These recurring units are not particularly limited as long as at least one structure having a protected hydroxyl group is included and under the action of acid, the protective group is decomposed to generate a hydroxyl group. Units having the formula (d1) are preferred.

In formula (d1), $R^A$ is as defined above, $R^a$ is a $C_1$-$C_{30}$ straight, branched or cyclic, di- to penta-valent hydrocarbon group which may contain a heteroatom, $R^b$ is an acid labile group, and j is an integer of 1 to 4.

Examples of the recurring units having formula (d1) are shown below, but not limited thereto. $R^A$ and $R^b$ are as defined above.

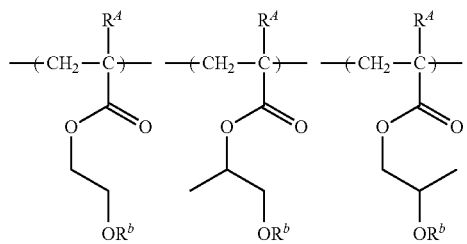

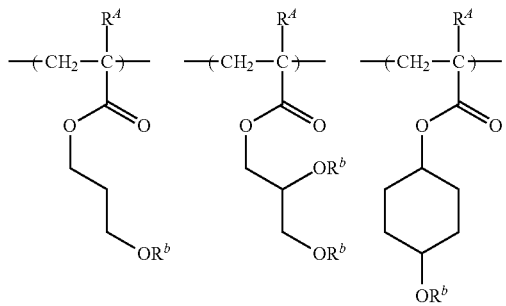

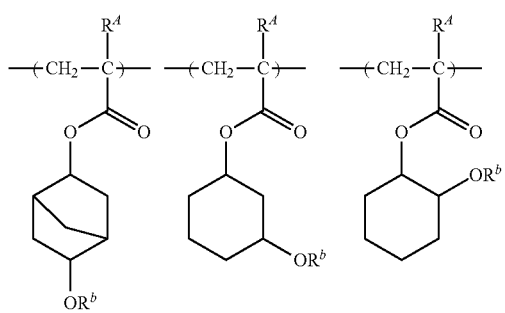

51
-continued
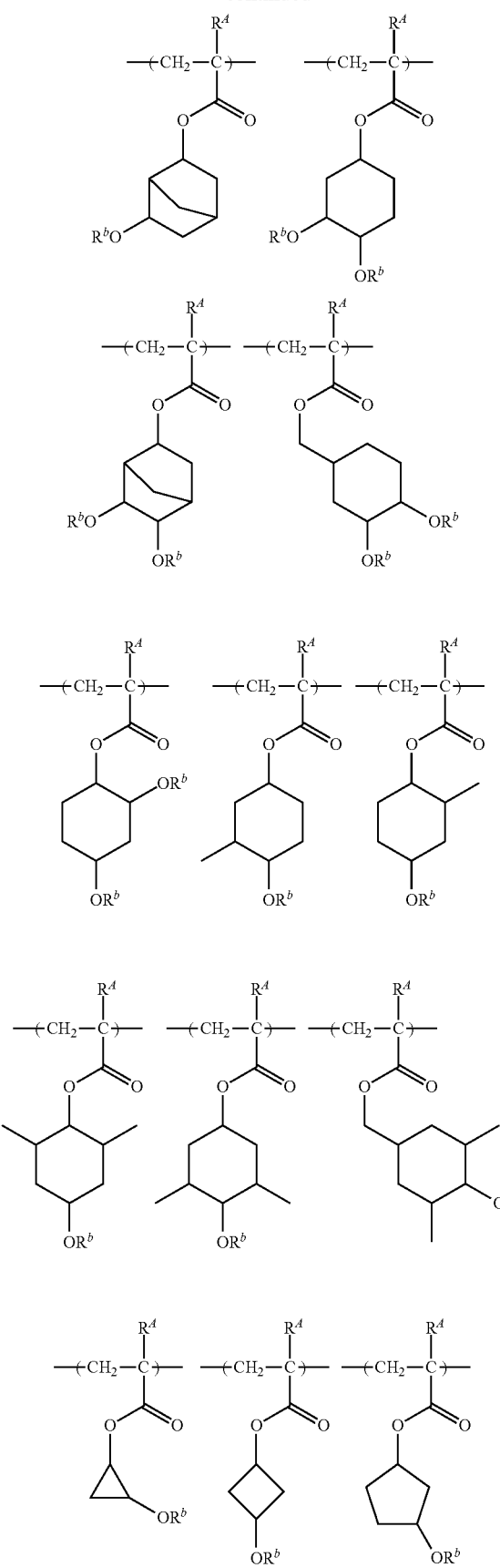
52
-continued
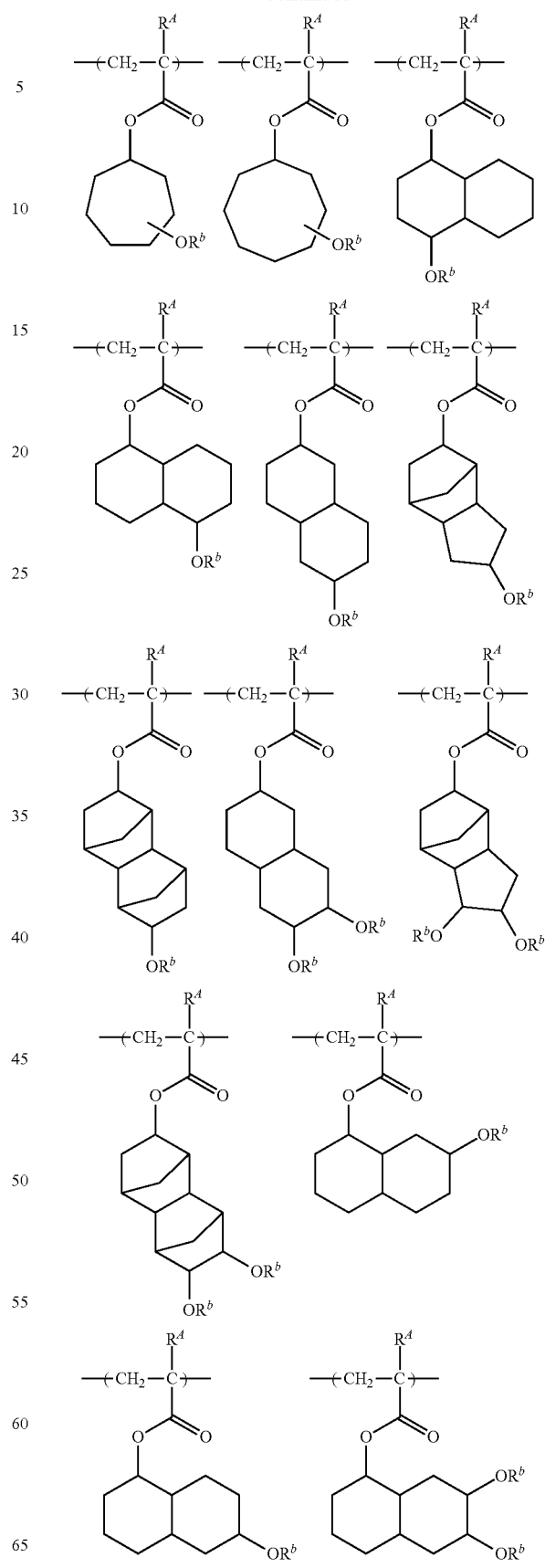

-continued
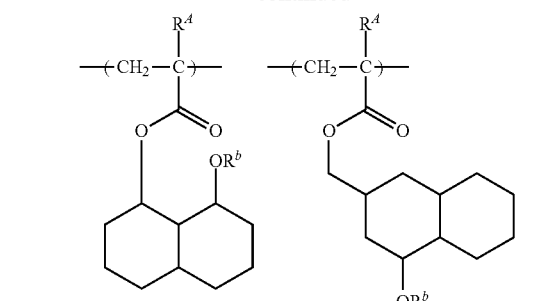
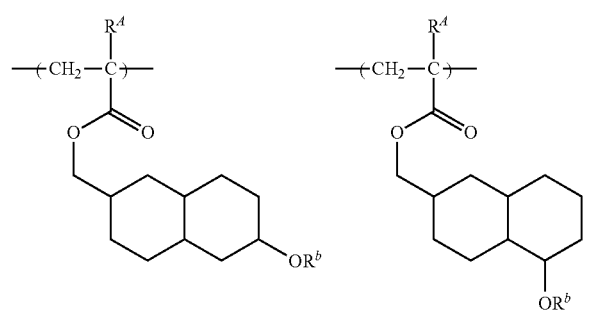
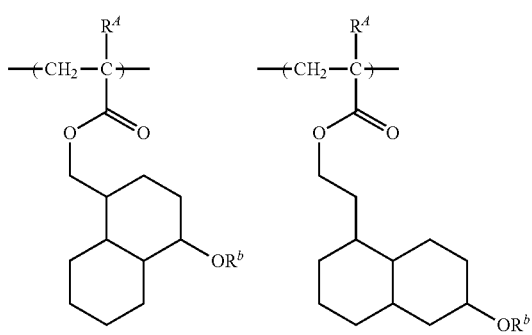
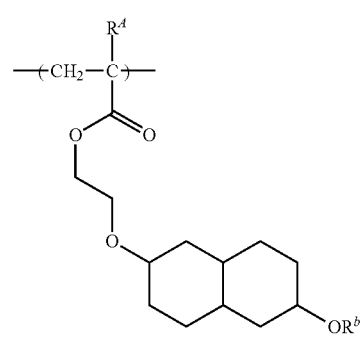
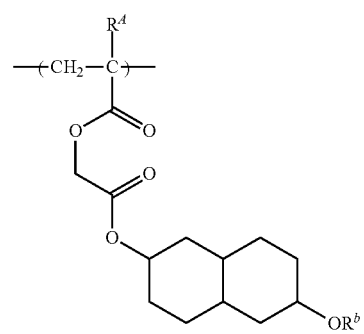
-continued
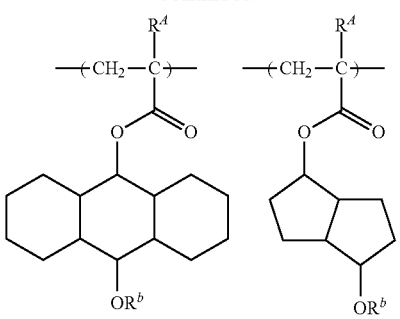
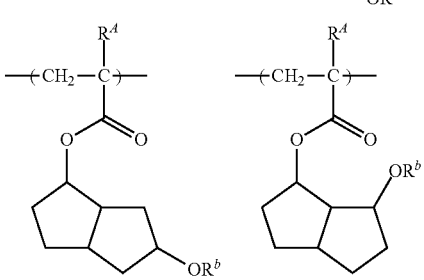
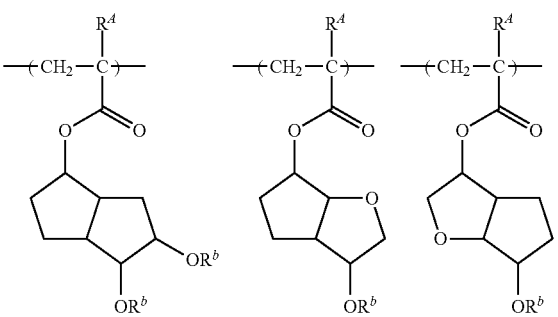
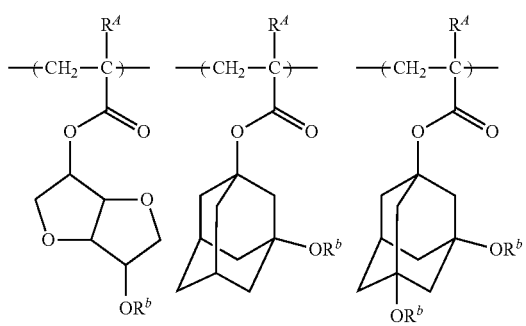
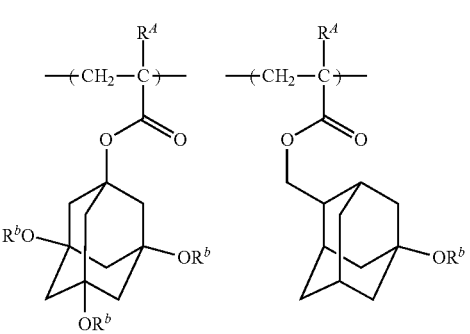

-continued

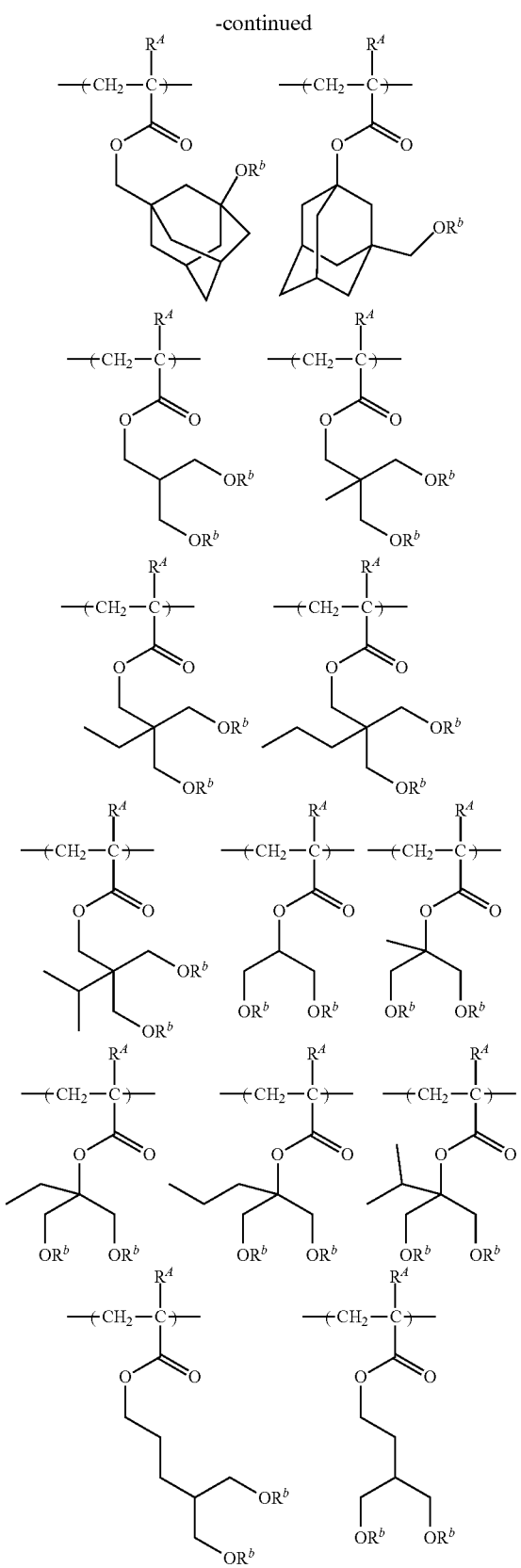

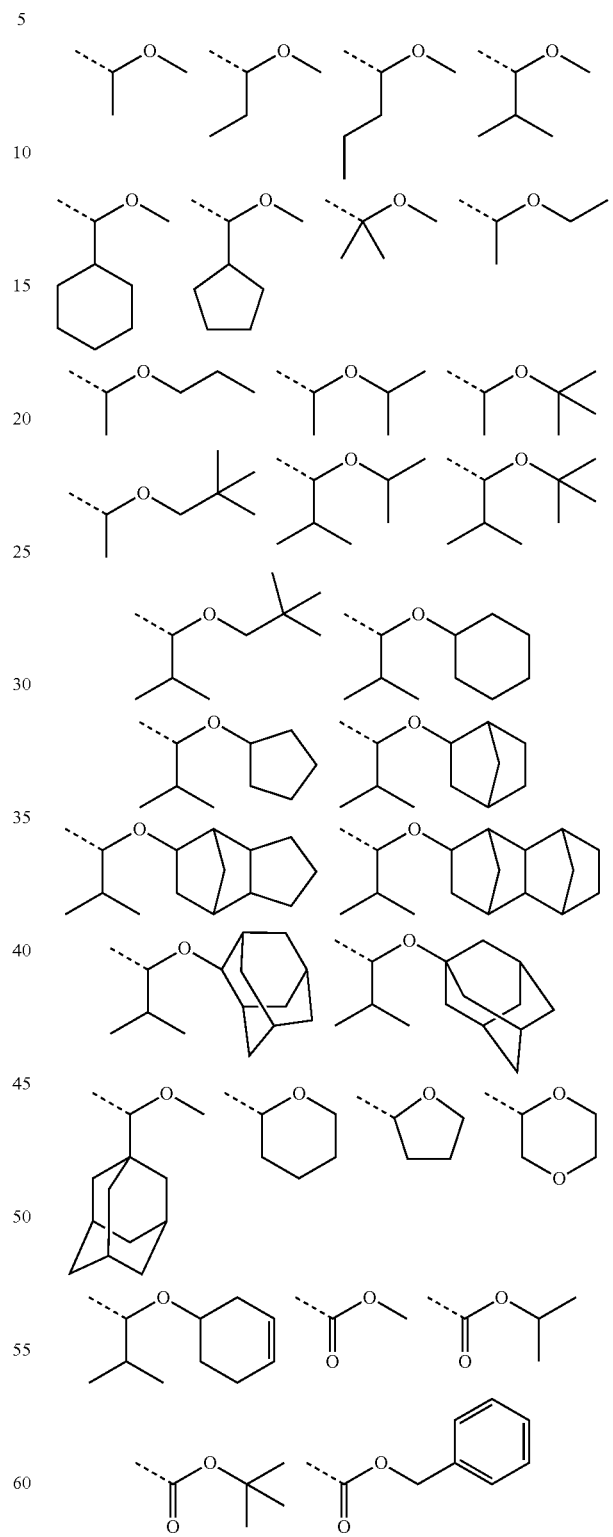

$R^b$ is not particularly limited, it is preferably an acetal structure, ketal structure or alkoxycarbonyl group, examples of which are shown below.

In formula (d1), the acid labile group $R^b$ is such that it may be deprotected to generate a hydroxyl group under the action of acid. Although the structure of the acid labile group As the acid labile group $R^b$, alkoxymethyl groups having the formula (d2) are especially preferred.

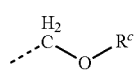
(d2)
Herein $R^c$ is a $C_1$-$C_{15}$ straight, branched or cyclic monovalent hydrocarbon group.
Examples of the acid labile group having formula (d2) are shown below, but not limited thereto.
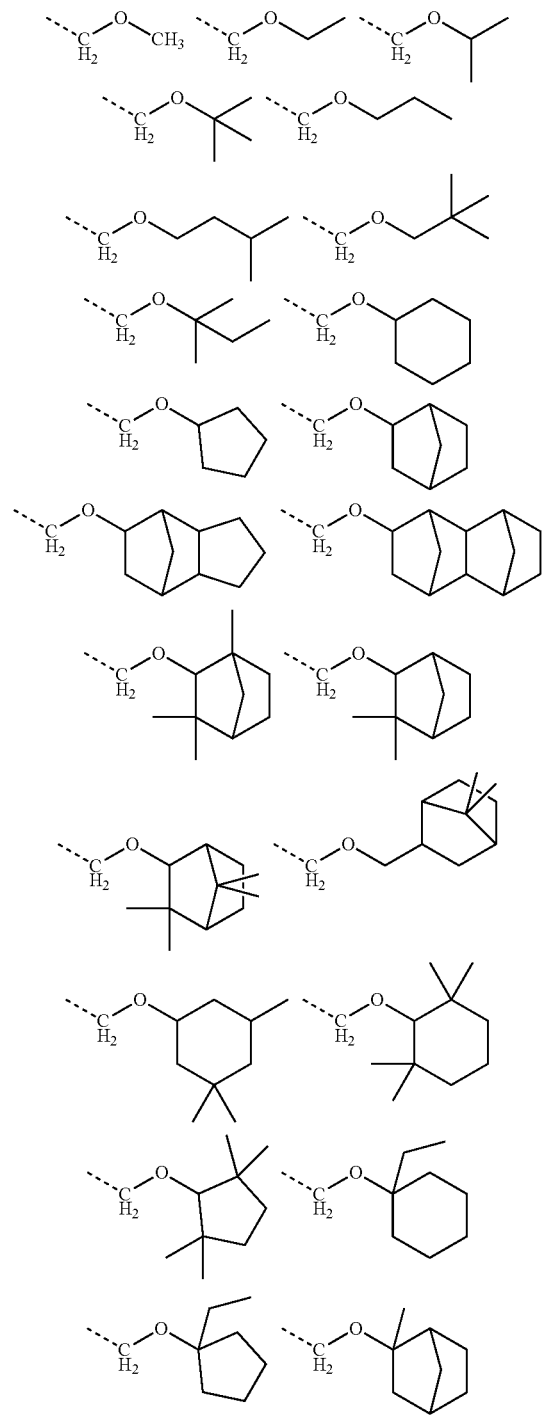
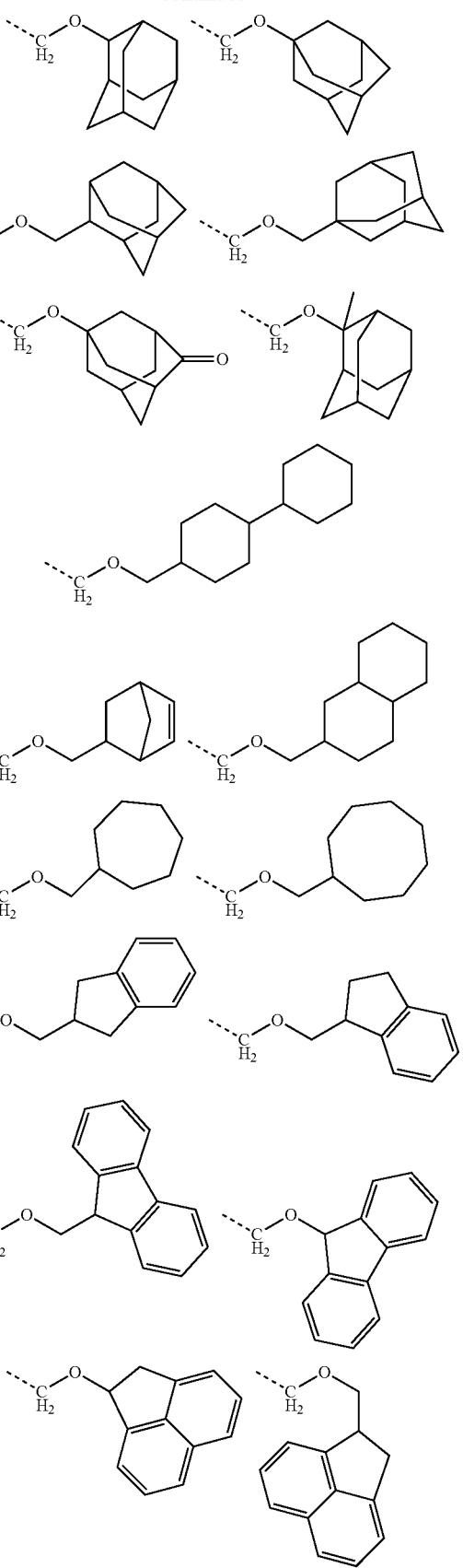

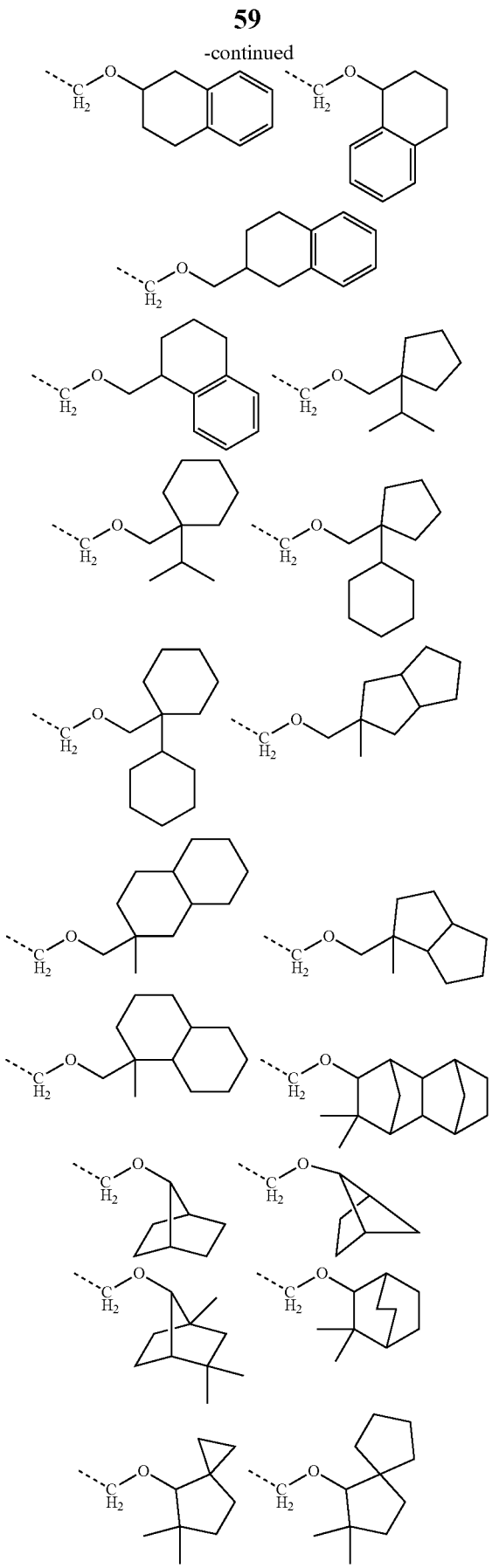
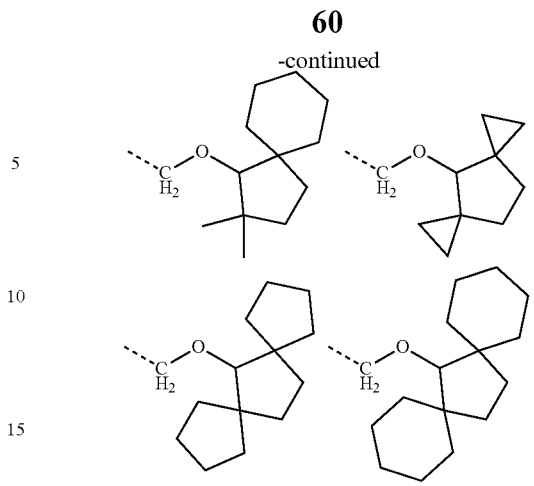

In addition to the foregoing units, the polymer may further comprise recurring units derived from, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers.

The polymer should preferably have a weight average molecular weight (Mw) in the range of 1,000 to 500,000, and more preferably 3,000 to 100,000. A polymer with a Mw in the range has etching resistance and may not suffer a drop of resolution due to a failure to provide a difference in dissolution rate before and after exposure. It is noted that Mw may be measured by GPC versus polystyrene standards using tetrahydrofuran (THF) solvent.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0 in order to provide a resist composition suitable for micropatterning to a small feature size.

As base resin (C), the polymer may be used alone or a blend of two or more polymers having different compositional ratio, Mw and/or dispersity may be used.

The polymer may be synthesized by any desired method, for example, by dissolving an unsaturated bond-containing monomer or monomers in an organic solvent, adding a radical initiator, and effecting heat polymerization. Suitable organic solvents used herein include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or the polymer may be protected or partially protected therewith at the end of polymerization.

In the polymer, appropriate molar fractions (mol %) of the respective recurring units derived from the monomers are given below although the invention is not limited thereto. The polymer may comprise:

I) recurring units of at least one type having formula (a) in a fraction of 1 to 60 mol %, preferably 5 to 50 mol %, and more preferably 10 to 50 mol %, II) recurring units of at least one type having formula (b) in a fraction of 40 to 99 mol %, preferably 50 to 95 mol %, and more preferably 50 to 90 mol %, and optionally, III) recurring units of at least one type having formulae (c1) and (c2) in a fraction of 0 to 30 mol %, preferably 0 to 20 mol %, and more preferably 0 to 10 mol %, and IV) recurring units of at least one type derived from another monomer(s) in a fraction of 0 to 80 mol %, preferably 0 to 70 mol %, and more preferably 0 to 50 mol %.

(D) Photoacid Generator

Component (D) is a photoacid generator which is not particularly limited. It may be any compound capable of generating an acid upon exposure to high-energy radiation such as UV, deep UV, EB, EUV, x-ray, excimer laser beam, gamma-ray or synchrotron radiation. Suitable photoacid generators include sulfonium salts, iodonium salts, sulfonyldiazomethane, N-sulfonyloxydicarboxyimide, O-arylsulfonyloxime and O-alkylsulfonyloxime photoacid generators. These PAGs may be used alone or in admixture of two or more. Suitable PAGs are described, for example, in U.S. Pat. No. 7,511,169 (JP-A 2007-145797, paragraphs [0102]-[0113]).

The preferred PAG has the formula (2).

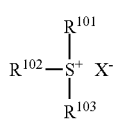

(2)

In formula (2), $R^{101}$, $R^{102}$ and $R^{103}$ are each independently a $C_1$-$C_{20}$ straight, branched or cyclic monovalent hydrocarbon group which may contain a heteroatom. Suitable monovalent hydrocarbon groups include alkyl groups such as methyl, ethyl, propyl, isopropyl, n-butyl, s-butyl, t-butyl, t-pentyl, n-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, and adamantyl, and aryl groups such as phenyl and naphthyl. Also included are the foregoing groups in which at least one hydrogen is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Among others, $R^{101}$, $R^{102}$ and $R^{103}$ are preferably optionally substituted aryl groups.

Any two of $R^{101}$, $R^{102}$ and $R^{103}$ may bond together to form a ring with the sulfur atom to which they are attached. Examples of the cation in formula (2) where two R's form a ring are shown below.

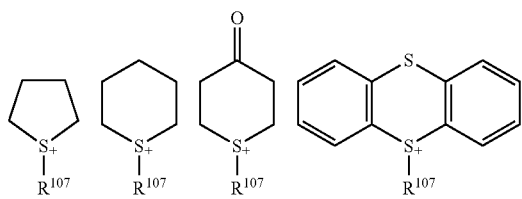

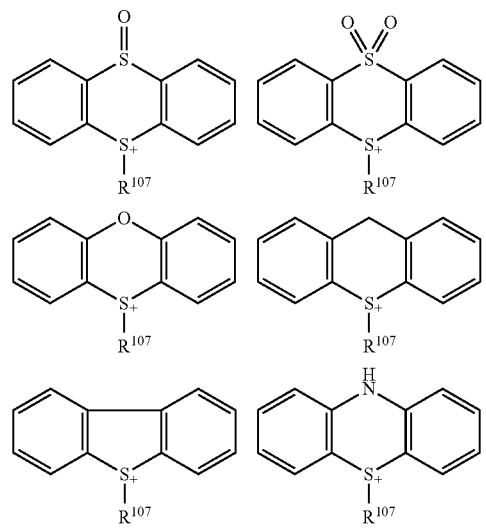

Herein $R^{107}$ is a $C_1$-$C_{20}$ straight, branched or cyclic monovalent hydrocarbon group which may contain a heteroatom. Examples of the monovalent hydrocarbon group are as exemplified above for $R^{101}$ to $R^{103}$.

Examples of the sulfonium cation in formula (2) are shown below, but not limited thereto.

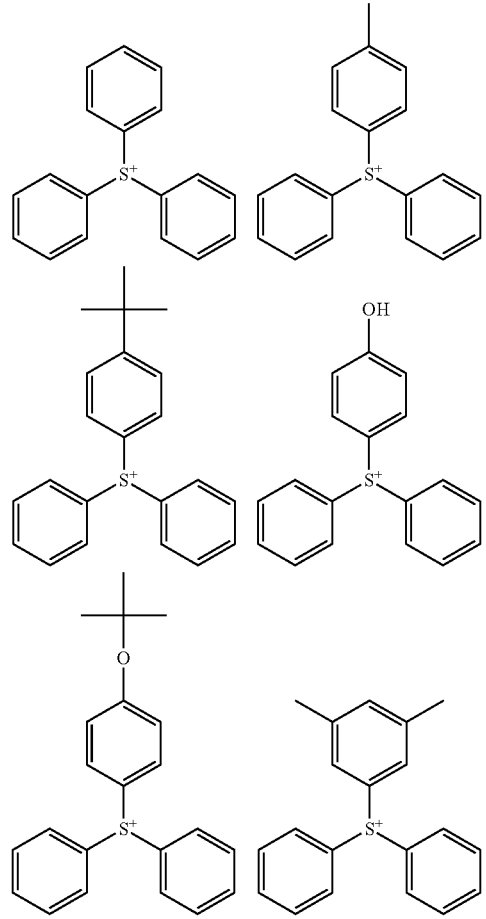

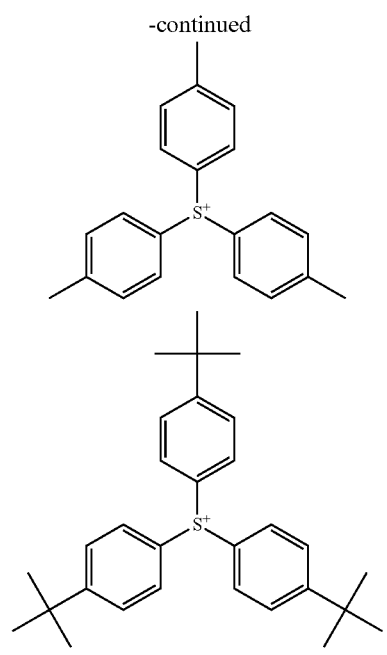
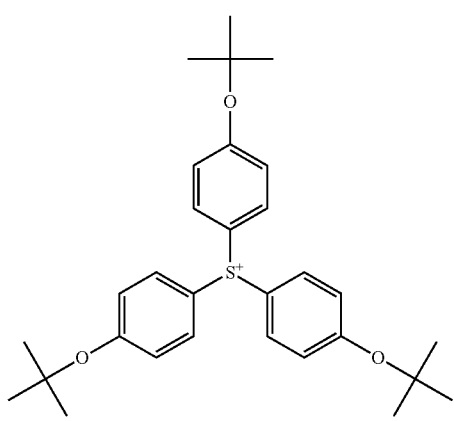
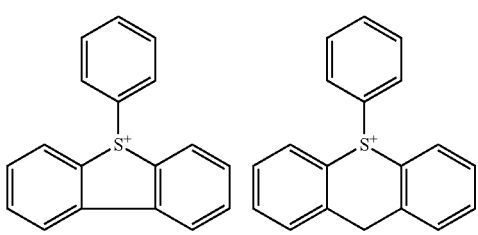
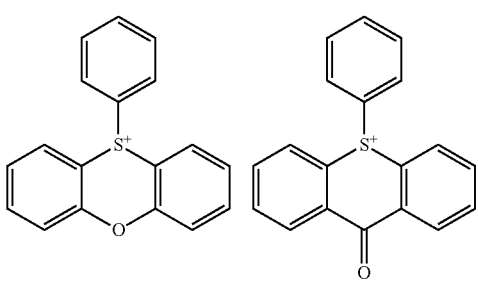

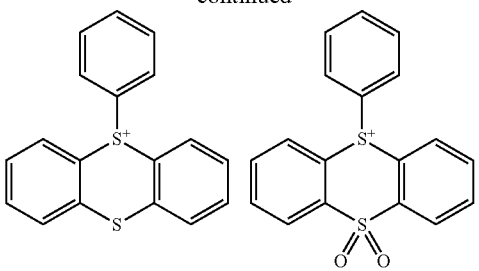
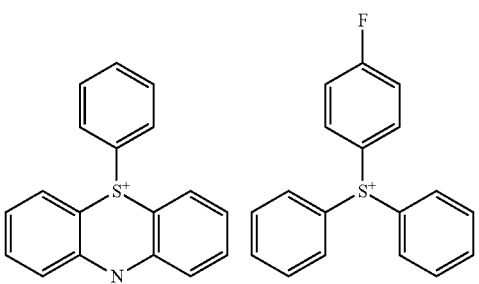

In formula (2), X⁻ is an anion selected from the formulae (2A) to (2D).

$$R^{fa}-CF_2-SO_3^- \quad (2A)$$

$$\begin{array}{c} R^{fb1}-CF_2-SO_2 \\ R^{fb2}-CF_2-SO_2 \end{array}\!\!\!\!\!\!\!\!\!\!\!\!\!\!\!\!N^- \quad (2B)$$

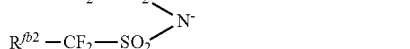
(2C)

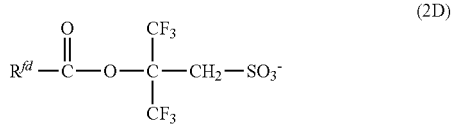
(2D)

In formula (2A), $R^{fa}$ is fluorine or a $C_1$-$C_{40}$ straight, branched or cyclic monovalent hydrocarbon group which may contain a heteroatom. Preferred structures include nonafluorobutane sulfonate, partially fluorinated sulfonates described in JP-A 2012-189977, paragraphs [0247]-[0251], partially fluorinated sulfonates described in JP-A 2013-101271, paragraphs [0261]-[0265], and partially fluorinated sulfonates described in JP-A 2013-101271, paragraphs [0261]-[0265].

Of the anions of formula (2A), a structure having formula (2A') is preferred.

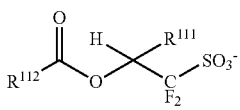

(2A')

In formula (2A'), $R^{111}$ is hydrogen or trifluoromethyl. $R^{112}$ is a $C_1$-$C_{30}$ straight, branched or cyclic monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetoxymethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (2A'), reference is made to JP-A 2007-145797, JP-A 2008-106045, JP-A 2009-007327, and JP-A 2009-258695.

Examples of the sulfonium salt having an anion of formula (2A) are shown below, but not limited thereto.

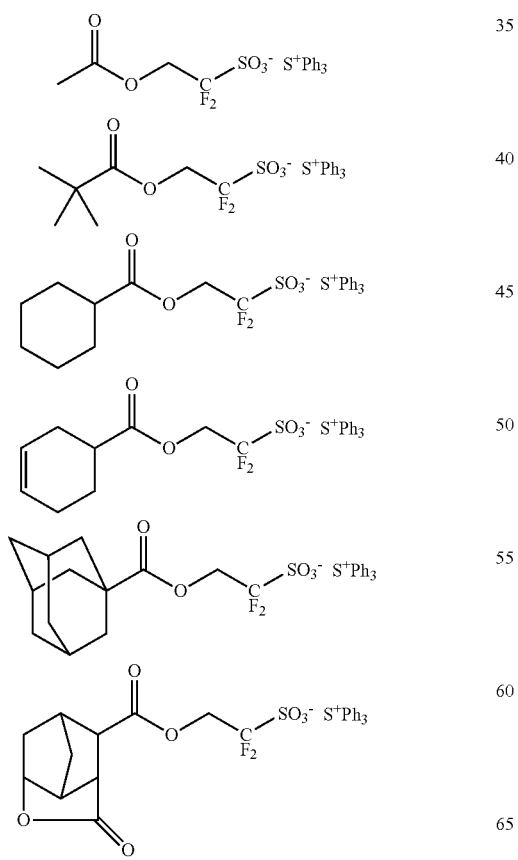

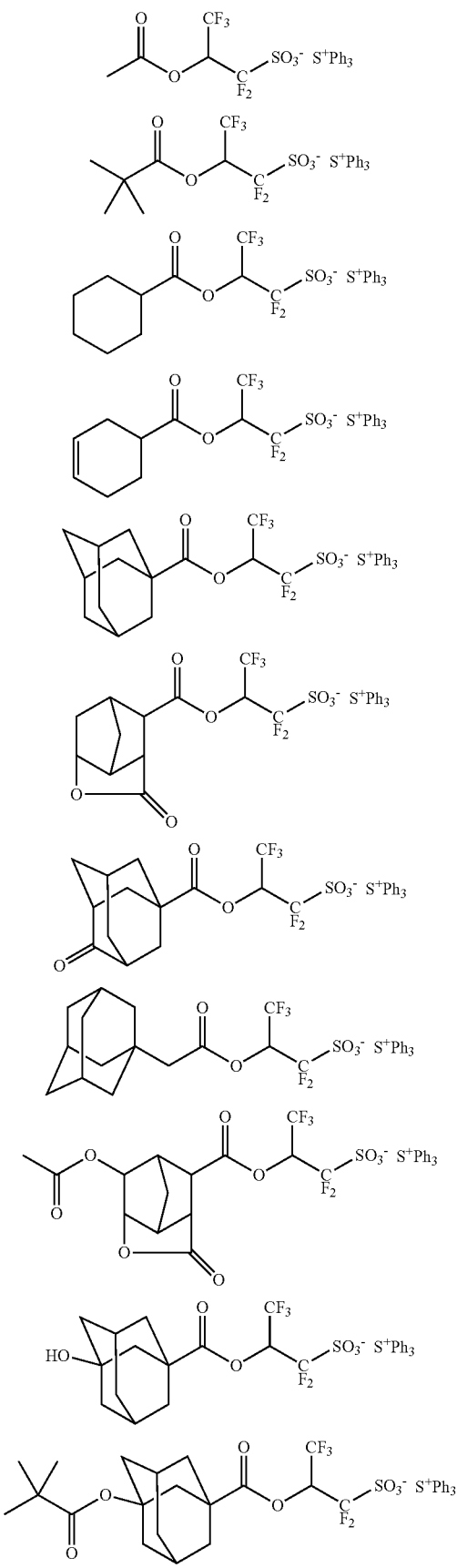

-continued

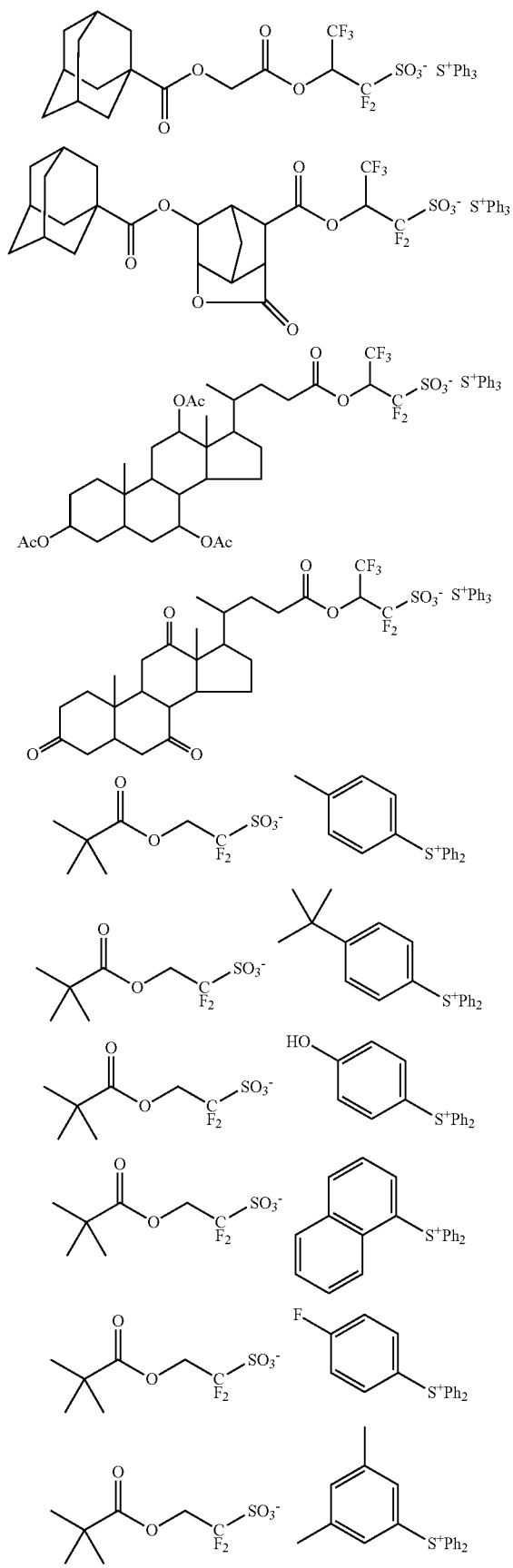

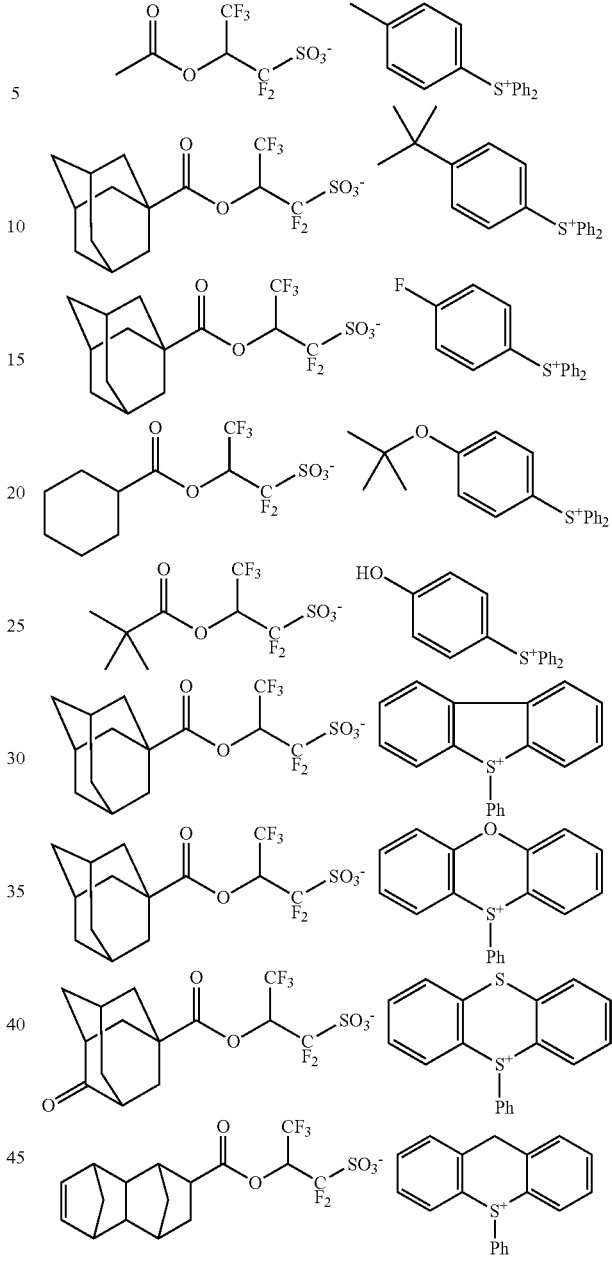

In formula (2B), $R^{fb1}$ and $R^{fb2}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fb1}$ and $R^{fb2}$ each are fluorine or a $C_1$-$C_4$ straight fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (2C), $R^{fc1}$ $R^{fc2}$ and $R^{fc3}$ are each independently fluorine or a $C_1$-$C_{40}$ straight, branched or cyclic monovalent hydrocarbon group which may contain a heteroatom. Suitable monovalent hydrocarbon groups are as exemplified above for $R^{112}$. Preferably $R^{fc1}$, $R^{fc2}$ and $R^{fc3}$ each are fluorine or a $C_1$-$C_4$ straight fluorinated alkyl group. A pair of $R^{fc1}$ and $R^{fc2}$ may bond together to form a ring with the the linkage (—$CF_2$—$SO_2$—$C^-$—$SO_2$—$CF_2$—) to which they are attached, and preferably the pair is a fluorinated ethylene or fluorinated propylene group forming a ring structure.

In formula (2D), $R^{fd}$ is a $C_1$-$C_{40}$ straight, branched or cyclic monovalent hydrocarbon group which may contain a heteroatom. Suitable monovalent hydrocarbon groups are as exemplified above for $R^{112}$.

With respect to the synthesis of the sulfonium salt having an anion of formula (2D), reference is made to JP-A 2010-215608.

Examples of the sulfonium salt having an anion of formula (2D) are shown below, but not limited thereto.

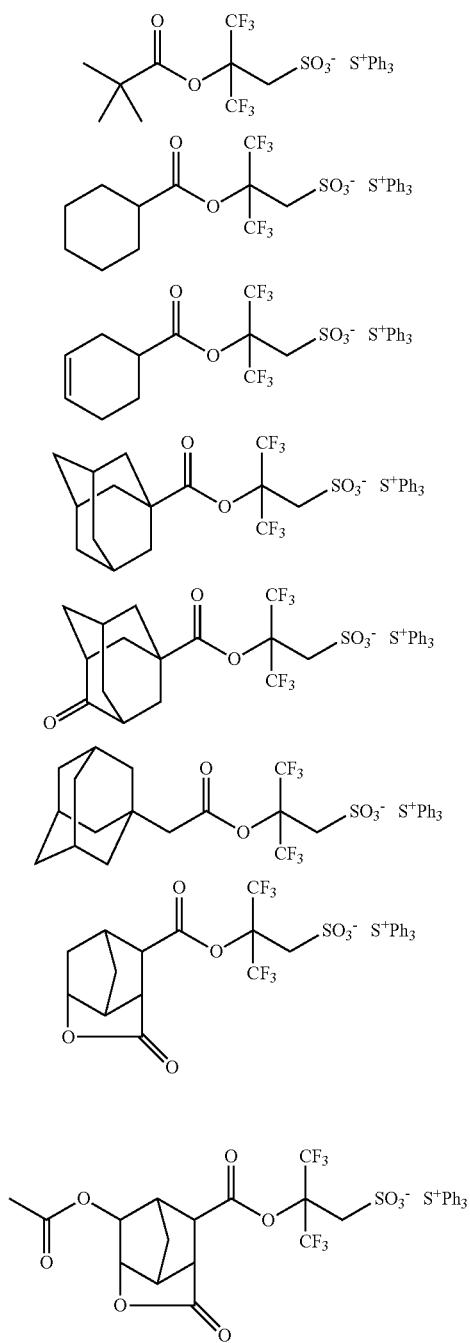

-continued

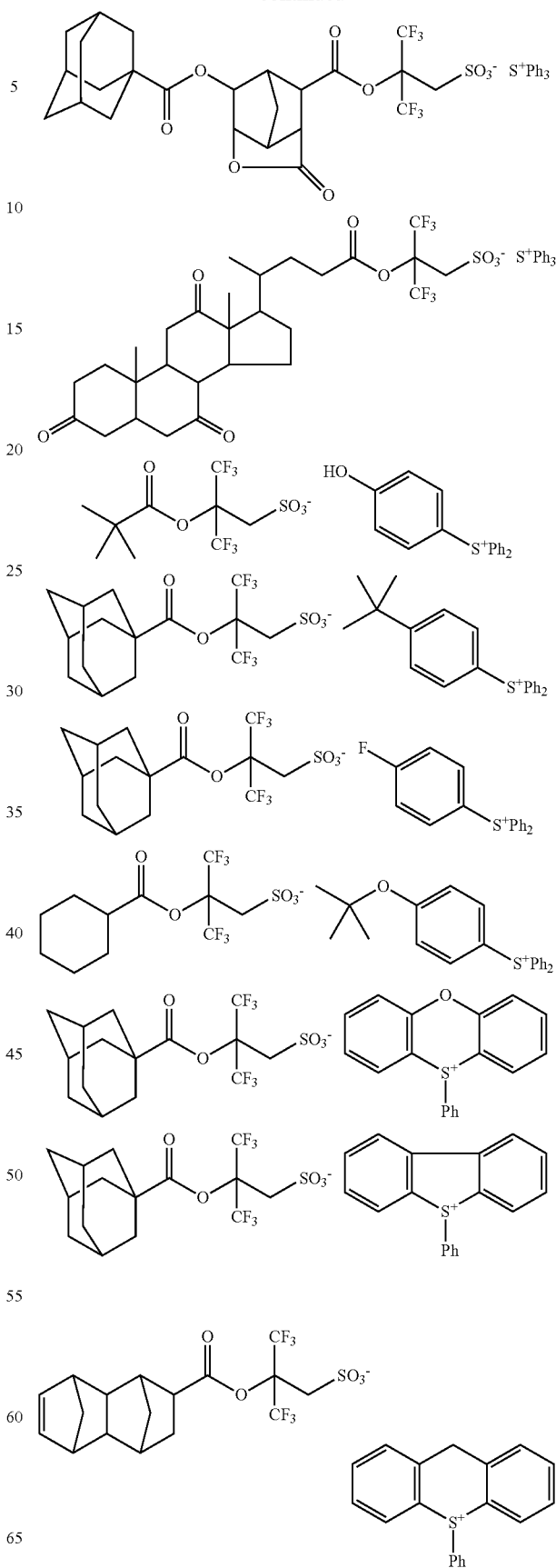

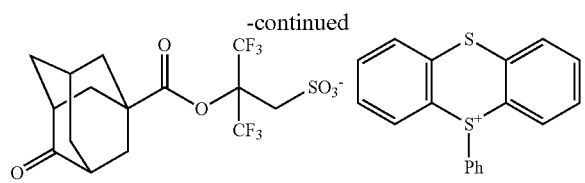

The compound having the anion of formula (2D) has a sufficient acid strength to cleave acid labile groups in the resist polymer because it is free of fluorine at α-position of sulfo group, but has two trifluoromethyl groups at β-position. Thus the compound is a useful PAG.

As the PAG (D), those compounds having the formula (3) are also preferred.

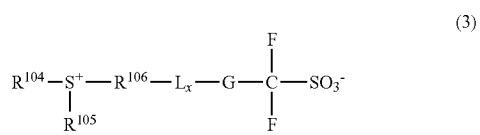

In formula (3), $R^{104}$ and $R^{105}$ are each independently a $C_1$-$C_{20}$ straight, branched or cyclic monovalent hydrocarbon group which may contain a heteroatom. $R^{104}$ and $R^{105}$ may bond together to form a ring with the sulfur atom to which they are attached. $R^{106}$ is a $C_1$-$C_{20}$ straight, branched or cyclic divalent hydrocarbon group which may contain a heteroatom. G is a single bond, or a $C_1$-$C_{20}$ straight, branched or cyclic divalent hydrocarbon group which may contain a heteroatom. $L_x$ is a divalent linking group.

Suitable monovalent hydrocarbon groups $R^{104}$ and $R^{105}$ include methyl, ethyl, propyl, isopropyl, n-butyl, s-butyl, t-butyl, n-pentyl, t-pentyl, n-hexyl, n-octyl, cyclopentyl, cyclohexyl, 2-ethylhexyl, cyclopentylmethyl, cyclopentylethyl, cyclohexylmethyl, cyclohexylethyl, norbornyl, oxanorbornyl, tricyclo[5.2.1.0$^{2,6}$]decanyl, adamantyl, phenyl, and naphthyl. Also included are the foregoing groups in which at least one hydrogen is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl radical. Among others, $R^{104}$ and $R^{105}$ are preferably optionally substituted aryl groups.

Examples of the divalent hydrocarbon group $R^{106}$ include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl radical. Among others, $R^{106}$ is preferably an optionally substituted aryl group.

Examples of the divalent hydrocarbon group G include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl; and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl, cyano, carbonyl, ether bond, ester bond, sulfonic acid ester bond, carbonate bond, lactone ring, sultone ring, carboxylic acid anhydride or haloalkyl radical. Among others, G is preferably methylene or methylene in which hydrogen is substituted by fluorine or trifluoromethyl.

Examples of the linking group $L_x$ include an ether bond, ester bond, thioether bond, sulfinic acid ester bond, sulfonic acid ester bond, carbonate bond and carbamate bond.

Examples of the PAG having formula (3) are given below, but not limited thereto. Herein G' is hydrogen, fluorine or trifluoromethyl.

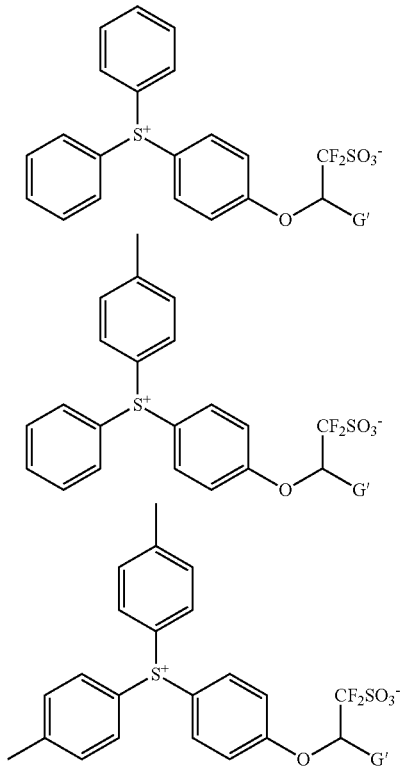

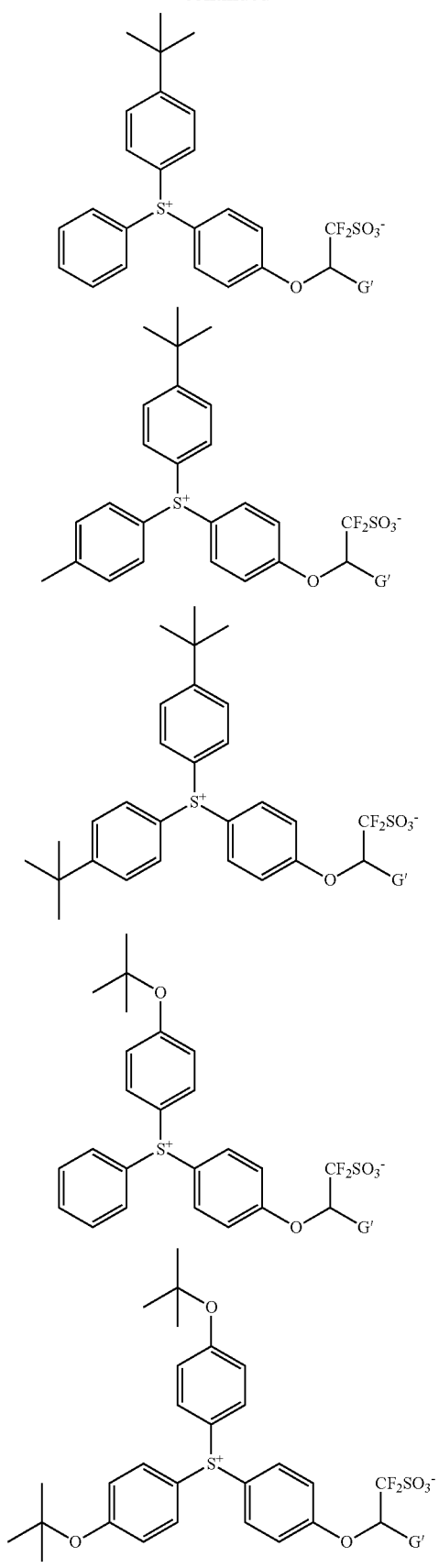
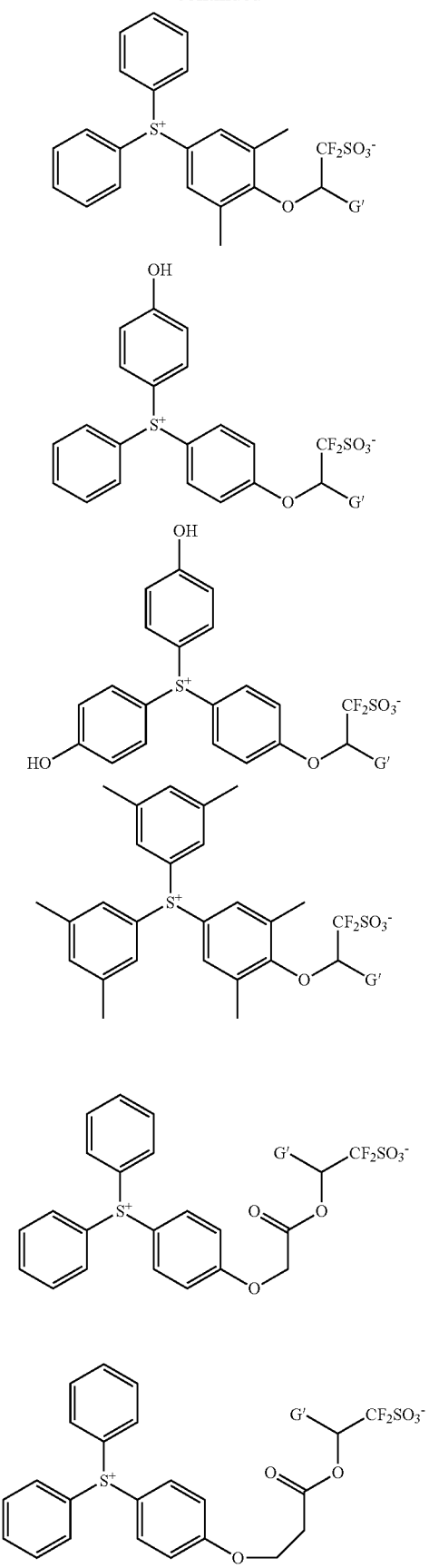

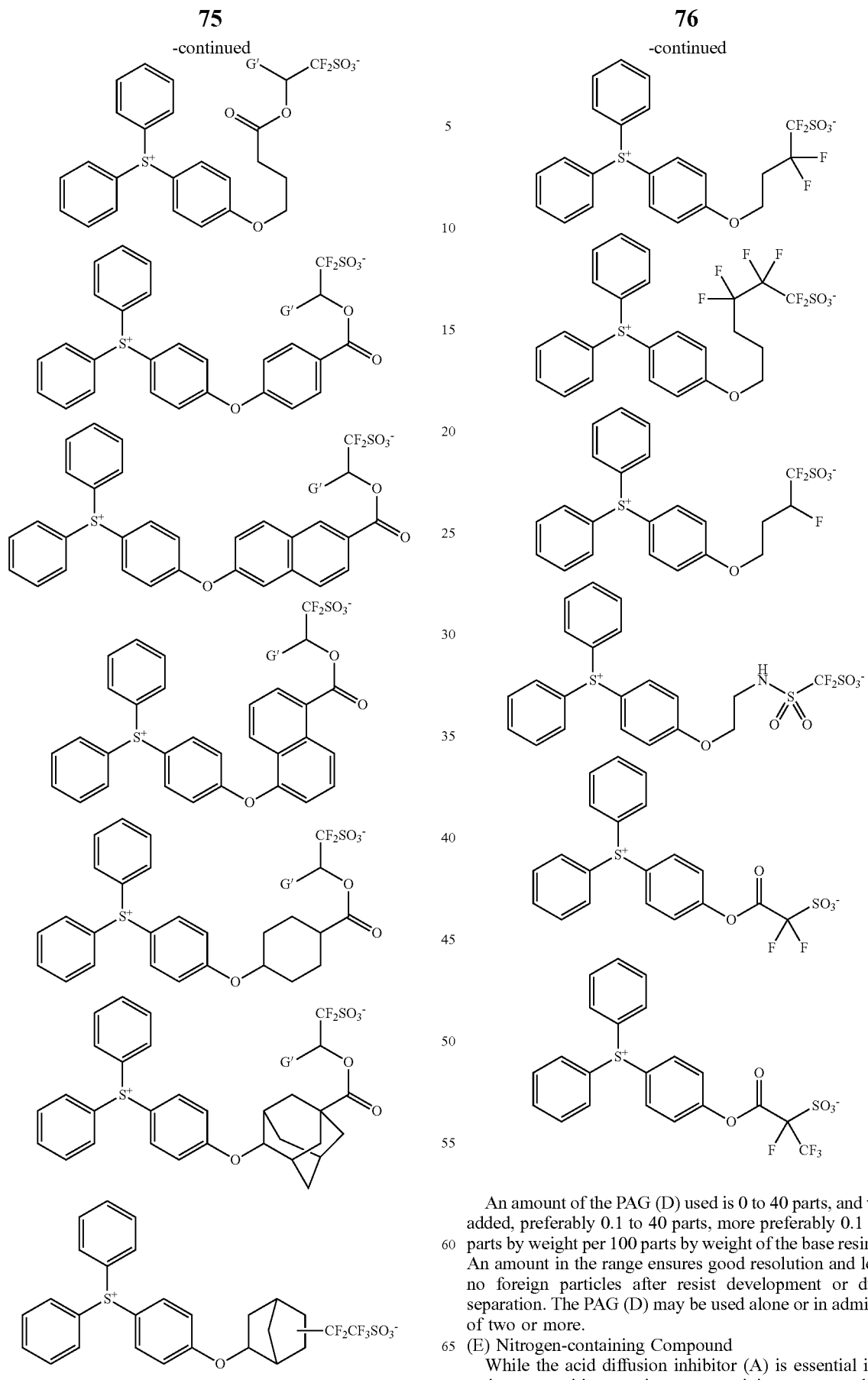

An amount of the PAG (D) used is 0 to 40 parts, and when added, preferably 0.1 to 40 parts, more preferably 0.1 to 20 parts by weight per 100 parts by weight of the base resin (C). An amount in the range ensures good resolution and leaves no foreign particles after resist development or during separation. The PAG (D) may be used alone or in admixture of two or more.

(E) Nitrogen-containing Compound

While the acid diffusion inhibitor (A) is essential in the resist composition, a nitrogen-containing compound may also be added as another acid diffusion inhibitor. Suitable nitrogen-containing compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146]-[0164] (U.S. Pat. No. 7,537,880). Also useful are compounds whose primary or secondary amine is protected with a carbamate group as described in JP 3790649.

Also, a sulfonium salt of sulfonic acid having a nitrogen-containing substituent may be used as component (E). This compound is a so-called photo-degradable base which functions as quencher in the unexposed region, but loses quencher ability through neutralization with the acid generated by itself, in the exposed region. The use of photo-degradable base is effective for enhancing the contrast between exposed and unexposed regions. With respect to the photo-degradable base, reference may be made to JP-A 2009-109595 and JP-A 2012-046501, for example.

The nitrogen-containing compounds may be used alone or in admixture of two or more. The nitrogen-containing compound (E) is preferably used in an amount of 0.001 to 12 parts, more preferably 0.01 to 8 parts by weight per 100 parts by weight of the base resin (B).

(F) Surfactant which is Insoluble or Substantially Insoluble in Water and Soluble in Alkaline Developer, and/or Surfactant which is Insoluble or Substantially Insoluble in Water and Alkaline Developer (Hydrophobic Resin)

To the resist composition, a surfactant which is insoluble or substantially insoluble in water and soluble in alkaline developer, and/or a surfactant which is insoluble or substantially insoluble in water and alkaline developer (hydrophobic resin) may be added as component (F). Reference should be made to those compounds described in JP-A 2010-215608 and JP-A 2011-16746.

While many examples of the surfactant which is insoluble or substantially insoluble in water and alkaline developer are described in these patent documents, preferred examples are FC-4430, Surflon® S-381, Surfynol® E1004, KH-20 and KH-30, which may be used alone or in admixture. Partially fluorinated oxetane ring-opened polymers having the structural formula (surf-1) are also useful.

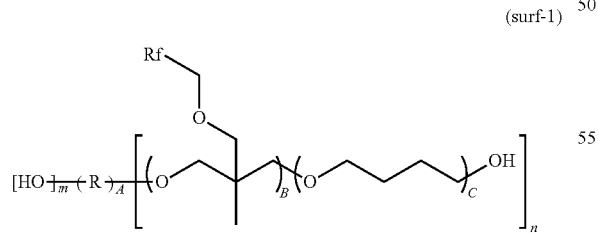
(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

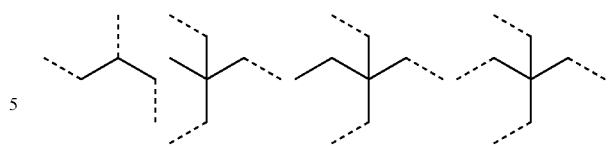

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are those comprising recurring units as shown below.

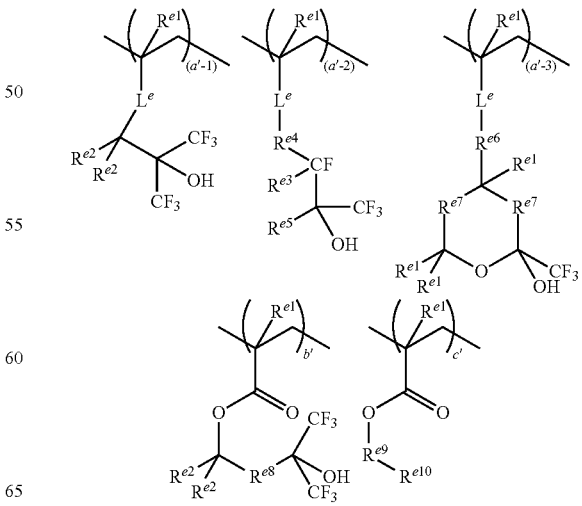

Herein $R^{e1}$ is each independently hydrogen, fluorine, methyl or trifluoromethyl. $R^{e2}$ is each independently hydrogen or a $C_1$-$C_{20}$ straight, branched or cyclic alkyl or fluoroalkyl group, or two $R^{e2}$ in a common monomer may bond together to form a ring with the carbon atom to which they are attached, and in this event, they together represent a $C_2$-$C_{20}$ straight, branched or cyclic alkylene or fluoroalkylene group.

$R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a $C_1$-$C_6$ straight, branched or cyclic alkylene group in which at least one hydrogen atom may be substituted by a fluorine atom. $R^{e5}$ is a $C_1$-$C_{10}$ straight or branched alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ is a single bond or a $C_1$-$C_4$ alkylene.

$R^{e7}$ is each independently a single bond, —O—, or —$CR^{e1}R^{e1}$—. $R^{e8}$ is a $C_1$-$C_4$ straight or $C_3$-$C_4$ branched alkylene group, or may bond with $R^{e2}$ within a common monomer to form a $C_3$-$C_6$ non-aromatic ring with the carbon atom to which they are attached.

$R^{e9}$ is methylene, 1,2-ethylene, 1,3-propylene or 1,4-butylene. $R^{e10}$ is a $C_3$-$C_6$ linear perfluoroalkyl group, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O— wherein $R^{e11}$ is a $C_1$-$C_{10}$ straight, branched or cyclic alkylene group. The subscripts are in the range: $0 \le (a'-1) \le 1$, $0 \le (a'-2) \le 1$, $0 \le (a'-3) \le 1$, $0 < (a'-1)+(a'-2)+(a'-3) \le 1$, $0 \le b' \le 1$, $0 \le c' \le 1$, and $0 < (a'-1)+(a'-2)+(a'-3)+b'+c' \le 1$.

Exemplary non-limiting units are shown below. $R^{e1}$ is as defined above.

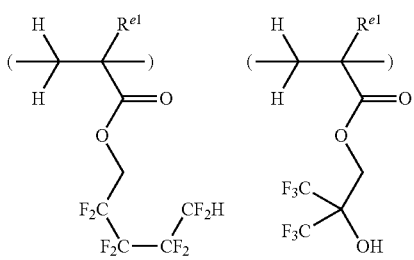

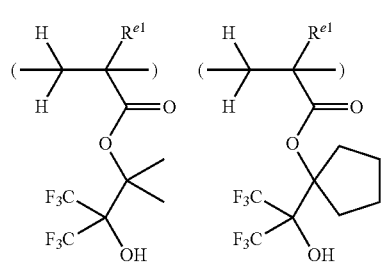

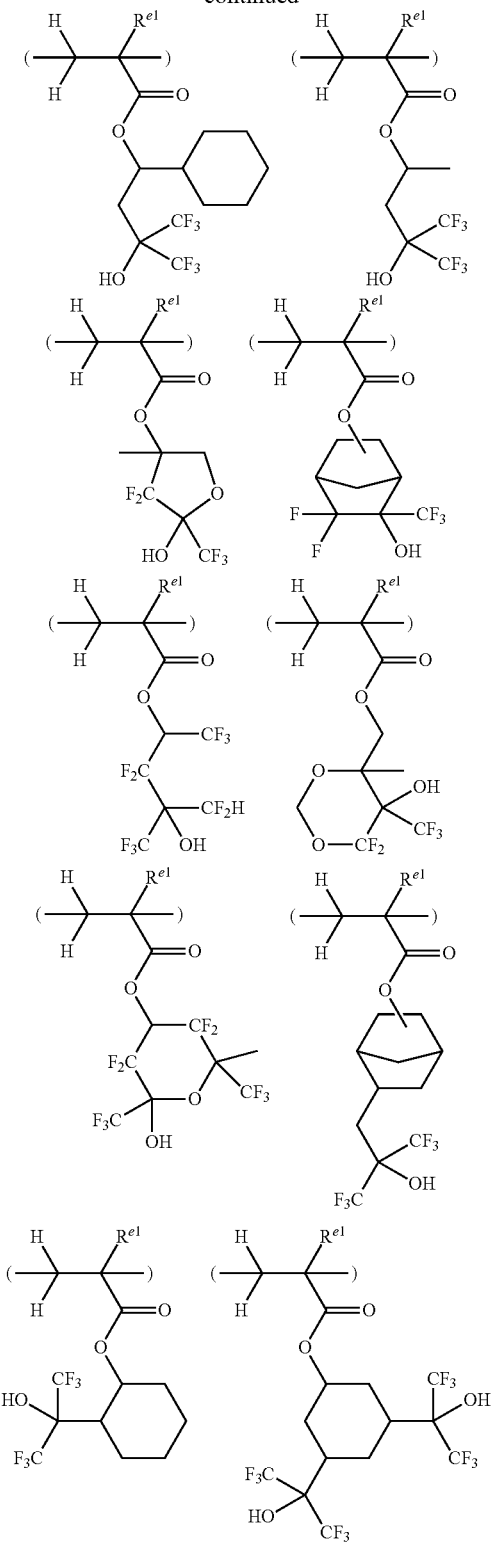

For the surfactant which is insoluble or substantially insoluble in water and soluble in alkaline developer, reference may be made to JP-A 2008-122932, JP-A 2010-134012, JP-A 2010-107695, JP-A 2009-276363, JP-A 2009-192784, JP-A 2009-191151, JP-A 2009-098638, JP-A 2011-250105, and JP-A 2011-042789.

The polymeric surfactant preferably has a Mw of 1,000 to 50,000, more preferably 2,000 to 20,000 as measured by GPC versus polystyrene standards. A surfactant with a Mw in the range is effective for surface modification and causes few development defects.

Component (F) is preferably formulated in an amount of 0 to 20 parts by weight per 100 parts by weight of the base resin (C). When added, the amount of component (F) is preferably at least 0.001 part, more preferably at least 0.01 part and also preferably up to 15 parts, more preferably up to 10 parts by weight. Component (F) may be used alone or in admixture.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

Specifically, the resist composition is applied onto a substrate for integrated circuit fabrication (e.g., Si, $SiO_2$, SiN, SiON, TiN, WSi, BPSG, SOG or organic antireflective coating) or substrate for mask circuit fabrication (e.g., Cr, CrO, CrON, $MoSi_2$ or $SiO_2$) by a suitable coating technique such as spin coating. The coating is prebaked on a hotplate at a temperature of 60 to 150° C. for 1 to 10 minutes, preferably 80 to 140° C. for 1 to 5 minutes, to form a resist film of 0.05 to 2μm thick. Through a mask with the desired pattern placed over the resist film, the resist film is exposed to high-energy radiation, typically KrF excimer laser, ArF excimer laser or EUV radiation in a dose of 1 to 200 $mJ/cm^2$, and preferably 10 to 100 $mJ/cm^2$. The exposure may be performed by conventional lithography whereas the immersion lithography of holding a liquid (refractive index≥1.0) between the projection lens and the resist film may be employed if desired. In this case, a protective film which is insoluble in water may be applied on the resist film. The resist film is then baked (PEB) on a hotplate at 60 to 150° C. for 1 to 5 minutes, preferably 80 to 140° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The water-insoluble protective film which is used in the immersion lithography is to prevent any components from being leached out of the resist film and to improve water slippage at the film surface and is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also a double patterning process may be used for pattern formation. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Although the pattern forming process often uses an alkaline aqueous solution as the developer, the negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, phenyl acetate, propyl formate, butyl formate, isobutyl formate, pentyl formate, isopentyl formate, methyl valerate, methyl pentenoate, methyl crotonate, ethyl crotonate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples of the invention are given below by way of illustration and not by way of limitation. The abbreviation "pbw" is parts by weight. Analytic instruments are as shown below.

IR: NICOLET 6700 by Thermo Fisher Scientific Inc.

$^1$H-NMR: ECA-500 by JEOL Ltd.

$^{19}$F-NMR: ECA-500 by JEOL Ltd.

LC-MS: ACQUITY UPLC H-Class System and ACQUITY QDa by Waters

1) Synthesis of Sulfonium Compounds

Example 1-1

Synthesis of 2-(diphenylsulfonio)phenolate (Q-A)

(1) Synthesis of (2-tert-butoxyphenyl)diphenylsulfonium chloride (Intermediate A)

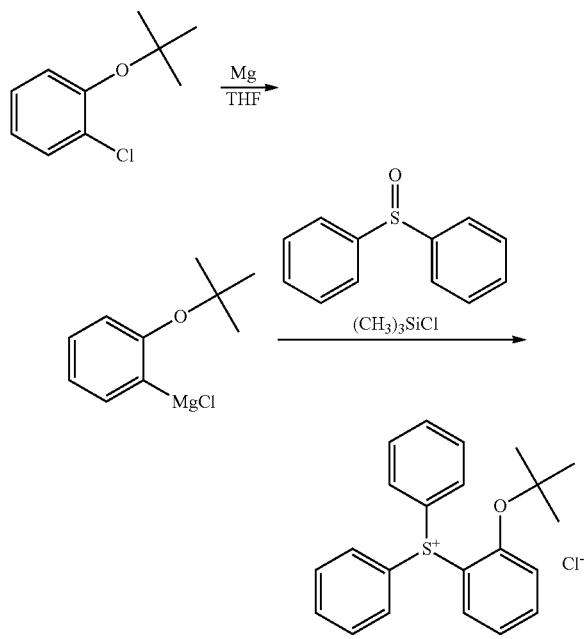

A Grignard reagent was prepared by the standard technique using 2.6 g of magnesium and 16 g of 2-tert-butoxychlorobenzene in THF. To the Grignard reagent were added 6.1 g of diphenyl sulfoxide and 27 g of THF. At room temperature, 9.8 g of chlorotrimethylsilane was added dropwise to the mixture, which was aged for 3 hours. After aging, a saturated aqueous solution of ammonium chloride was added to quench the reaction. The reaction mixture was combined with 100 g of water and washed with diisopropyl ether, yielding an aqueous solution of the desired compound, (2-tert-butoxyphenyl)diphenylsulfonium chloride (Intermediate A). The solution was passed to the next step without isolation.

(2) Synthesis of (2-hydroxyphenyl)diphenylsulfonium tosylate (Intermediate B)

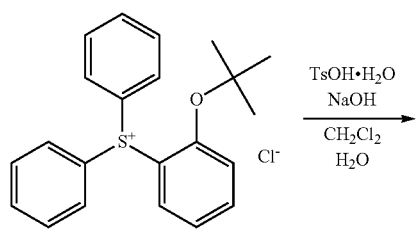

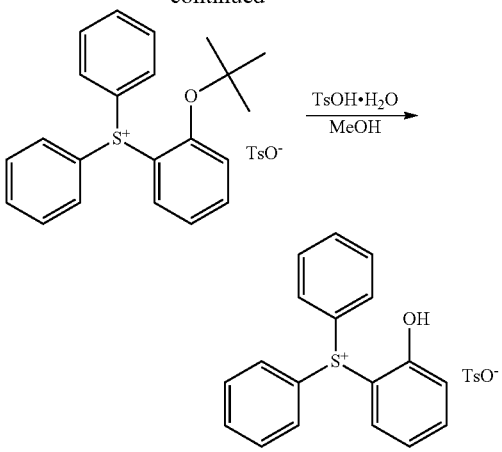

Next, 6.8 g of p-toluenesulfonic acid monohydrate, 6.1 g of 25 wt % sodium hydroxide aqueous solution, 30 g of water, and 150 g of methylene chloride were added to the overall volume of the Intermediate A aqueous solution, which was stirred for 30 minutes. The organic layer was separated and washed with water, after which methylene chloride was removed by vacuum concentration, yielding (2-tert-butoxyphenyl)diphenylsulfonium tosylate in crude form. To the crude product, 6 g of p-toluenesulfonic acid monohydrate and 50 g of methanol were added whereupon the mixture was heated at 80° C. for 14 hours for deprotection reaction. The reaction solution was concentrated in vacuum at 60° C., methylene chloride was added, and the organic layer was washed with ultrapure water. After washing, the organic layer was concentrated in vacuum. To the residue, tert-butyl methyl ether was added for recrystallization. The resulting crystal was recovered and dried in vacuum, obtaining the desired compound, (2-hydroxyphenyl)diphenylsulfonium tosylate (Intermediate B) (amount 6 g, overall yield from synthesis of Intermediate A 45%).

(3) Synthesis of 2-(diphenylsulfonio)phenolate (Q-A)

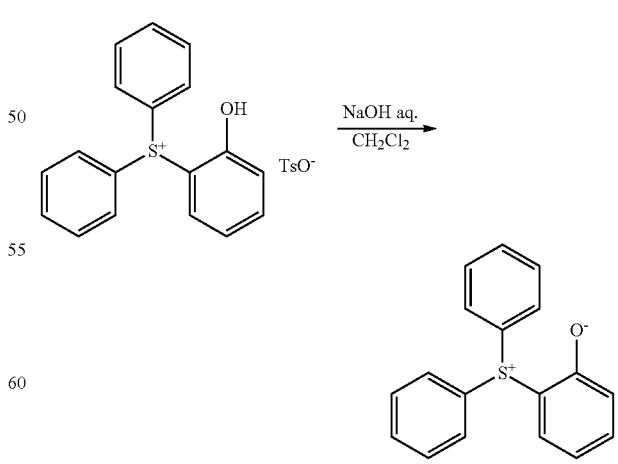

Intermediate B, 4.5 g, was dissolved in 22 g of methylene chloride. Then 1.6 g of 25 wt % sodium hydroxide aqueous solution and 10 g of pure water was added to the solution, which was stirred for 30 minutes. After stirring, 1-pentanol was added to the solution. The organic layer was separated, washed with water, and concentrated in vacuum. Methyl isobutyl ketone was added to the concentrate, followed by vacuum concentration again. To the residue, diisopropyl ether was added for recrystallization. The resulting crystal was recovered and dried in vacuum, obtaining the target compound, 2-(diphenylsulfonio)phenolate (Q-A) (amount 2.5 g, yield 91%).

The target compound was analyzed by spectroscopy. The NMR spectrum, $^1$H-NMR in DMSO-$d_6$ is shown in FIG. 1. In $^1$H-NMR analysis, minute amounts of residual solvents (diisopropyl ether, methyl isobutyl ketone) and water were observed.

Infrared absorption spectrum (IR (D-ATR)):
ν=2990, 1580, 1485, 1478, 1442, 1360, 1285, 1007, 997, 840, 745, 724, 687 cm$^{-1}$ LC-MS: Positive [M+H]$^+$ 279 (corresponding to $C_{18}H_{15}OS^+$)

Example 1-2

Synthesis of 2-(diphenylsulfonio)-5-fluorophenolate (Q-B)

(1) Synthesis of 1-bromo-2-tert-butoxy-4-fluorobenzene (Intermediate C)

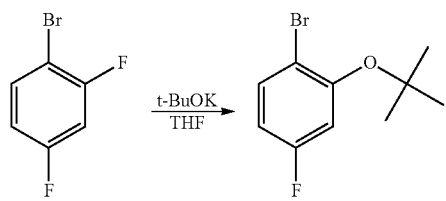

Under heating at 50° C., 1 kg of 1-bromo-2,4-difluorobenzene was added dropwise to a solution of 553 g of potassium tert-butoxide in 4 kg of THF, which was aged at 50° C. for 20 hours. The reaction solution was concentrated in vacuum, after which 3.5 kg of hexane and 3 kg of pure water were added to the concentrate. The organic layer was separated, washed with water and thereafter concentrated in vacuum. Methanol was added to the concentrate for recrystallization. The resulting crystal was recovered by filtration and heat dried in vacuum, obtaining the desired compound, 1-bromo-2-tert-butoxy-4-fluorobenzene (Intermediate C) (amount 815 g, yield 66%).

(2) Synthesis of (2-hydroxy-4-fluorophenyl)diphenylsulfonium tosylate (Intermediate D)

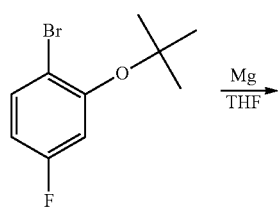

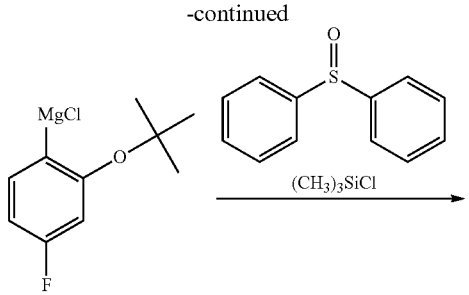

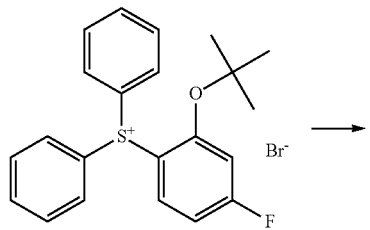

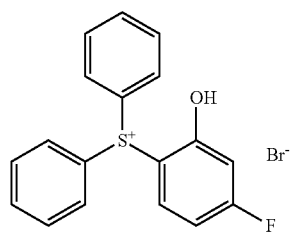

A Grignard reagent was prepared by the standard technique using 72 g of magnesium and 741 g of Intermediate C in THF. To the Grignard reagent were added 202 g of diphenyl sulfoxide and 400 g of THF. Under heating at 60° C., 325 g of chlorotrimethylsilane was added dropwise to the mixture, which was aged for 15 hours. After aging, 104 g of 35 wt % dilute hydrochloric acid and 2,300 g of pure water were added to quench the reaction. The reaction mixture was combined with 2.5 kg of diisopropyl ether, from which the water layer was separated. Then 200 g of 35 wt % dilute hydrochloric acid was added to the water layer, which was aged at 60° C. for 5 hours. The crystal thus precipitated was collected by filtration and washed with diisopropyl ether, and heat dried in vacuum, obtaining the desired compound, (2-hydroxy-4-fluorophenyl)diphenylsulfonium tosylate (Intermediate D) (amount 229 g, yield 59%).

(3) Synthesis of 2-(diphenylsulfonio)-5-fluorophenolate (Q-B)

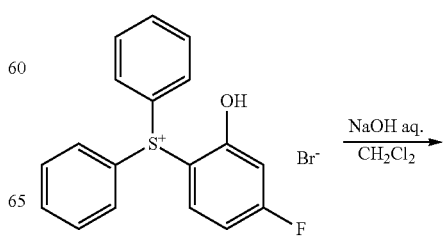

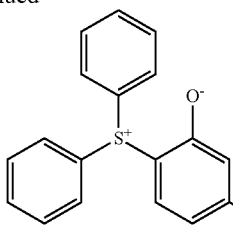

A mixture of 3.0 g of Intermediate D, 1.2 g of 25 wt % sodium hydroxide aqueous solution, 50 g of methylene chloride and 20 g of pure water was stirred for 10 minutes. The organic layer was separated, washed with pure water, and concentrated in vacuum. To the residue, diisopropyl ether was added for recrystallization. The resulting crystal was recovered and dried in vacuum, obtaining the target compound, 2-(diphenylsulfonio)-5-fluorophenolate (Q-B) (amount 1.5 g, yield 66%).

Figure 2:
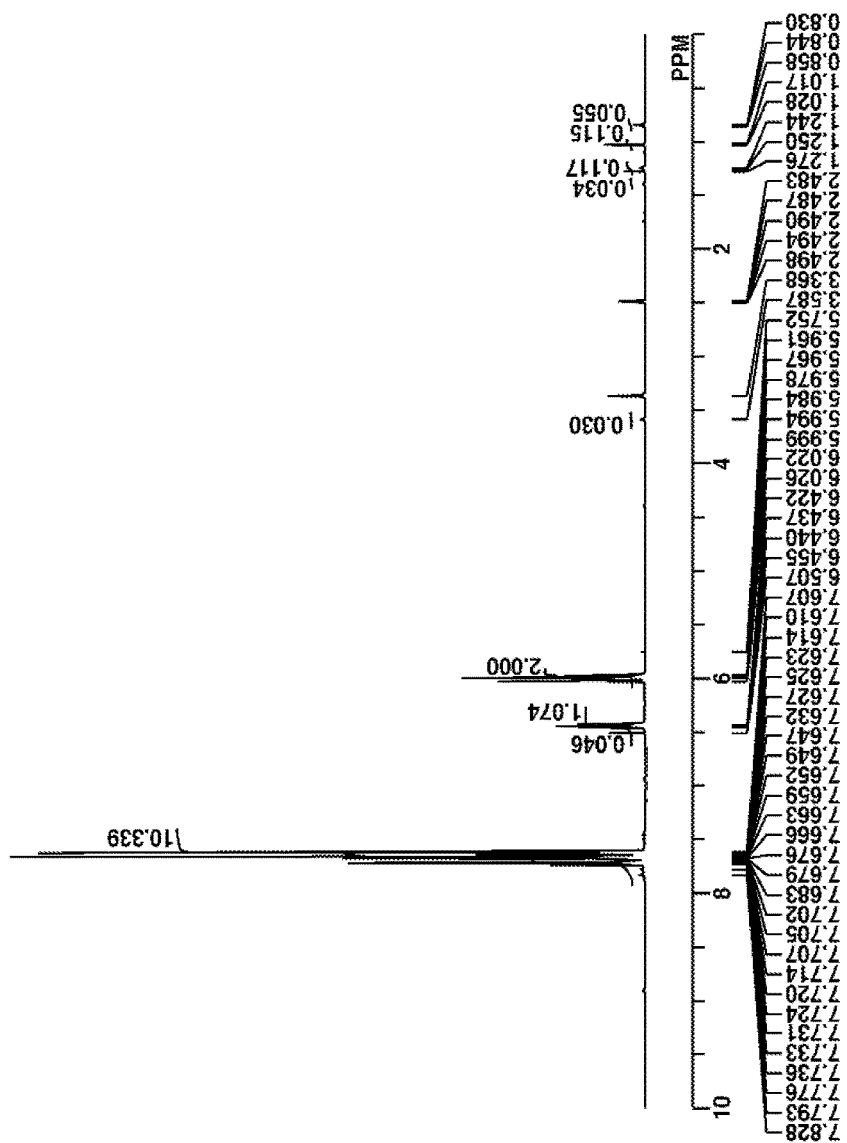
FIG. 2 is a diagram of $^1$H-NMR spectrum of compound Q-B obtained in Example 1-2.
Figure 3:
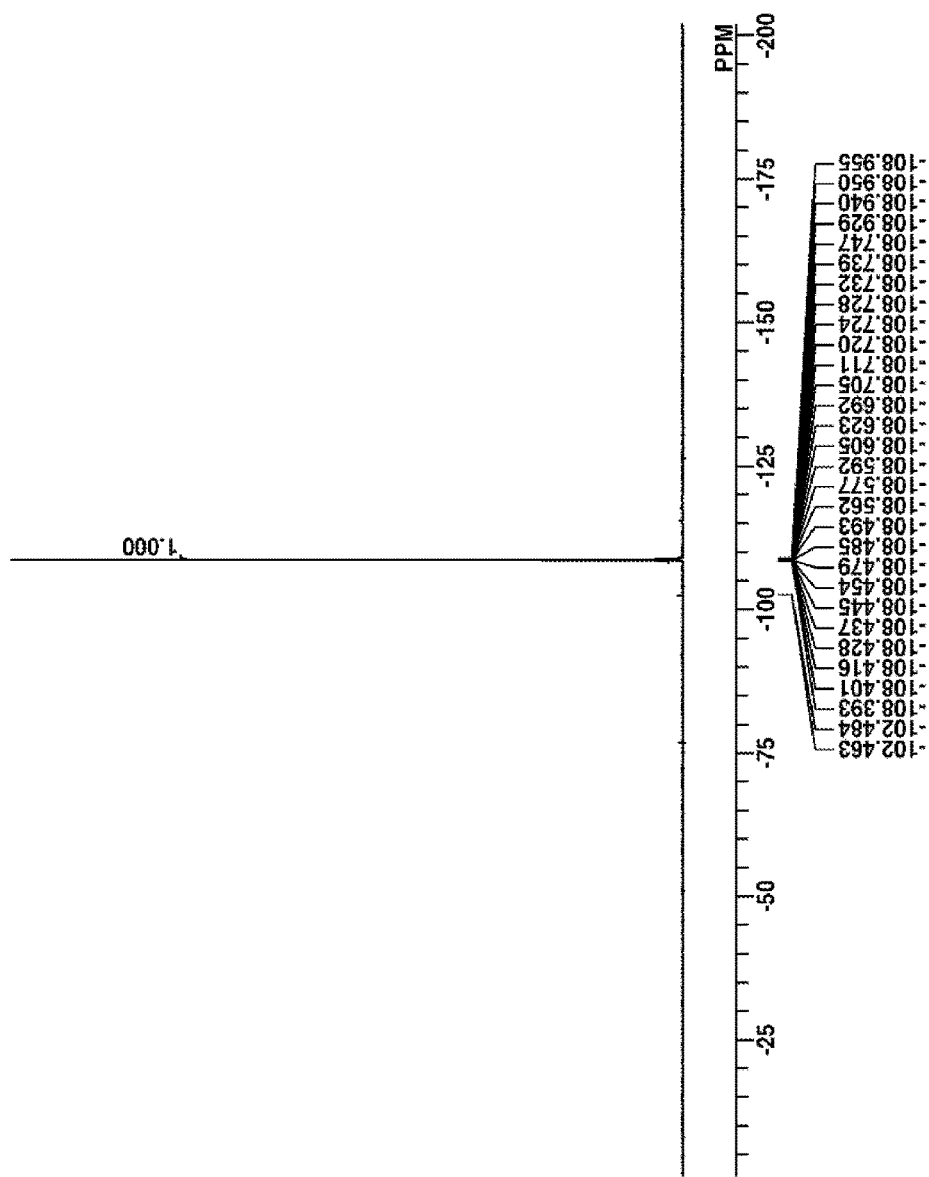
FIG. 3 is a diagram of $^{19}$F-NMR spectrum of compound Q-B in Example 1-2.

The target compound was analyzed by spectroscopy. The NMR spectra, $^1$H-NMR and $^{19}$F-NMR in DMSO-$d_6$ are shown in FIGS. 2 and 3. In $^1$H-NMR analysis, minute amounts of residual solvents (diisopropyl ether, methyl isobutyl ketone) and water were observed.

IR (D-ATR): ν=2992, 1590, 1530, 1488, 1478, 1446, 1317, 1284, 1148, 1115, 964, 834, 763, 755, 688 cm$^{-1}$

LC-MS: Positive [M+H]$^+$ 297 (corresponding to $C_{18}H_{14}OFS^+$)

Example 1-3

Synthesis of 2-(4-tert-butylphenyl)(phenyl)sulfoniophenolate (Q-C)

(1) Synthesis of (4-tert-butylphenyl)(phenyl)sulfide (Intermediate E)

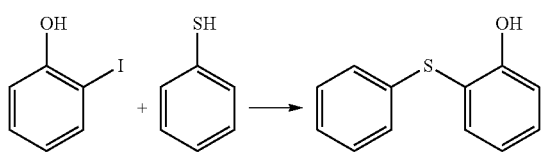

To a mixture of 130 g of 2-iodophenol, 11.3 g of copper iodide, and 520 g of N-methylpyrrolidone, 104 g of benzenethiol was added dropwise. Under heating at 110° C., 138 g of diisopropylethylamine was added dropwise to the mixture, which was aged at 110° C. for 13 hours. The reaction solution was combined with 708 g of 10 wt % sodium hydroxide aqueous solution and washed with 3.9 kg of hexane. Then 186 g of 35 wt % dilute hydrochloric acid was added, and 1.3 kg of ethyl acetate added. The organic layer was separated, and washed with saturated ammonium chloride aqueous solution and then with water. The organic layer was concentrated in vacuum. The concentrate was distilled under reduced pressure, obtaining the desired compound, (4-tert-butylphenyl)(phenyl)sulfide (Intermediate E) (amount 106 g, yield 88%).

(2) Synthesis of 2-(4-tert-butylphenyl)(phenyl)sulfoniophenolate (Q-C)

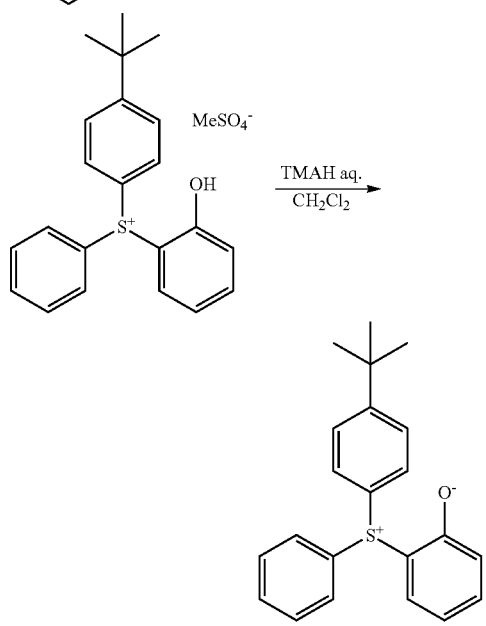

A mixture of 8.1 g of Intermediate E, 24 g of bis(4-tert-butylphenyl)iodonium methylsulfate, 1.2 mg of copper(II) benzoate, and 40 g of anisole was stirred at 80° C. for 1.5 hours. The reaction solution was cooled to room temperature, after which 52 g of methyl tert-butyl ether was added and 130 g of pure water added. The water layer was separated, to which 30 g of methylene chloride was added, and 16 g of 25 wt % tetramethylammonium hydroxide aqueous solution added, followed by 15 minutes of stirring. At the end of stirring, 30 g of methylene chloride was added. The organic layer was separated and washed with water. To the organic layer, 1-pentanol and methyl isobutyl ketone were added, followed by vacuum concentration. Methyl tert-butyl ether was added to the residue for recrystallization. The crystal was recovered and dried in vacuum, obtaining the target compound, 2-(4-tert-butylphenyl)(phenyl)sulfoniophenolate (Q-C) (amount 5.5 g, yield 41%).

Figure 4:
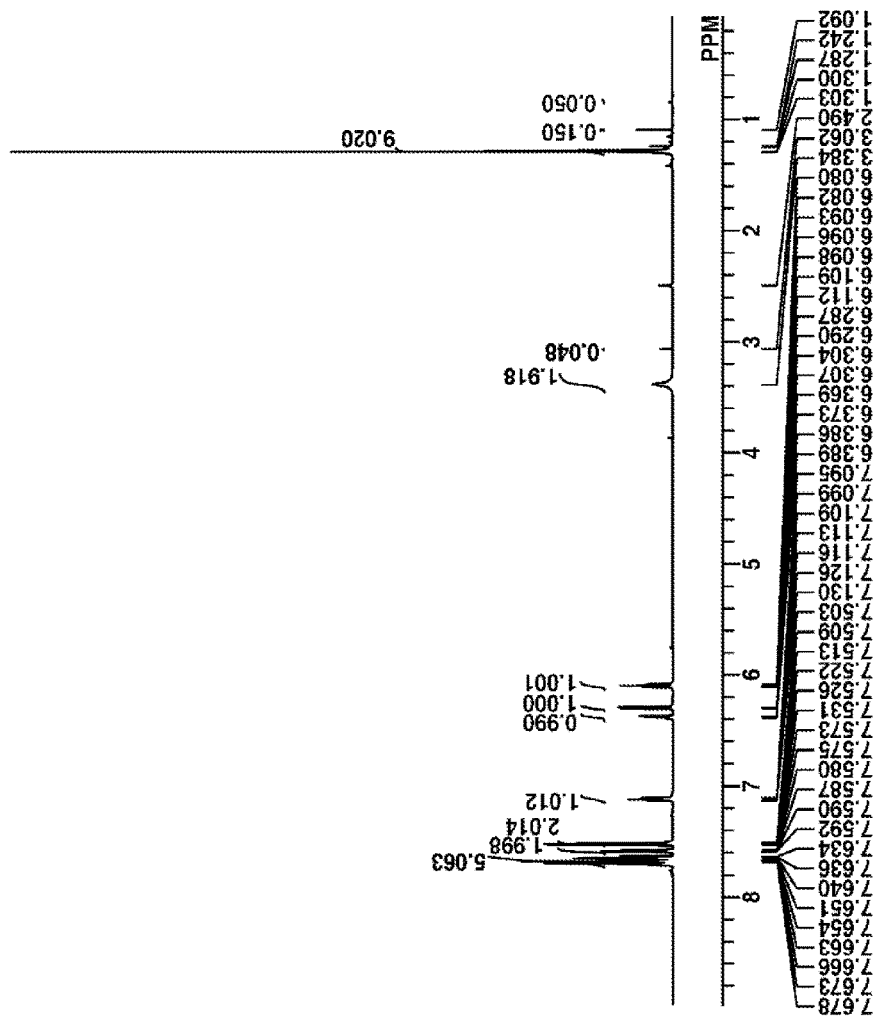
FIG. 4 is a diagram of $^1$H-NMR spectrum of compound Q-C obtained in Example 1-3.

The target compound was analyzed by spectroscopy. The NMR spectrum, $^1$H-NMR in DMSO-$d_6$ is shown in FIG. 4. In $^1$H-NMR analysis, minute amounts of residual solvents (1-pentanol, methyl isobutyl ketone, methyl tert-butyl ether) and water were observed.

IR (D-ATR): ν=3450, 2968, 1578, 1478, 1474, 1447, 1356, 1287, 1010, 845, 765, 750, 687 cm$^{-1}$

LC-MS: Positive [M+H]$^+$ 335 (corresponding to $C_{22}H_{23}OS^+$)

2) Synthesis of Polymers

Polymers for use in resist compositions were synthesized according to the following formulation. Notably, Mw is measured by GPC versus polystyrene standards.

Synthesis Example 1

Synthesis of Polymer P1

Under a nitrogen blanket, a flask was charged with 22 g of 1-tert-butylcyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of methyl ethyl ketone (MEK) to form a monomer/initiator solution. Another flask under a nitrogen blanket was charged with 23 g of MEK and heated at 80° C. with stirring, after which the monomer/initiator solution was added dropwise over 4 hours. After the completion of dropwise addition, the polymerization solution was continuously stirred for 2 hours while keeping the temperature of 80° C. It was then cooled to room temperature. With vigorous stirring, the polymerization solution was added dropwise to 640 g of methanol where a polymer precipitated. The polymer was collected by filtration, washed twice with 240 g of methanol, and vacuum dried at 50° C. for 20 hours, obtaining 36 g of the polymer in white powder form (yield 90%). The polymer (designated Polymer P1) was analyzed for composition. On GPC analysis, the polymer had a Mw of 8,755 and a Mw/Mn of 1.94.

Polymer P1

(a = 0.50, b = 0.50)

Synthesis Examples 2 to 12

Synthesis of Polymers P2 to P12

Polymers P2 to P12 were prepared by the same procedure as in Synthesis Example 1 except that the type and amount of monomers used were changed. The compositional proportions of the polymers thus prepared are shown in Table 1 where values are molar ratios of monomer units incorporated. The structures of units in Table 1 are shown in Tables 2 and 3.

TABLE 1

|  | Resin | Unit 1 (ratio) | Unit 2 (ratio) | Unit 3 (ratio) | Unit 4 (ratio) | Mw | Mw/Mn |
|---|---|---|---|---|---|---|---|
| Synthesis Example | 1 Polymer P1 | A-1 (0.50) | B-1 (0.50) | — | — | 8,755 | 1.94 |
|  | 2 Polymer P2 | A-3 (0.50) | B-1 (0.50) | — | — | 8,052 | 1.77 |
|  | 3 Polymer P3 | A-1 (0.40) | B-1 (0.50) | B-2 (0.10) | — | 8,297 | 1.70 |
|  | 4 Polymer P4 | A-2 (0.40) | B-1 (0.60) | — | — | 8,802 | 1.58 |
|  | 5 Polymer P5 | A-2 (0.40) | B-3 (0.60) | — | — | 8,118 | 1.91 |
|  | 6 Polymer P6 | A-2 (0.20) | A-3 (0.30) | B-1 (0.40) | B-4 (0.10) | 8,192 | 1.90 |
|  | 7 Polymer P7 | A-2 (0.20) | A-3 (0.30) | B-2 (0.40) | B-4 (0.10) | 8,684 | 1.85 |
|  | 8 Polymer P8 | A-1 (0.25) | A-2 (0.25) | B-2 (0.40) | B-4 (0.10) | 8,214 | 1.89 |
|  | 9 Polymer P9 | A-1 (0.25) | A-2 (0.20) | B-1 (0.35) | B-2 (0.20) | 8,355 | 1.89 |
|  | 10 Polymer P10 | A-3 (0.25) | A-5 (0.25) | B-1 (0.35) | B-4 (0.15) | 8,511 | 1.88 |
|  | 11 Polymer P11 | A-4 (0.50) | B-3 (0.50) | — | — | 8,652 | 1.78 |
|  | 12 Polymer P12 | A-5 (0.30) | A-6 (0.10) | B-2 (0.50) | B-4 (0.10) | 8,278 | 1.82 |

TABLE 2

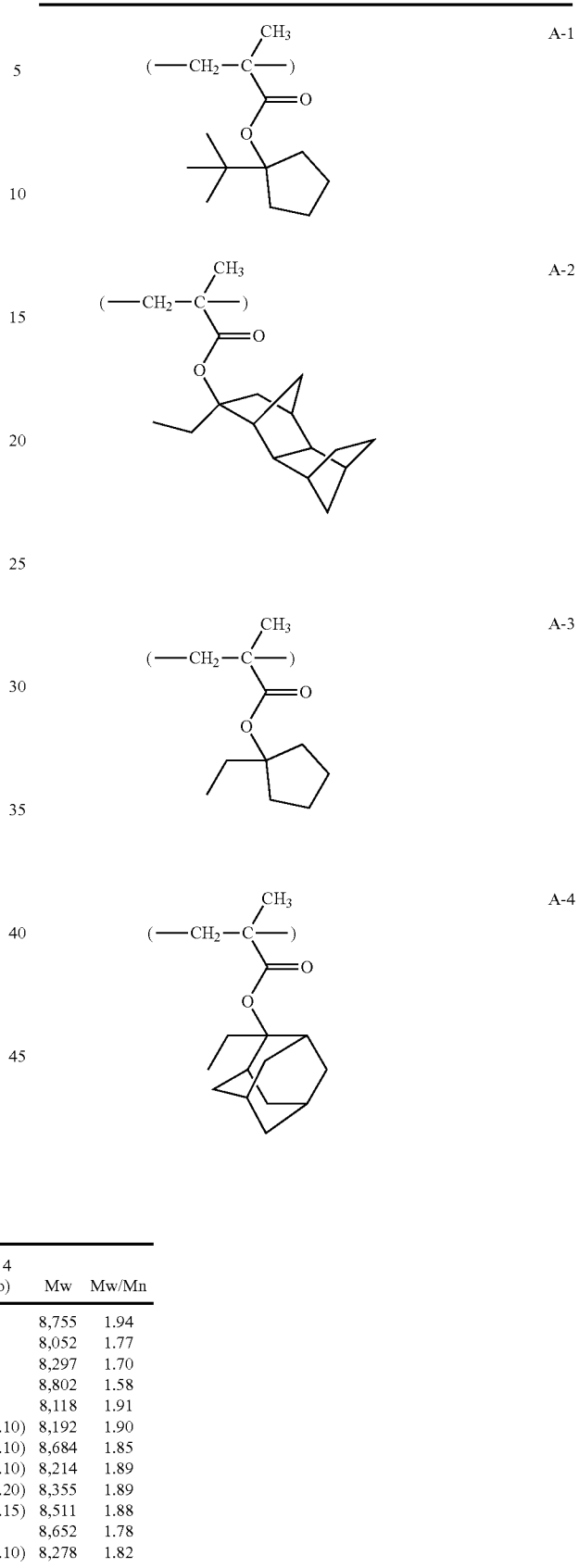

TABLE 2-continued

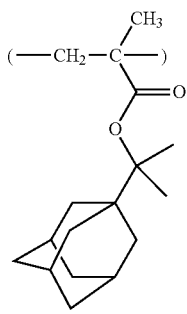
A-5

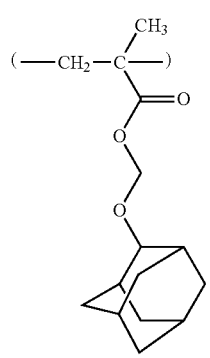 [SMILES: CCC(C)(C)C(=O)OCOC1C2CC3CC(C2)CC1C3]
A-6

TABLE 3

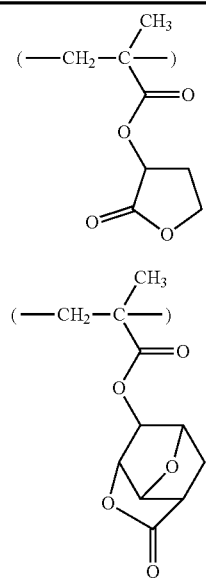
B-1

B-2

B-3

TABLE 3-continued

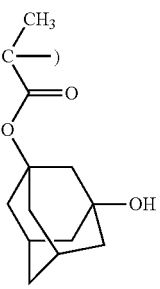
B-4

3) Preparation of Resist Compositions

Examples 2-1 to 2-14 and Comparative Examples 1-1 to 1-6

A resist solution was prepared by selecting an acid diffusion inhibitor (Q-A, Q-B or Q-C) or comparative acid diffusion inhibitor (Q-1 to Q-6), polymer (P1 to P12), PAG, and alkali-soluble surfactant SF-1 in accordance with the formulation shown in Table 4, dissolving the components in a solvent, and filtering through a Teflon® filter having a pore size of 0.2 μm. The solvent contained 0.01 wt % of surfactant A.

The solvent, PAG, alkali-soluble surfactant SF-1, surfactant A, and comparative acid diffusion inhibitors (Q-1 to Q-6) in Table 4 are identified below.

Solvent:
  PGMEA (propylene glycol monomethyl ether acetate)
  GBL (γ-butyrolactone)

PAG-X:
  triphenylsulfonium 2-(adamantane-1-carbonyloxy)-1,1,3,3,3-pentafluoropropane-1-sulfonate Comparative Acid Diffusion Inhibitors:
  Q-1: 2-(4-morpholinyl)ethyl laurate
  Q-2: triphenylsulfonium 10-camphorsulfonate
  Q-3: triphenylsulfonium salicylate
  Q-4: diphenyliodonium 2-carboxylate
  Q-5: compound of formula (Q-5), prepared with reference of JP-A 2013-006827, [0147]
  Q-6: compound of formula (Q-6), prepared with reference of JP-A 2016-006495, [0067]

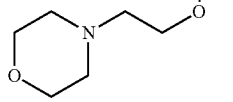
(Q-1)

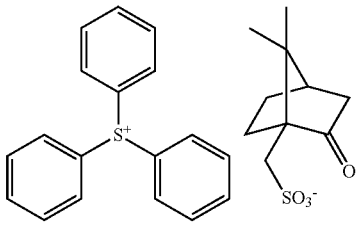
(Q-2)

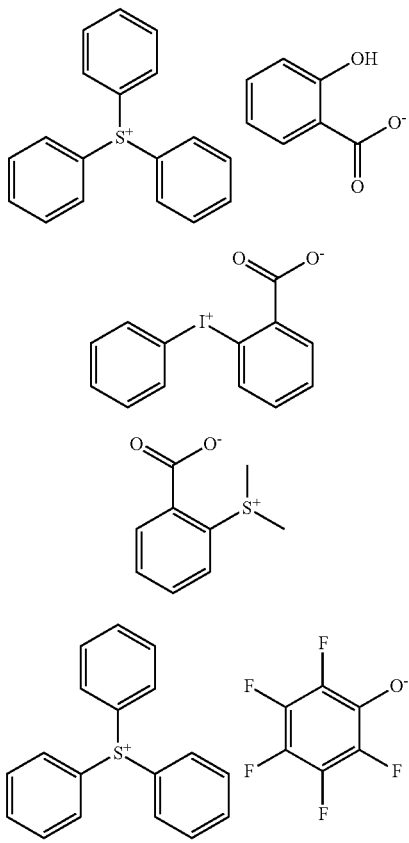

Alkali-soluble Surfactant SF-1:
poly(2,2,3,3,4,4,4-heptafluoro-1-isobutyl-1-butyl methacrylate/9-(2,2,2-trifluoro-1-trifluoroethyloxycarbonyl)-4-oxatricyclo[4.2.1.0$^{3,7}$]-nonan-5-on-2-yl methacrylate) of the structural formula shown below
Mw=7,700
Mw/Mn=1.82

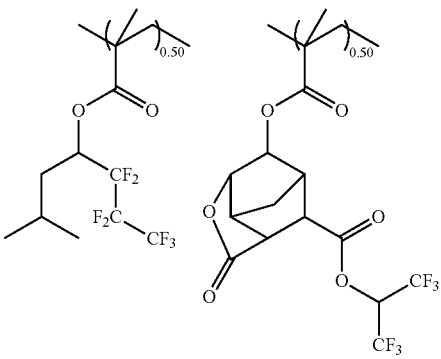

Surfactant A: 3-methyl-3-(2,2,2-trifluoroethoxymethyl)oxetane/tetrahydrofuran/2,2-dimethyl-1,3-propanediol copolymer (Omnova Solutions, Inc.) of the structural formula shown below

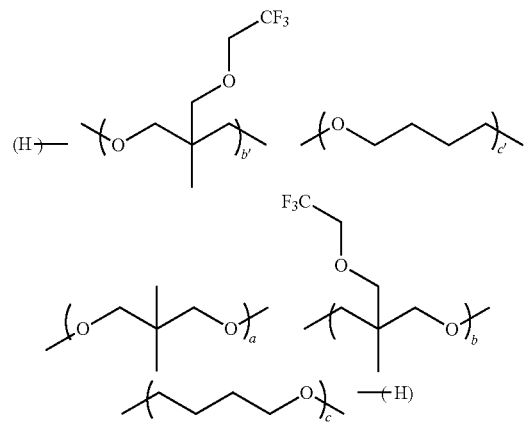

a:(b+b'):(c+c')=1:4-7:0.01-1 (molar ratio)
Mw=1,500

TABLE 4

| | | Resist composition | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|---|
| Example | 2-1 | R-01 | Polymer P1 (80) | PAG-X (7.6) | Q-A (1.6) | SF-1 (3.0) | PGMEA (1,728) | GBL (192) |
| | 2-2 | R-02 | Polymer P1 (80) | PAG-X (7.6) | Q-B (1.6) | SF-1 (3.0) | PGMEA (1,728) | GBL (192) |
| | 2-3 | R-03 | Polymer P2 (80) | PAG-X (7.6) | Q-A (1.6) | SF-1 (3.0) | PGMEA (1,728) | GBL (192) |
| | 2-4 | R-04 | Polymer P3 (80) | PAG-X (7.6) | Q-A (1.6) | SF-1 (3.0) | PGMEA (1,728) | GBL (192) |
| | 2-5 | R-05 | Polymer P4 (80) | PAG-X (7.6) | Q-A (1.6) | SF-1 (3.0) | PGMEA (1,728) | GBL (192) |
| | 2-6 | R-06 | Polymer P5 (80) | PAG-X (7.6) | Q-A (1.6) | SF-1 (3.0) | PGMEA (1,728) | GBL (192) |
| | 2-7 | R-07 | Polymer P6 (80) | PAG-X (7.6) | Q-A (1.6) | SF-1 (3.0) | PGMEA (1,728) | GBL (192) |
| | 2-8 | R-08 | Polymer P7 (80) | PAG-X (7.6) | Q-A (1.6) | SF-1 (3.0) | PGMEA (1,728) | GBL (192) |
| | 2-9 | R-09 | Polymer P8 (80) | PAG-X (7.6) | Q-A (1.6) | SF-1 (3.0) | PGMEA (1,728) | GBL (192) |
| | 2-10 | R-10 | Polymer P9 (80) | PAG-X (7.6) | Q-A (1.6) | SF-1 (3.0) | PGMEA (1,728) | GBL (192) |
| | 2-11 | R-11 | Polymer P10 (80) | PAG-X (7.6) | Q-A (1.6) | SF-1 (3.0) | PGMEA (1,728) | GBL (192) |

TABLE 4-continued

|  | Resist composition | Resin (pbw) | PAG (pbw) | Acid diffusion inhibitor (pbw) | Surfactant (pbw) | Solvent 1 (pbw) | Solvent 2 (pbw) |
|---|---|---|---|---|---|---|---|
|  | 2-12 | R-12 | Polymer P11 (80) | PAG-X (7.6) | Q-A (1.6) | SF-1 (3.0) | PGMEA (1,728) | GBL (192) |
|  | 2-13 | R-13 | Polymer P12 (80) | PAG-X (7.6) | Q-A (1.6) | SF-1 (3.0) | PGMEA (1,728) | GBL (192) |
|  | 2-14 | R-14 | Polymer P1 (80) | PAG-X (7.6) | Q-C (1.7) | SF-1 (3.0) | PGMEA (1,728) | GBL (192) |
| Comparative Example | 1-1 | R-15 | Polymer P1 (80) | PAG-X (7.6) | Q-1 (1.3) | SF-1 (3.0) | PGMEA (1,728) | GBL (192) |
|  | 1-2 | R-16 | Polymer P1 (80) | PAG-X (7.6) | Q-2 (3.8) | SF-1 (3.0) | PGMEA (1,728) | GBL (192) |
|  | 1-3 | R-17 | Polymer P1 (80) | PAG-X (7.6) | Q-3 (3.1) | SF-1 (3.0) | PGMEA (1,728) | GBL (192) |
|  | 1-4 | R-18 | Polymer P1 (80) | PAG-X (7.6) | Q-4 (2.5) | SF-1 (3.0) | PGMEA (1,728) | GBL (192) |
|  | 1-5 | R-19 | Polymer P1 (80) | PAG-X (7.6) | Q-5 (1.4) | SF-1 (3.0) | PGMEA (1,728) | GBL (192) |
|  | 1-6 | R-20 | Polymer P1 (80) | PAG-X (7.6) | Q-6 (3.5) | SF-1 (3.0) | PGMEA (1,728) | GBL (192) |

4) Evaluation of Resist Composition: ArF Lithography Test 1

Examples 3-1 to 3-14 and Comparative Examples 2-1 to 2-6

An antireflective coating solution (ARC-29A by Nissan Chemical Industries, Ltd.) was coated onto a silicon substrate and baked at 200° C. for 60 seconds to form an ARC film of 100 nm thick. The resist solution (R-01 to R-20) in Table 4 was spin coated onto the ARC and baked on a hotplate at 90° C. for 60 seconds to form a resist film of 90 nm thick. The resist film was exposed according to the ArF immersion lithography using an ArF excimer laser scanner (model NSR-S610C, Nikon Corp., NA 1.30, quadrupole illumination, 6% halftone phase shift mask). Water was used as the immersion liquid. The resist film was baked (PEB) at the temperature shown in Table 5 for 60 seconds and developed in a 2.38 wt % tetramethylammonium hydroxide (TMAH) aqueous solution for 60 seconds.

Evaluation Method

The resist was evaluated by observing a 40-nm 1:1 line-and-space pattern under an electron microscope. The optimum dose (Eop) was a dose (mJ/cm$^2$) which provided a line width of 40 nm.

The roughness of the sidewall of the line pattern at the optimum dose was determined by computing a variation of line width (measured at 30 points, 3σ value computed), with the data reported as LWR (nm). A smaller value of LWR indicates a line pattern with a less fluctuation and of better profile.

Exposure was made through a mask having a fixed pitch of 80 nm and a varying line width in a range from 38 nm to 42 nm by an increment of 1 nm, scaled as on-wafer size at the optimum dose. The size of the pattern transferred to the wafer was measured. With respect to the line width, the size of the transferred pattern is plotted relative to the mask design size, and a gradient is computed by linear approximation, and reported as mask error factor (MEF). A smaller MEF value, indicative of reduced influence of a finish error of the mask pattern, is better.

The collapse limit was a minimum width (nm) of lines which could be resolved without collapse when the line size was narrowed by increasing the exposure dose. A smaller value indicates better collapse resistance.

The test results are shown in Table 5.

TABLE 5

|  |  | Resist composition | PEB temp. (° C.) | Eop (mJ/cm$^2$) | LWR (nm) | MEF | Collapse limit (nm) |
|---|---|---|---|---|---|---|---|
| Example | 3-1 | R-01 | 75 | 32 | 3.0 | 2.4 | 30 |
|  | 3-2 | R-02 | 75 | 35 | 2.9 | 2.4 | 31 |
|  | 3-3 | R-03 | 90 | 38 | 2.8 | 2.6 | 28 |
|  | 3-4 | R-04 | 80 | 38 | 3.2 | 2.2 | 29 |
|  | 3-5 | R-05 | 85 | 35 | 2.9 | 2.4 | 30 |
|  | 3-6 | R-06 | 85 | 36 | 2.8 | 2.3 | 31 |
|  | 3-7 | R-07 | 95 | 38 | 3.1 | 2.2 | 31 |
|  | 3-8 | R-08 | 95 | 37 | 2.9 | 2.2 | 30 |
|  | 3-9 | R-09 | 90 | 38 | 3.0 | 2.3 | 32 |
|  | 3-10 | R-10 | 85 | 34 | 3.1 | 2.5 | 32 |
|  | 3-11 | R-11 | 110 | 35 | 3.0 | 2.4 | 29 |
|  | 3-12 | R-12 | 105 | 39 | 3.2 | 2.3 | 28 |
|  | 3-13 | R-13 | 105 | 42 | 3.3 | 2.4 | 33 |
|  | 3-14 | R-14 | 75 | 30 | 2.8 | 2.4 | 31 |
| Comparative Example | 2-1 | R-15 | 75 | 38 | 3.6 | 3.2 | 38 |
|  | 2-2 | R-16 | 75 | 29 | 3.8 | 3.8 | 40 |
|  | 2-3 | R-17 | 75 | 32 | 3.9 | 3.9 | 44 |
|  | 2-4 | R-18 | 75 | 33 | 3.9 | 3.7 | 42 |

TABLE 5-continued

|  | Resist composition | PEB temp. (° C.) | Eop (mJ/cm²) | LWR (nm) | MEF | Collapse limit (nm) |
|---|---|---|---|---|---|---|
| 2-5 | R-19 | 75 | 31 | 4.1 | 4.1 | 44 |
| 2-6 | R-20 | 75 | 35 | 4.1 | 4.2 | 40 |

It is evident from the data of Table 5 that the resist compositions within the scope of the invention form, through alkaline development, positive patterns having improved LWR, MEF and collapse resistance. They are thus best suited as the ArF immersion lithography material.

5) Evaluation of Resist Composition: ArF Lithography Test 2

Examples 4-1 to 4-14 and Comparative Examples 3-1 to 3-6

On a silicon wafer, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-01 to R-20) in Table 4 was spin coated, then baked on a hotplate at 90° C. for 60 seconds to form a resist film of 90 nm thick. Using an ArF excimer laser immersion lithography scanner NSR-610C (Nikon Corp., NA 1.30, σ0.98/0.74, dipole opening 90 deg., s-polarized illumination), pattern exposure was performed through a mask with a varying exposure dose. After exposure, the resist film was baked (PEB) at the temperature shown in Table 6 for 60 seconds, developed in butyl acetate for 30 seconds, and rinsed with diisopentyl ether. The pattern profile at the optimum dose was compared and visually inspected for rectangularity.

The mask used herein is a halftone phase shift mask having a transmittance of 6% and an on-mask design corresponding to a 45 nm line/90 nm pitch pattern (actual on-mask size is 4 times because of 1/4 image reduction projection exposure). The size of the trench pattern printed in the light-shielded region was measured under a CD-SEM (CG4000 by Hitachi High-Technologies Corp.). The optimum dose (Eop) was the dose (mJ/cm²) that gave a trench width of 45 nm. Further a size variation (3σ) of the trench width at the optimum dose was determined at intervals of 10 nm over a range of 200 nm and reported as LWR (nm).

In the process of forming a trench pattern, as the exposure dose is reduced, the trench size is enlarged and the line size is reduced. The maximum of trench width below which lines can be resolved without collapse is determined and reported as collapse limit (nm). A higher value indicates greater collapse resistance and is preferable.

The test results are shown in Table 6.

TABLE 6

|  |  | Resist composition | PEB temp. (° C.) | Eop (mJ/cm²) | LWR (nm) | Collapse limit (nm) |
|---|---|---|---|---|---|---|
| Example | 4-1 | R-01 | 75 | 32 | 3.6 | 56 |
|  | 4-2 | R-02 | 75 | 34 | 3.6 | 55 |
|  | 4-3 | R-03 | 90 | 37 | 3.7 | 54 |
|  | 4-4 | R-04 | 80 | 38 | 3.6 | 55 |
|  | 4-5 | R-05 | 85 | 36 | 3.5 | 57 |
|  | 4-6 | R-06 | 85 | 35 | 3.9 | 55 |

TABLE 6-continued

|  |  | Resist composition | PEB temp. (° C.) | Eop (mJ/cm²) | LWR (nm) | Collapse limit (nm) |
|---|---|---|---|---|---|---|
|  | 4-7 | R-07 | 95 | 36 | 3.6 | 58 |
|  | 4-8 | R-08 | 95 | 37 | 3.8 | 57 |
|  | 4-9 | R-09 | 90 | 37 | 3.7 | 56 |
|  | 4-10 | R-10 | 85 | 35 | 3.6 | 54 |
|  | 4-11 | R-11 | 110 | 34 | 4.0 | 53 |
|  | 4-12 | R-12 | 105 | 38 | 4.1 | 53 |
|  | 4-13 | R-13 | 105 | 39 | 4.0 | 52 |
|  | 4-14 | R-14 | 75 | 31 | 3.5 | 56 |
| Comparative Example | 3-1 | R-15 | 75 | 36 | 5.4 | 34 |
|  | 3-2 | R-16 | 75 | 28 | 5.7 | 31 |
|  | 3-3 | R-17 | 75 | 31 | 5.5 | 32 |
|  | 3-4 | R-18 | 75 | 32 | 5.4 | 33 |
|  | 3-5 | R-19 | 75 | 30 | 5.8 | 30 |
|  | 3-6 | R-20 | 75 | 34 | 5.8 | 28 |

It is evident from the data of Table 6 that the resist compositions within the scope of the invention form, through organic solvent development, negative patterns having improved LWR and collapse resistance. They are thus best suited for lithography micropatterning.

Japanese Patent Application No. 2016-200813 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium compound having the formula (1):

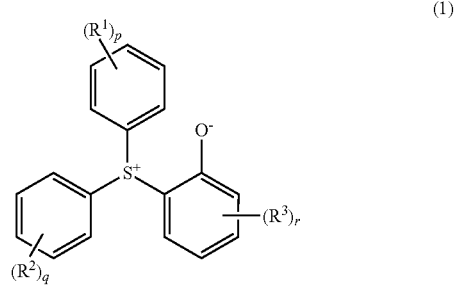

(1)

wherein $R^1$, $R^2$ and $R^3$ are each independently a $C_1$-$C_{20}$ straight, branched or cyclic monovalent hydrocarbon group which may contain a heteroatom, p and q are each independently an integer of 0 to 5, r is an integer of 0 to 4, in case of p=2 to 5, two adjoining groups $R^1$ may bond together to form a ring with the carbon atoms to which they are attached, in case of q=2 to 5, two adjoining groups $R^2$ may bond together to form a ring with the carbon atoms to which they are attached, and in case of r=2 to 4, two adjoining groups $R^3$ may bond together to form a ring with the carbon atoms to which they are attached.

2. A resist composition comprising (A) the sulfonium compound of claim 1, (B) an organic solvent, (C) a base resin, and (D) a photoacid generator.

3. The resist composition of claim 2, wherein the base resin (C) is a polymer comprising recurring units having an acid labile group.

4. The resist composition of claim 3 wherein the recurring units having an acid labile group have the formula (a):

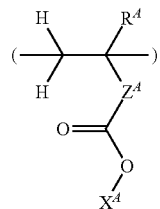

(a)

wherein $R^A$ is hydrogen, fluorine, methyl or trifluoromethyl, $Z^A$ is a single bond, phenylene, naphthylene or (backbone)-C(=O)—O—Z'—, Z' is a $C_1$-$C_{10}$ straight, branched or cyclic alkylene group which may contain a hydroxyl moiety, ether bond, ester bond, or lactone ring, or a phenylene or naphthylene group, and $X^A$ is an acid labile group.

5. The resist composition of claim 3 wherein the polymer further comprises recurring units having the formula (b):

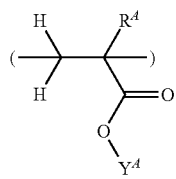

(b)

wherein $R^A$ is hydrogen, fluorine, methyl or trifluoromethyl, and $Y^A$ is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

6. The resist composition of claim 2 wherein the photoacid generator has the formula (2) or (3):

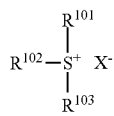

(2)

wherein $R^{101}$, $R^{102}$ and $R^{103}$ are each independently a $C_1$-$C_{20}$ straight, branched or cyclic monovalent hydrocarbon group which may contain a heteroatom, any two of $R^{101}$, $R^{102}$ and $R^{103}$ may bond together to form a ring with the sulfur atom to which they are attached, and X⁻ is an anion selected from the formulae (2A) to (2D):

(2A)

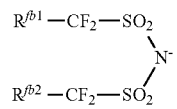

(2B)

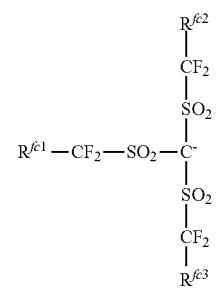

(2C)

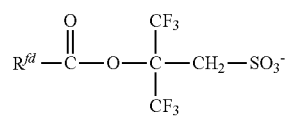

(2D)

wherein $R^{fa}$, $R^{fb1}$, $R^{fb2}$, $R^{fc1}$, $R^{fc2}$, and $R^{fc3}$ are each independently fluorine or a $C_1$-$C_{40}$ straight, branched or cyclic monovalent hydrocarbon group which may contain a heteroatom, $R^{fb1}$ and $R^{fb2}$, or $R^{fc1}$ and $R^{fc2}$ may bond together to form a ring with the carbon atoms to which they are attached and the atoms therebetween, $R^{fd}$ is a $C_1$-$C_{40}$ straight, branched or cyclic monovalent hydrocarbon group which may contain a heteroatom,

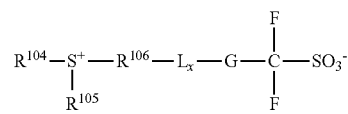

(3)

wherein $R^{104}$ and $R^{105}$ are each independently a $C_1$-$C_{20}$ straight, branched or cyclic monovalent hydrocarbon group which may contain a heteroatom, $R^{104}$ and $R^{105}$ may bond together to form a ring with the sulfur atom to which they are attached, $R^{106}$ is a $C_1$-$C_{20}$ straight, branched or cyclic divalent hydrocarbon group which may contain a heteroatom, G is a single bond or a $C_1$-$C_{20}$ straight, branched or cyclic divalent hydrocarbon group which may contain a heteroatom, and $L_x$ is a divalent linking group.

7. The resist composition of claim 2, further comprising (E) a nitrogen-containing compound.

8. The resist composition of claim 2, further comprising (F) a surfactant which is insoluble or substantially insoluble in water and soluble in alkaline developer and/or a surfactant which is insoluble or substantially insoluble in water and alkaline developer.

9. A pattern forming process comprising the steps of applying the resist composition of claim 2 onto a substrate, prebaking to form a resist film, exposing the resist film to KrF excimer laser, ArF excimer laser, EB or EUV through a photomask, baking, and developing the exposed resist film in a developer.

10. The pattern forming process of claim 9 wherein the exposing step is by immersion lithography wherein a liquid having a refractive index of at least 1.0 is interposed between the resist film and a projection lens.

11. The pattern forming process of claim 10, further comprising the step of forming a protective film on the resist film, and in the immersion lithography, the liquid is interposed between the protective film and the projection lens.

* * * * *